United States Patent
Lee et al.

(10) Patent No.: US 7,049,076 B2
(45) Date of Patent: May 23, 2006

(54) METHOD FOR ASSAYING PROTEIN—PROTEIN INTERACTION

(75) Inventors: Kevin J. Lee, New York, NY (US); Richard Axel, New York, NY (US); Walter Strapps, New York, NY (US); Gilad Barnea, New York, NY (US)

(73) Assignees: Sentigen Biosciences, Inc., New York, NY (US); The Trustees of Columbia University of the City of New York, New York, NY (US)

( * ) Notice: Subject to any disclaimer, the term of this patent is extended or adjusted under 35 U.S.C. 154(b) by 0 days.

(21) Appl. No.: 10/888,313

(22) Filed: Jul. 9, 2004

(65) Prior Publication Data

US 2005/0100934 A1 May 12, 2005

Related U.S. Application Data

(60) Provisional application No. 60/566,113, filed on Apr. 27, 2004, provisional application No. 60/511,918, filed on Oct. 15, 2003, provisional application No. 60/485,968, filed on Jul. 9, 2003.

(51) Int. Cl.
*C07H 21/04* (2006.01)
*C12Q 1/68* (2006.01)
*G01N 33/53* (2006.01)
*G01N 33/567* (2006.01)
*C12N 15/63* (2006.01)
*C12Q 1/60* (2006.01)

(52) U.S. Cl. .................. 435/6; 435/7.2; 435/7.21; 435/320.1; 536/23.1; 536/23.4

(58) Field of Classification Search .................. None
See application file for complete search history.

(56) References Cited

U.S. PATENT DOCUMENTS

| | | | |
|---|---|---|---|
| 5,168,062 A | 12/1992 | Stinski | |
| 5,283,173 A | 2/1994 | Fields et al. | |
| 5,284,746 A | 2/1994 | Sledziewski et al. | |
| 5,385,839 A | 1/1995 | Stinski | |
| 5,464,758 A | 11/1995 | Gossen et al. | |
| 5,468,614 A | 11/1995 | Fields et al. | |
| 5,491,084 A | 2/1996 | Chalfie et al. | |
| 5,667,973 A | 9/1997 | Fields et al. | |
| 5,814,618 A | 9/1998 | Bujard et al. | |
| 5,891,646 A | 4/1999 | Barak et al. | |
| 6,110,693 A | 8/2000 | Barak et al. | |
| 6,333,167 B1 | 12/2001 | Quinet et al. | |
| 6,455,300 B1 | 9/2002 | Htun et al. | |
| 6,528,271 B1 | 3/2003 | Bohn et al. | |
| 2002/0106739 A1 | 8/2002 | Oakely et al. | |
| 2002/0132327 A1 | 9/2002 | Hay et al. | |
| 2003/0013137 A1 | 1/2003 | Barak et al. | |
| 2003/0049712 A1 | 3/2003 | Haugwitz | |
| 2003/0082642 A1 | 5/2003 | Htun et al. | |
| 2003/0143626 A1 | 7/2003 | Colas et al. | |
| 2003/0157553 A1 | 8/2003 | Berstein | |
| 2004/0002119 A1 | 1/2004 | Iannone et al. | |
| 2005/0084864 A1* | 4/2005 | Rossner et al. | 435/6 |

FOREIGN PATENT DOCUMENTS

WO  WO-03/076932 A2  9/2003

* cited by examiner

*Primary Examiner*—David Guzo
*Assistant Examiner*—Michele K. Joike
(74) *Attorney, Agent, or Firm*—Fulbright & Jaworski LLP

(57) ABSTRACT

The invention relates to a method for determining if a test compound, or a mix of compounds, modulates the interaction between two proteins of interest. The determination is made possible via the use of two recombinant molecules, one of which contains the first protein a cleavage site for a proteolytic molecules, and an activator of a gene. The second recombinant molecule includes the second protein and the proteolytic molecule. If the test compound binds to the first protein, a reaction is initiated whereby the activator is cleaved, and activates a reporter gene.

42 Claims, 10 Drawing Sheets

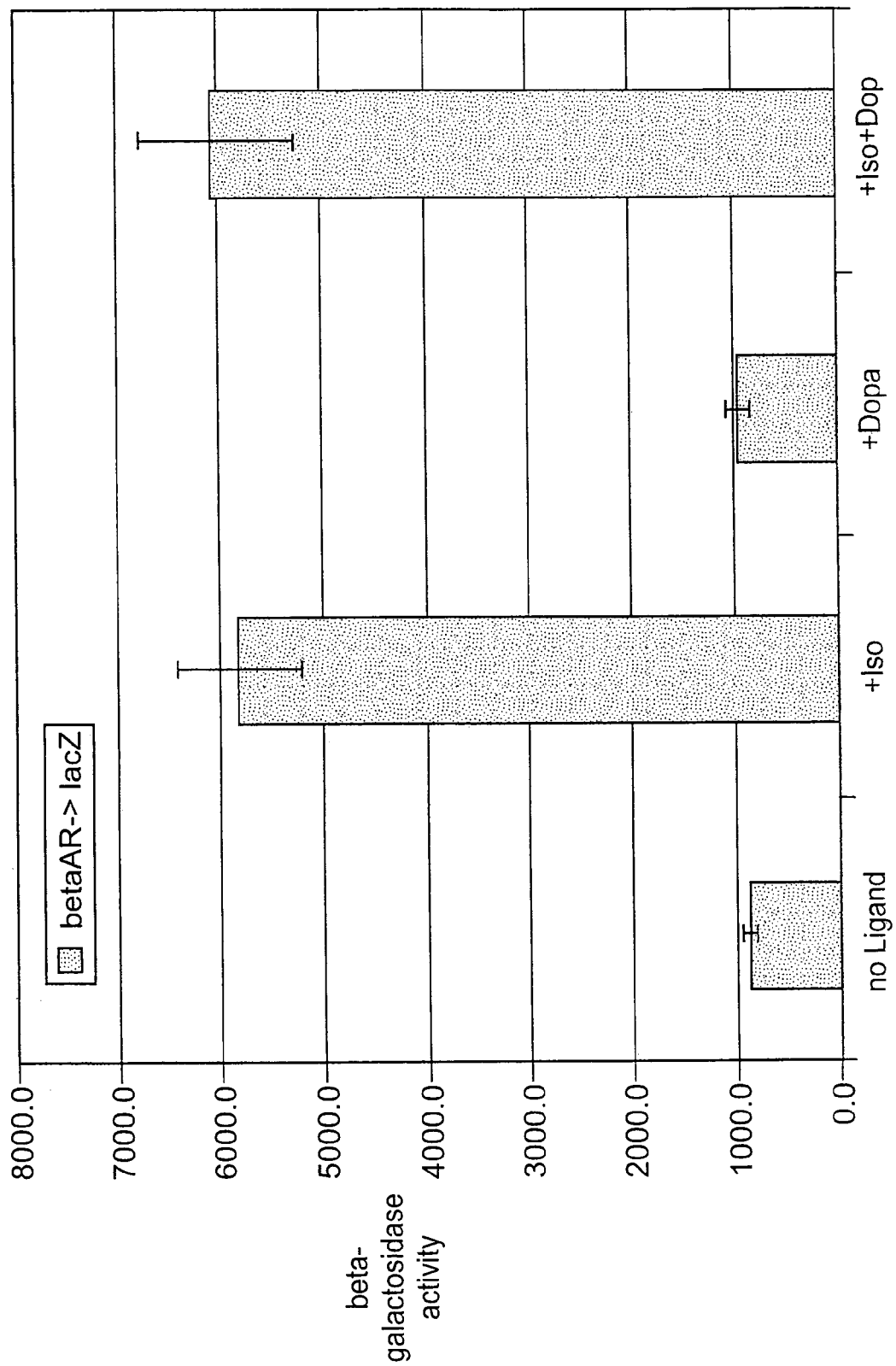

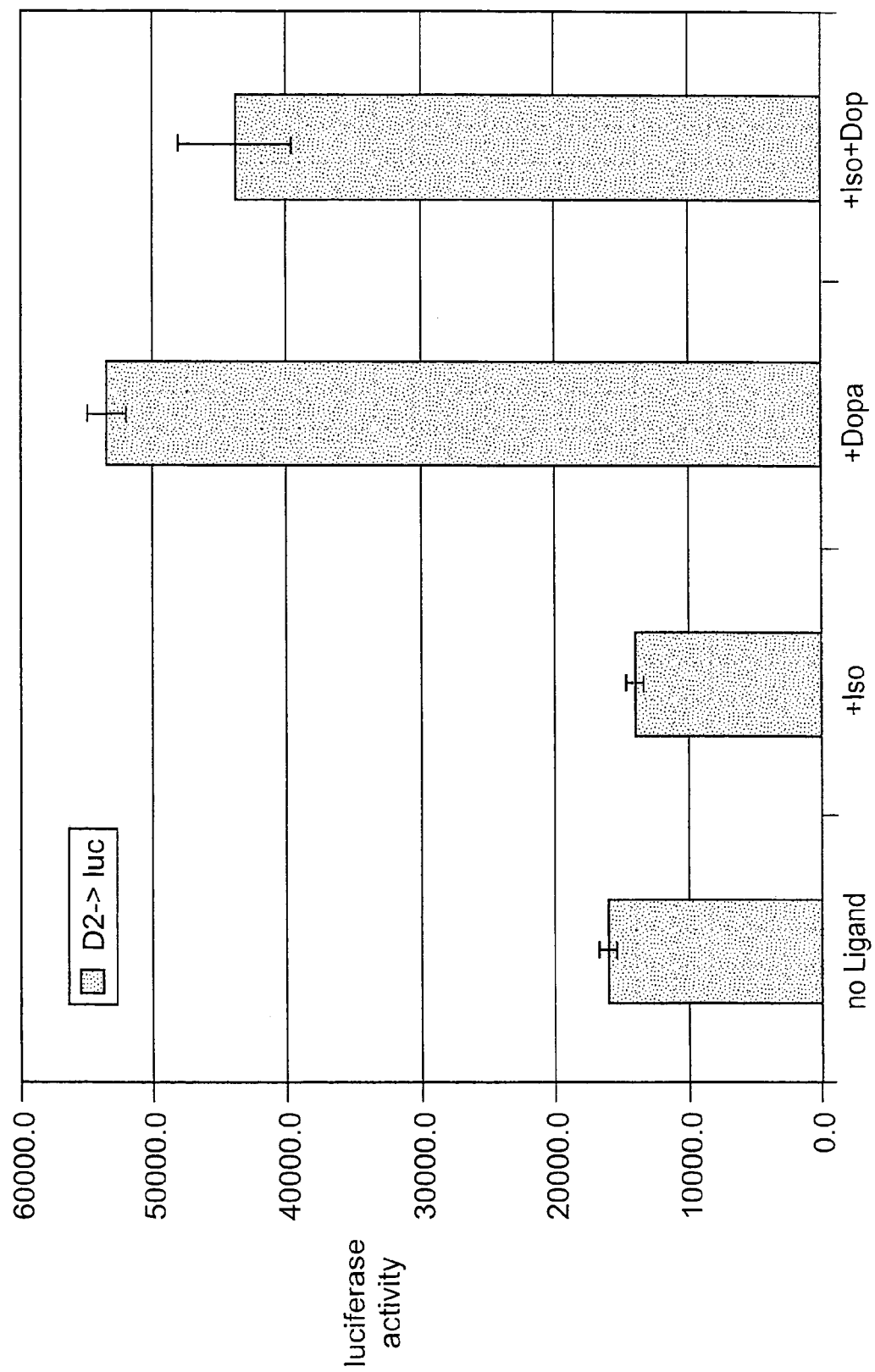

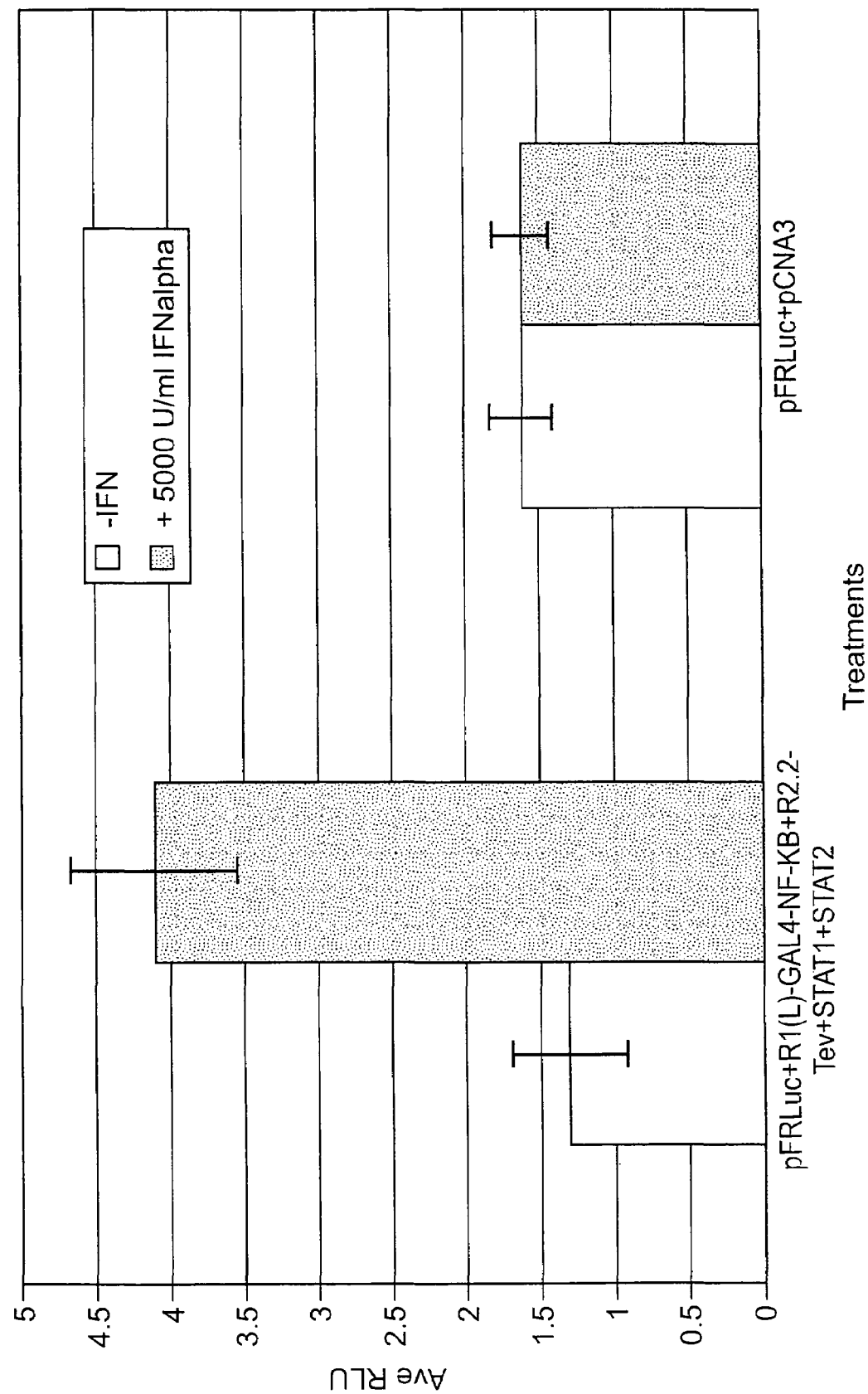

METHOD FOR ASSAYING PROTEIN—PROTEIN INTERACTION

RELATED APPLICATIONS

This application claims priority of Application No. 60/566,113 filed Apr. 27, 2004, which claims priority of Application No. 60/511,918, filed Oct. 15, 2003, which claims priority of Application No. 60/485,968 filed Jul. 9, 2003, all of which are incorporated by reference in their entirety.

FIELD OF THE INVENTION

This invention relates to methods for determining interaction between molecules of interest. More particularly, it relates to determining if a particular substance referred to as the test compound modulates the interaction of two or more specific proteins of interest, via determining activation of a reporter gene in a cell, where the activation, or lack thereof, results from the modulation or its absence. The determination occurs using transformed or transfected cells, which are also a feature of the invention, as are the agents used to transform or transfect them.

BACKGROUND AND RELATED ART

The study of protein/protein interaction, as exemplified, e.g., by the identification of ligands for receptors, is an area of great interest. Even when a ligand or ligands for a given receptor are known, there is interest in identifying more effective or more selective ligands. GPCRs will be discussed herein as a non-exclusive example of a class of proteins which can be studied in this way.

The G-protein coupled receptors, or "GPCRs" hereafter, are the largest class of cell surface receptors known for humans. Among the ligands recognized by GPCRs are hormones, neurotransmitters, peptides, glycoproteins, lipids, nucleotides, and ions. They also act as receptors for light, odors, pheromones, and taste. Given these various roles, it is perhaps not surprising that they are the subject of intense research, seeking to identify drugs useful in various conditions. The success rate has been phenomenal. Indeed, Howard, et al., *Trends Pharmacol. Sci.*, 22:132–140 (2001) estimate that over 50% of marketed drugs act on such receptors. "GPCRs" as used herein, refers to any member of the GPCR superfamily of receptors characterized by a seven-transmembrane domain (7TM) structure. Examples of these receptors include, but are not limited to, the class A or "rhodopsin-like" receptors; the class B or "secretin-like" receptors; the class C or "metabotropic glutamate-like" receptors; the Frizzled and Smoothened-related receptors; the adhesion receptor family or EGF-7TM/LNB-7TM receptors; adiponectin receptors and related receptors; and chemosensory receptors including odorant, taste, vomero-nasal and pheromone receptors. As examples, the GPCR superfamily in humans includes but is not limited to those receptor molecules described by Vassilatis, et al., *Proc. Natl. Acad. Sci. USA*, 100:4903–4908 (2003); Takeda, et al., *FEBS Letters*, 520:97–101 (2002); Fredricksson, et al., *Mol. Pharmacol.*, 63:1256–1272 (2003); Glusman, et al., *Genome Res.*, 11:685–702 (2001); and Zozulya, et al., *Genome Biol.*, 2:0018.1–0018.12 (2001), all of which are incorporated by reference.

The mechanisms of action by which GPCRs function has been explicated to some degree. In brief, when a GPCR binds a ligand, a conformational change results, stimulating a cascade of reactions leading to a change in cell physiology. It is thought that GPCRs transduce signals by modulating the activity of intracellular, heterotrimeric guanine nucleotide binding proteins, or "G proteins". The complex of ligand and receptor stimulates guanine nucleotide exchange and dissociation of the G protein heterotrimer into $\alpha$ and $\beta\gamma$ subunits.

Both the GTP-bound a subunit and the $\beta\gamma$ dimer can act to regulate various cellular effector proteins, including adenylyl cyclase and phospholipase C (PLC). In conventional cell based assays for GPCRs, receptor activity is monitored by measuring the output of a G-protein regulated effector pathway, such as the accumulation of cAMP that is produced by adenylyl cyclase, or the release of intracellular calcium, which is stimulated by PLC activity.

Conventional G-protein based, signal transduction assays have been difficult to develop for some targets, as a result of two major issues.

First, different GPCRs are coupled to different G protein regulated signal transduction pathways, and G-protein based assays are dependent on knowing the G-protein specificity of the target receptor, or require engineering of the cellular system, to force coupling of the target receptor to a particular effect or pathway. Second, all cells express a large number of endogenous GPCRs, as well as other signaling factors. As a result, the effector pathways that are measured may be modulated by other endogenous molecules in addition to the target GPCR, potentially leading to false results.

Regulation of G-protein activity is not the only result of ligand/GPCR binding. Luttrell, et al., *J. Cell Sci.*, 115: 455–465 (2002), and Ferguson, *Pharmacol. Rev.*, 53:1–24 (2001), both of which are incorporated by reference, review other activities which lead to termination of the GPCR signal. These termination processes prevent excessive cell stimulation, and enforce temporal linkage between extracellular signal and corresponding intracellular pathway.

In the case of binding of an agonist to GPCR, serine and threonine residues at the C terminus of the GPCR molecule are phosphorylated. This phosphorylation is caused by the GPCR kinase, or "GRK," family. Agonist complexed, C-terminal phosphorylated GPCRs interact with arrestin family members, which "arrest" receptor signaling. This binding inhibits coupling of the receptor to G proteins, thereby targeting the receptor for internalization, followed by degradation and/or recycling. Hence, the binding of a ligand to a GPCR can be said to "modulate" the interaction between the GPCR and arrestin protein, since the binding of ligand to GPCR causes the arrestin to bind to the GPCR, thereby modulating its activity. Hereafter, when "modulates" or any form thereof is used, it refers simply to some change in the way the two proteins of the invention interact, when the test compound is present, as compared to how these two proteins interact, in its absence. For example, the presence of the test compound may strengthen or enhance the interaction of the two proteins, weaken it, inhibit it, or lessen it in some way, manner or form which can then be detected.

This background information has led to alternate methods for assaying activation and inhibition of GPCRs. These methods involve monitoring interaction with arrestins. A major advantage of this approach is that no knowledge of G-protein pathways is necessary.

Oakley, et al., *Assay Drug Dev. Technol.*, 1:21–30 (2002) and U.S. Pat. Nos. 5,891,646 and 6,110,693, incorporated by reference, describe assays where the redistribution of fluorescently labelled arrestin molecules in the cytoplasm to activated receptors on the cell surface is measured. These methods rely on high resolution imaging of cells, in order to measure arrestin relocalization and receptor activation. It will be recognized by the skilled artisan that this is a complex, involved procedure.

Various other U.S. patents and patent applications dealing with these points have issued and been filed. For example, U.S. Pat. No. 6,528,271 to Bohn, et al., deals with assays for screening for pain controlling medications, where the inhibitor of β-arrestin binding is measured. Published U.S. patent applications, such as 2004/0002119, 2003/0157553, 2003/0143626, and 2002/0132327, all describe different forms of assays involving GPCRs. Published application 2002/0106379 describes a construct which is used in an example which follows; however, it does not teach or suggest the invention described herein.

It is an object of the invention to develop a simpler assay for monitoring and/or determining modulation of specific protein/protein interactions, where the proteins include but are not limited to, membrane bound proteins, such as receptors, GPCRs in particular. How this is accomplished will be seen in the examples which follow.

SUMMARY OF THE INVENTION

Thus, in accordance with the present invention, there is provided a method for determining if a test compound modulates a specific protein/protein interaction of interest comprising contacting said compound to a cell which has been transformed or transfected with (a) a nucleic acid molecule which comprises, (i) a nucleotide sequence which encodes said first test protein, (ii) a nucleotide sequence encoding a cleavage site for a protease or a portion of a protease, and (iii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, and (ii) a nucleotide sequence which encodes a protease or a portion of a protease which is specific for said cleavage site, and determining activity of said reporter gene as a determination of whether said compound modulates said protein/protein interaction.

The first test protein may be a membrane bound protein, such as a transmembrane receptor, and in particular a GPCR. Particular transmembrane receptors include β-adrenergic receptor (ADRB2), arginine vasopressin receptor 2 (AVPR2). serotonin receptor 1a (HTR1 A), m2 muscarinic acetylcholine receptor (CHRM2), chemokine (C-C motif) receptor 5 (CCR5), dopamine D2 receptor (DRD2), kappa opioid receptor (OPRK), or α1a-adregenic receptor (ADRA1A) although it is to be understood that in all cases the invention is not limited to these specific embodiments. For example, molecules such as the insulin growth factor-1 receptor (IGF-1R), which is a tyrosine kinase, and proteins which are not normally membrane bound, like estrogen receptor 1 (ESR1) and estrogen receptors 2 (ESR2). The protease or portion of a protease may be a tobacco etch virus nuclear inclusion A protease. The protein which activates said reporter gene may be a transcription factor, such as tTA or GAL4. The second protein may be an inhibitory protein, such as an arrestin. The cell may be a eukaryote or a prokaryote. The reporter gene may be an exogenous gene, such as β-galactosidase or luciferase.

The nucleotide sequence encoding said first test protein may be modified to increase interaction with said second test protein. Such modifications include but are not limited to replacing all or part of the nucleotide sequence of the C-terminal region of said first test protein with a nucleotide sequence which encodes an amino acid sequence which has higher affinity for said second test protein than the original sequence. For example, the C-terminal region may be replaced by a nucleotide sequence encoding the C-terminal region of AVPR2, AGTRLI, GRPR, F2RL1, CXCR2/IL-8b, CCR4, or GRPR.

The method may comprise contacting more than one test compound to a plurality of samples of cells, each of said samples being contacted by one or more of said test compounds, wherein each of said cell samples have been transformed or transfected with the aforementioned nucleic acid molecules, and determining activity of reporter genes in said plurality of said samples to determine if any of said test compounds modulate a specific, protein/protein interaction. The method may comprise contacting each of said samples with one test compound, each of which differs from all others, or comprise contacting each of said samples with a mixture of said test compounds.

In another embodiment, there is provided a method for determining if a test compound modulates one or more of a plurality of protein interactions of interest, comprising contacting said test compound to a plurality of samples of cells, each of which has been transformed or transfected with (a) a first nucleic acid molecule comprising, (i) a nucleotide sequence which encodes a first test protein, a nucleotide sequence encoding a cleavage site for a protease, and (ii) a nucleotide sequence which encodes a protein which activates a reporter gene in said cell, (b) a second nucleic acid molecule which comprises, (i) a nucleotide sequence which encodes a second test protein whose interaction with said first test protein in the presence of said test compound of interest is to be measured, (ii) a nucleotide sequence which encodes a protease or a protease which is specific for said cleavage site, wherein said first test protein differs from other first test proteins in each of said plurality of samples, and determining activity of said reporter gene in at one or more of said plurality of samples as a determination of modulation of one or more protein interactions of interest The second test protein may be different in each sample or the same in each sample. All of said samples may be combined in a common receptacle, and each sample comprises a different pair of first and second test proteins. Alternatively, each sample may be tested in a different receptacle. The reporter gene in a given sample may differ from the reporter gene in other samples. The mixture of test compounds may comprise or be present in a biological sample, such as cerebrospinal fluid, urine, blood, serum, pus, ascites, synovial fluid, a tissue extract, or an exudate.

In yet another embodiment, there is provided a recombinant cell, transformed or transfected with (a) a nucleic acid molecule which comprises, (i) a nucleotide sequence which encodes said first test protein, (ii) a nucleotide sequence encoding a cleavage site for a protease or a portion of a protease, and (iii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, and (ii) a nucleotide sequence which encodes a protease or a portion of a protease which is specific for said cleavage site.

One or both of said nucleic acid molecules may be stably incorporated into the genome of said cell. The cell also may have been transformed or transfected with said reporter gene. The first test protein may be a membrane bound protein, such as a transmembrane receptor, and in particular a GPCR. Particular transmembrane receptors include ADRB2, AVPR2, HTR1A, CHRM2, CCR5, DRD2, OPRK, or ADRA1A.

The protease or portion of a protease may be a tobacco etch virus nuclear inclusion A protease. The protein which activates said reporter gene may be a transcription factor, such as tTA or GAL4. The second protein may be an inhibitory protein. The cell may be a eukaryote or a prokaryote. The reporter gene may be an exogenous gene, such as β-galactosidase or luciferase. The nucleotide sequence encoding said first test protein may be modified to increase interaction with said second test protein, such as by replacing all or part of the nucleotide sequence of the C-terminal region of said first test protein with a nucleotide sequence which encodes an amino acid sequence which has higher affinity for said second test protein than the original sequence. The C-terminal region may be replaced by a nucleotide sequence encoding the C-terminal region of AVPR2, AGTRLI, GRPR, F2RL1, CXCR2/IL-8B, CCR4, or GRPR.

In still yet another embodiment, there is provided an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell. The test protein may be a membrane bound protein, such as is a transmembrane receptor. A particular type of transmembrane protein is a GPCR. Particular transmembrane receptors include ADRB2, AVPR2, HTR1A, CHRM2, CCR5, DRD2, OPRK, or ADRA1A. The protease or portion of a protease may be a tobacco etch virus nuclear inclusion A protease. The protein which activates said reporter gene may be a transcription factor, such as tTA or GAL4. As above, the invention is not to be viewed as limited to these specific embodiments.

In still a further embodiment, there is provided an expression vector comprising an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell, and further being operably linked to a promoter.

In still yet a further embodiment, there is provided an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site. The test protein may be an inhibitory protein, such as an arrestin.

Also provided is an expression vector comprising an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site, said nucleic acid further being operably linked to a promoter.

An additional embodiment comprises a fusion protein produced by expression of:

an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell, and further being operably linked to a promoter; or an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site In yet another embodiment, there is provided a test kit useful for determining if a test compound modulates a specific protein/protein interaction of interest comprising a separate portion of each of (a) a nucleic acid molecule which comprises, a nucleotide sequence which encodes said first test protein (i) a nucleotide sequence encoding a cleavage site for a protease or a portion of a protease, (ii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, (ii) a nucleotide sequence which encodes a protease or a portion of a protease which is specific for said cleavage site, and container means for holding each of (a) and (b) separately from each other.

The first test protein may be a membrane bound protein, such as a transmembrane receptor. A particular type of transmembrane receptor is a GPCR. A particular transmembrane protein is a GPCR. Particular transmembrane receptors include ADRB2, AVPR2, HTR1A, CHRM2, CCR5, DRD2, OPRK, or ADRA1A. The protease or portion of a protease may be tobacco etch virus nuclear inclusion A protease. The protein which activates said reporter gene may be a transcription factor, such as tTA or GAL4. The second protein may be an inhibitory protein, such as an arrestin. The kit may further comprise a separate portion of an isolated nucleic acid molecule which encodes a reporter gene. The reporter gene may encode β-galactosidase or luciferase. The nucleotide sequence encoding said first test protein may be modified to increase interaction with said second test protein, such as by replacing all or part of the nucleotide sequence of the C-terminal region of said first test protein with a nucleotide sequence which encodes an amino acid sequence which has higher affinity for said second test protein than the original sequence. The nucleotide sequence of said C-terminal region may be replaced by a nucleotide sequence encoding the C-terminal region of AVPR2, AGTRLI, GRPR, F2RL1, CXCR2/IL-8B, CCR4, or GRPR.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 5a and 5b illustrate results of an assay which shows that two molecules can be studied simultaneously.

FIG. 10 shows the results of additional experiments where a different transcription factor, and a different cell line, were used.

DETAILED DESCRIPTION OF PREFERRED EMBODIMENTS

The present invention relates to methods for determining if a substance of interest modulates interaction of a first test protein, such as a membrane bound protein, like a receptor, e.g., a transmembrane receptor, with a second test protein, like a member of the arrestin family. The methodology involves cotransforming or cotransfecting a cell, which may be prokaryotic or eukaryotic, with two constructs. The first construct includes, a sequence encoding (i) the first test protein, such as a transmembrane receptor, (ii) a cleavage site for a protease, and (iii) a sequence encoding a protein which activates a reporter gene. The second construct includes, (i) a sequence which encodes a second test protein whose interaction with the first test protein is measured and/or determined, and (ii) a nucleotide sequence which encodes a protease or a portion of a protease sufficient to act on the cleavage site that is part of the first construct. In especially preferred embodiments, these constructs become stably integrated into the cells.

Figure 1:
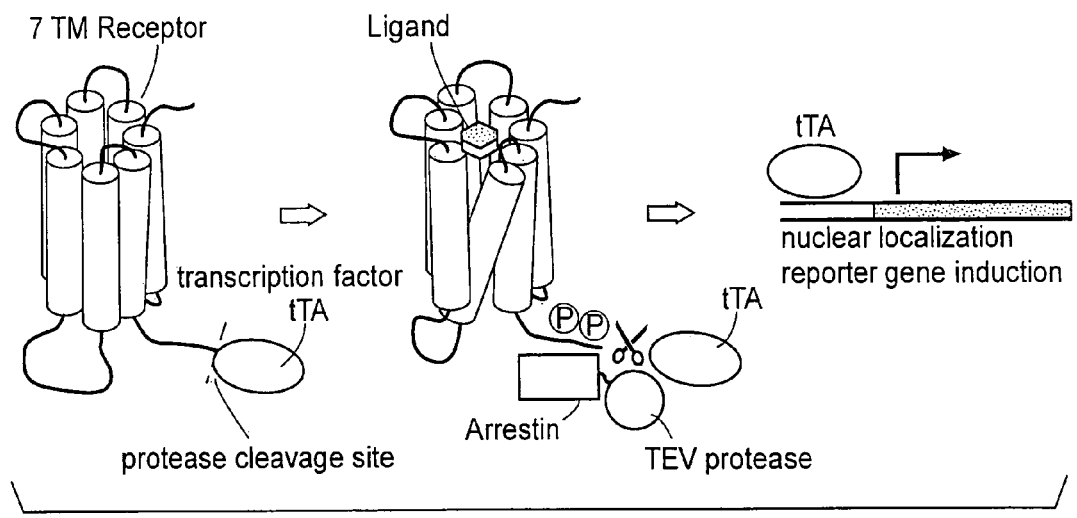
FIG. 1 shows the conceptual underpinnings of the invention, pictorially, using ligand-receptor binding as an example.

The features of an embodiment of the invention are shown, pictorially, in FIG. 1. In brief, first, standard techniques are employed to fuse DNA encoding a transcription factor to DNA encoding a first test protein, such as a transmembrane receptor molecule, being studied. This fusion is accompanied by the inclusion of a recognition and cleavage site for a protease not expressed endogenously by the host cell being used in the experiments.

DNA encoding this first fusion protein is introduced into and is expressed by a cell which also contains a reporter gene sequence, under the control of a promoter element which is dependent upon the transcription factor fused to the first test protein, e.g., the receptor. If the exogenous protease is not present, the transcription factor remains tethered to the first test protein and is unable to enter the nucleus to stimulate expression of the reporter gene.

Recombinant techniques can also be used to produce a second fusion protein. In the depicted embodiment, DNA encoding a member of the arrestin family is fused to a DNA molecule encoding the exogenous protease, resulting in a second fusion protein containing the second test protein, i.e., the arrestin family member.

An assay is then carried out wherein the second fusion protein is expressed, together with the first fusion protein, and a test compound is contacted to the cells, preferably for a specific length of time. If the test compound modulates interaction of the two test proteins, e.g., by stimulating, promoting or enhancing the association of the first and second test proteins, this leads to release of the transcription factor, which in turn moves to the nucleus, and provokes expression of the reporter gene. The activity of the reporter gene is measured.

In an alternative system, the two test proteins may interact in the absence of the test compound, and the test compound may cause the two test proteins to dissociate, lessen or inhibit their interaction. In such a case, the level of free, functionally active transcription factor in the cell decreases in the presence of the test compound, leading to a decrease in proteolysis, and a measurable decrease in the activity of the reporter gene.

In the depicted embodiment, the arrestin protein, which is the second test protein, binds to the receptor in the presence of an agonist; however, it is to be understood that since receptors are but one type of protein, the assay is not dependent upon the use of receptor molecules, nor is agonist binding the only interaction capable of being involved. Any protein will suffice, although the interest in transmembrane proteins is clear. Further, agonist binding to a receptor is not the only type of binding which can be assayed. One can determine antagonists, per se and also determine the relative strengths of different antagonists and/or agonists in accordance with the invention.

Other details of the invention, include specific methods and technology for making and using the subject matter thereof, are described below.

I. Expression Constructs and Transformation

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis, et al., Molecular Cloning, A Laboratory Manual (Cold Spring Harbor, 1990) and Ausubel, et al., 1994, Current Protocols In Molecular Biology (John Wiley & Sons, 1996), both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleotide sequences that serve other functions as well and are described infra.

In certain embodiments, a plasmid vector is contemplated for use in cloning and gene transfer. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Many prokaryotic vectors can also be used to transform eukaryotic host cells. However, it may be desirable to select vectors that have been modified for the specific purpose of expressing proteins in eukaryotic host cells. Expression systems have been designed for regulated and/or high level expression in such cells. For example, the insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACKPACK™ BACULOVIRUS EXPRESSION SYSTEM FROM CLONTECH®.

Other examples of expression systems include STRATAGENEO'S COMPLETE CONTROL™ Inducible Mammalian Expression System, which involves a synthetic ecdysone-inducible receptor, or its pET Expression System, an E.coli expression system. Another example of an inducible expression system is available from INVITROGEN, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Regulatory Signals

The construct may contain additional 5' and/or 3' elements, such as promoters, poly A sequences, and so forth. The elements may be derived from the host cell, i.e., homologous to the host, or they may be derived from distinct source, i.e., heterologous.

"promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid molecule, as may be obtained by isolating the 5' non-coding sequences located upstream of the coding segment and/or exon. Such a promoter can be referred to as "endogenous." Similarly, an enhancer may be one naturally associated with a nucleic acid molecule, located either downstream or upstream of that sequence. Alternatively, certain advantages will be gained by positioning the coding nucleic acid segment under the control of a recombinant or heterologous promoter, which refers to a promoter that is not normally associated with a nucleic acid molecule in its natural environment. A recombinant or heterologous enhancer refers also to an enhancer not normally associated with a nucleic acid molecule in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook, et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, Nature, 334: 320–325 (1988)). IRES elements from two members of the picornavirus family (polio and encephalomyocarditis) have been described (Pelletier and Sonenberg, supra), as well an IRES from a mammalian message (Macejak and Sarnow, Nature, 353:90–94 (1991))1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Other Vector Sequence Elements p Vectors can include a multiple cloning site (MCS), which is a nucleic acid region that contains multiple restriction enzyme sites, any of which can be used in conjunction with standard recombinant technology to digest the vector (see, for example, Carbonelli, et al., FEMS Microbiol. Lett., 172(1):75–82 (1999), Levenson, et al., Hum. Gene Ther. 9(8):1233–1236 (1998), and Cocea, Biotechniques, 23(5):814–816 (1997)), incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler, et al., 1997, herein incorporated by reference).

The vectors or constructs of the present invention will generally comprise at least one termination signal. A "termination signal" or "terminator" comprises a DNA sequence involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 adenosine residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not being limited to, for example, the termination sequences of genes, such as the bovine growth hormone terminator, viral termination sequences, such as the SV40 terminator. In certain embodiments, the termination signal may be a lack of transcribable or translatable sequence, such as an untranslatable/untranscribable sequence due to a sequence truncation.

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, both of which are convenient, readily available, and known to function well in various target cells. Polyadenylation may increase the stability of the transcript or may facilitate cytoplasmic transport.

In order to propagate a vector in a host cell, it may contain one or more origins of replication (often termed "ori"), sites, which are specific nucleotide sequences at which replication is initiated. Alternatively, an autonomously replicating sequence (ARS) can be employed if the host cell is yeast.

Transformation Methodology

Suitable methods for nucleic acid delivery for use with the current invention are believed to include virtually any method by which a nucleic acid molecule (e.g., DNA) can be introduced into a cell as described herein or as would be known to one of ordinary skill in the art. Such methods include, but are not limited to, direct delivery of DNA such as by ex vivo transfection (Wilson, et al., Science, 244: 1344–1346 (1989), Nabel et al, Science, 244:1342–1344 (1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, J. Cell Biol., 101(3):1094–1099 (1985); U.S. Pat. No. 5,789, 215, incorporated herein by reference); by electroporation (U.S. Pat. No. 5,384,253, incorporated herein by reference; Tur-Kaspa, et al., Mol. Cell Biol., 6:716–718 (1986); Potter, et al., Proc. Natl. Acad. Sci. USA, 81:7161–7165 (1984); by calcium phosphate precipitation (Graham and Van Der Eb, Virology, 52:456–467 (1973); Chen and Okayama, Mol. Cell Biol., 7(8):2745–2752 (1987); Rippe, et al., Mol. Cell Biol., 10:689–695 (1990); by using DEAE-dextran followed by polyethylene glycol (Gopal, Mol. Cell Biol., 5:1188–190 (1985); by direct sonic loading (Fechheimer, et al, Proc. Natl. Acad. Sci. USA, 89(17):8463–8467 (1987); by liposome mediated transfection (Nicolau and Sene, Biochem. & Biophys. Acta., 721:185–190 (1982); Fraley, et al, Proc. Natl. Acad. Sci. USA, 76:3348–3352 (1979); Nicolau, et al., Meth. Enzym., 149:157–176 (1987); Wong, et al., Gene, 10:879–894 (1980); Kaneda, et al., Science, 243:375–378 (1989); Kato, et al., J. Biol. Chem., 266:3361–3364 (1991) and receptor-mediated transfection (Wu and Wu, J. Biol. Chem., 262:4429–4432 (1987); Wu and Wu, 1988); by PEG-mediated transformation of protoplasts (Omirulleh, et al., Plant Mol. Biol., 21(3):415–428 (1987); U.S. Pat. Nos. 4,684,611 and 4,952,500, each incorporated herein by reference); by desiccation/inhibition-mediated DNA uptake (Potrykus, et al. Mol. Gen. Genet., 199(2):169–177 (1985), and any combination of such methods.

II. Components of the Assay System

As with the method described herein, the products which are features of the invention have preferred embodiments. For example, in the "three part construct," i.e., that contain sequences encoding a test protein, the cleavage site, and the activator protein, the test protein is preferably a membrane bound protein, such as a transmembrane receptor, e.g., a member of the GPCR family. These sequences can be modified so that the C terminus of the proteins they encode have better and stronger interactions with the second protein. The modifications can include, e.g., replacing a C-terminal encoding sequence of the test protein, such as a GPCR, with the C terminal coding region for AVPR2, AGTRLI, GRPR, F2PLI, CCR4, CXCR2/IL-8, CCR4, or GRPR, all of which are defined supra.

The protein which activates the reporter gene may be a protein which acts within the nucleus, like a transcription factor (e.g., tTA, GAL4, etc.), or it may be a molecule that sets a cascade of reactions in motion, leading to an intranuclear reaction by another protein. The skilled artisan will be well versed in such cascades.

The second construct, as described supra, includes a region which encodes a protein that interacts with the first protein, leading to some measurable phenomenon. The protein may be an activator, an inhibitor, or, more, generically, a "modulator" of the first protein. Members of the arrestin family are preferred, especially when the first protein is a GPCR, but other protein encoding sequences may be used, especially when the first protein is not a GPCR. The second part of these two part constructs encodes the protease, or portion of a protease, which acts to remove the activating molecule from the fusion protein encoded by the first construct.

However, these preferred embodiments do not limit the invention, as discussed in the following additional embodiments.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. The host cells generally will have been engineered to express a screenable or selectable marker which is activated by the transcription factor that is part of a fusion protein, along with the first test protein.

In the context of expressing a heterologous nucleic acid sequence, "host cell" refers to a prokaryotic or eukaryotic cell that is capable of replicating a vector and/or expressing a heterologous gene encoded by a vector. When host cells are "transfected" or "transformed" with nucleic acid molecules, they are referred to as "engineered" or "recombinant" cells or host cells, e.g., a cell into which an exogenous nucleic acid sequence, such as, for example, a vector, has been introduced. Therefore, recombinant cells are distinguishable from naturally-occurring cells which do not contain a recombinantly introduced nucleic acid.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expressioninclude, but are not limited to, bacteria, such as *E. coil* (e.g., *E. coli* strain RR1, *E. coil* LE392, *E. coil* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis;* and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, COS, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Test Proteins

The present invention contemplates the use of any two proteins for which a physical interaction is known or suspected. The proteins will exist as fusions proteins, a first test protein fused to a transcription factor, and the second test protein fused to a protease that recognizes a cleavage site in the first fusion protein, cleavage of which releases the transcription factor. The only requirements for the test proteins/fusions are (a) that the first test protein cannot localize to the nucleus prior to cleavage, and (b) that the protease must remain active following both fusion to the second test protein and binding of the first test protein to the second test protein.

With respect to the first construct, the first test protein may be, e.g., a naturally membrane bound protein, or one which has been engineered to become membrane bound, via standard techniques. The first test protein may be, e.g., a transmembrane receptor such as any of the GPCRs, or any other transmembrane receptor of interest, including, but not being limited to, receptor tyrosine kinases, receptor serine threonine kinases, cytokine receptors, and so forth. Further, as it is well known that portions of proteins, will function in the same manner as the full length first test protein, such active portions of a first test protein are encompassed by the definition of protein herein.

As will be evident to the skilled artisan, the present invention may be used to assay for interaction with any protein, and is not limited in its scope to assaying membrane bound receptor, like the GPCRs. For example, the activity of other classes of transmembrane receptors, including but not limited to: receptor tyrosine kinases (RTKs), such as IGF1R, such as the epidermal growth factor receptor (EGFR), ErbB2/HER2/Neu or related RTKs; receptor serine/threonine kinases, such as Transforming Growth Factor-beta (TGFβ), activin, or Bone Morphogenetic Protein (BMP) receptors; cytokine receptors, such as receptors for the interferon family for interleukin, erythropoietin, G-CSF, GM-CSF, tumor necrosis factor (TNF) and leptin receptors; and other receptors, which are not necessarily normally membrane bound, such as estrogen receptor 1 (ESR1), and estrogen receptor 2 (ESR2). In each case, the method involves transfecting a cell with a modified receptor construct that directs the expression of a chimeric protein containing the receptor of interest, to which is appended, a protease cleavage site followed by a nucleic acid molecule encoding a transcription factor. The cell is co-transfected with a second construct that directs the expression of a chimeric protein consisting of an interacting protein fused, to the protease that recognizes and cleaves the site described supra. In the case of RTKs, such as the EGFR, this interacting protein may consist of a SH2 (Src homology domain 2) containing protein or portion thereof, such as phospholipase C (PLC) or Src homology 2 domain containing transforming protein 1 (SHC1). In the case of receptor serine/threonine kinases, such as TGFβ, activin, BMP receptors, this interacting protein may be a Smad protein or portion thereof. In the case of cytokine receptors, such as interferon-α/β or interferon-γ gamma receptors, this interacting protein may be a signal transducer and activator of transcription (STAT) protein such as, but not being limited to, Stat1, Stat2; Janus kinase (JAK) proteins Jak1, Jak2, or Tyk2; or portions thereof. In each case, the transfected cell contains a reporter gene that is regulated by the transcription factor fused to the receptor. An assay is then performed in which the transfected cells are treated with a test compound for a specific period and the reporter gene activity is measured at the end of the test period. If the test compound activates the receptor of interest, interactions between the receptor of interest and the interacting protein are stimulated, leading to cleavage of the protease site and release of the fused transcription factor, which is in turn measurable as an increase in reporter gene activity.

Other possible test protein pairs include antibody-ligands, enzyme-substrates, dimerizing proteins, components of signal transduction cascades, and other protein pairs well known to the art.

Reporters

The protein which activates a reporter gene may be any protein having an impact on a gene, expression or lack thereof which leads to a detectable signal. Typical protein reporters include enzymes such as chloramphenicol acetyl transferase (CAT), β-glucuronidase (GUS) or β-galactosidase. Also contemplated are fluorescent and chemilluminescent proteins such as green fluorescent protein, red fluorescent protein, cyan fluorescent protein luciferase, beta lactamase, and alkaline phosphatase.

Transcriptions Factors and Repressors

In accordance with the present invention, transcription factors are used to activate expression of a reporter gene in an engineered host cell. Transcription factors are typically classified according to the structure of their DNA-binding domain, which are generally (a) zinc fingers, (b) helix-turn-helix, (c) leucine zipper, (d) helix-loop-helix, or (e) high mobility groups. The activator domains of transcription factors interact with the components of the transcriptional apparatus (RNA polymerase) and with other regulatory proteins, thereby affecting the efficiency of DNA binding.

The Rel/Nuclear Factor kB (NF-kB) and Activating Protein-1 (AP-1) are among the most studied transcription factor families. They have been identified as important components of signal transduction pathways leading to pathological outcomes such as inflammation and tumorogenesis. Other transcription factor families include the heat shock/E2F family, POU family and the ATF family. Particular transcription factors, such as tTA and GAL4, are contemplated for use in accordance with the present invention.

Though transcription factors are one class of molecules that can be used, the assays may be modified to accept the use of transcriptional repressor molecules, where the measurable signal is downregulation of a signal generator, or even cell death.

Proteases and Cleavage Sites

Proteases are well characterized enzymes that cleave other proteins at a particular site. One family, the Ser/Thr proteases, cleave at serine and threonine residues. Other proteases include cysteine or thiol proteases, aspartic proteases, metalloproteinases, aminopeptidases, di & tripeptidases, carboxypeptidases, and peptidyl peptidases. The choice of these is left to the skilled artisan and certainly need not be limited to the molecules described herein. It is well known that enzymes have catalytic domains and these can be used in place of full length proteases. Such are encompassed by the invention as well. A specific embodiment is the tobacco etch virus nuclear inclusion A protease, or an active portion thereof. Other specific cleavage sites for proteases may also be used, as will be clear to the skilled artisan.

Modification of Test Proteins

The first test protein may be modified to enhance its binding to the interacting protein in this assay. For example, it is known that certain GPCRs bind arrestins more stably or with greater affinity upon ligand stimulation and this enhanced interaction is mediated by discrete domains, e.g., clusters of serine and threonine residues in the C-terminal tail (Oakley, et al, *J. Biol. Chem.*, 274:32248–32257, 1999 and Oakley, et al., *J. Biol. Chem.*, 276:19452–19460, 2001). Using this as an example, it is clear that the receptor encoding sequence itself may be modified, so as to increase the affinity of the membrane bound protein, such as the receptor, with the protein to which it binds. Exemplary of such modifications are modifications of the C-terminal region of the membrane bound protein, e.g., receptor, such as those described supra, which involve replacing a portion of it with a corresponding region of another receptor, which has higher affinity for the binding protein, but does not impact the receptor function. Examples 16 and 20, supra, show embodiments of this feature of the invention.

In addition, the second test protein may be modified to enhance its interaction with the first test protein. For example, the assay may incorporate point mutants, truncations or other variants of the second test protein, e.g., arrestin that are known to bind agonist-occupied GPCRs more stably or in a phosphorylation-independent manner (Kovoor, et al., *J. Biol. Chem.*, 274:6831–6834, 1999).

III. Assay Formats

As discussed above, the present invention, in one embodiment, offers a straightforward way to assess the interaction of two test proteins when expressed in the same cell. A first construct, as described supra, comprises a sequence encoding a first protein, concatenated to a sequence encoding a cleavage site for a protease or protease portion, which is itself concatenated to a sequence encoding a reporter gene activator. By "concatenated" is meant that the sequences described are fused to produce a single, intact open reading frame, which may be translated into a single polypeptide which contains all the elements. These may, but need not be, separated by additional nucleotide sequences which may or may not encode additional proteins or peptides. A second construct inserted into the recombinant cells is also as described supra, i.e., it contains both a sequence encoding a second protein, and the protease or protease portion. Together, these elements constitute the basic assay format when combined with a candidate agent whose effect on target protein interaction is sought.

However, the invention may also be used to assay more than one membrane bound protein, such as a receptor, simultaneously by employing different reporter genes, each of which is stimulated by the activation of a protein, such as the classes of proteins described herein. For example, this may be accomplished by mixing cells transfected with different receptor constructs and different reporter genes, or by fusing different transcription factors to each test receptor, and measuring the activity of each reporter gene upon treatment with the test compound. For example, it may be desirable to determine if a molecule of interest activates a first receptor and also determine if side effects should be expected as a result of interaction with a second receptor. In such a case one may, e.g., involve a first cell line encoding a first receptor and a first reporter, such as lacZ, and a second cell line encoding a second receptor and a second reporter, such as GFP. Preferred embodiments of such a system are seen in Examples 17 and 18. One would mix the two cell lines, add the compound of interest, and look for a positive effect on one, with no effect on the other.

It is contemplated that the invention relates both to assays where a single pair of interacting test proteins is examined, but more preferably, what will be referred to herein as "multiplex" assays are used. Such assays may be carried out in various ways, but in all cases, more than one pair of test proteins is tested simultaneously. This may be accomplished, e.g., by providing more than one sample of cells, each of which has been transformed or transfected, to test each interacting pair of proteins. The different transformed cells may be combined, and tested simultaneously, in one receptacle, or each different type of transformant may be placed in a different well, and then tested.

The cells used for the multiplex assays described herein may be, but need not be, the same. Similarly, the reporter system used may, but need not be, the same in each sample. After the sample or samples are placed in receptacles, such as wells of a microarray, one or more compounds may be screened against the plurality of interacting protein pairs set out in the receptacles.

The fusion proteins expressed by the constructs are also a feature of the invention. Other aspects of the invention which will be clear to the artisan, are antibodies which can identify the fusion proteins as well as various protein based assays for determining the presence of the protein, as well as hybridization assays, such as assays based on PCR, which determine expression of the gene.

IV. Kits

Any of the compositions described herein may be comprised in a kit. The kits will thus comprise, in suitable container means for the vectors or cells of the present invention, and any additional agents that can be used in accordance with the present invention.

The kits may comprise a suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

V. Examples

Specific embodiments describing the invention will be seen in the examples which follow, but the invention should not be deemed as limited thereto.

EXAMPLE 1

A fusion construct was created, using DNA encoding human β2 adrenergic receptor, referred to hereafter as "ADRB2", in accordance with standard nomenclature. Its nucleotide sequence can be found at GenBank, under Accession Number NM_000024 (SEQ ID NO: 1). The tetracycline controlled transactivator tTA, described by Gossen, et al., *Proc. Natl. Acad. Sci. USA*, 87:5547–5551 (1992), incorporated by reference, was also used. A sequence encoding the recognition and cleavage site for tobacco etch virus nuclear inclusion A protease, described by Parks, et al., *Anal. Biochem.*, 216:413–417 (1994), incorporated by reference, is inserted between these sequences in the fusion coding gene. The CMV promoter region was placed upstream of the ADRB2 coding region, and a poly A sequence was placed downstream of the tTA region.

A fusion construct was prepared by first generating a form of ADRB2 which lacked internal BamHI and BglII restriction sites. Further, the endogenous stop codon was replaced with a unique BantHI site.

Overlapping PCR was used to do this. To elaborate, a 5' portion of the coding region was amplified with:

```
gattgaagat ctgccttctt gctggc,      (SEQ ID NO: 2)

and gcagaacttg aagacctgc ggagtcc,      (SEQ ID NO: 3)
``` while a 3' portion of the coding region was amplified with:

```
ggactccgca ggtcttccaa gttctgc,     (SEQ ID NO: 4)

and ttcggatcct agcagtgagt catttgt.     (SEQ ID NO: 5)
```

The resulting PCR products have 27 nucleotides of overlapping sequence and were purified via standard agarose gel electrophoresis. These were mixed together, and amplified with SEQ ID NO: 2, and SEQ ID NO: 5.

PCR was also used to modify the coding region of tTA so that the endogenous start codon was replaced with a TEV NIa-Pro cleavage site. The cleavage site, defined by the seven amino acid sequence ENLYFQS (SEQ ID NO: 6), is taught by Parks, et al., *Anal. Biochem.*, 216:413–417 (1994), incorporated by reference. The seventh amino acid is known as P1' position, and replacing it with other amino acids is known to reduce the efficiency of cleavage by TEV NIa-Pro. See Kapust, et al., *Biochem. Biophys. Res. Commun.*, 294: 949–955 (2002).

Variants where the seventh amino acid was changed to Tyr, and where it was changed to Leu, were produced. These resulted in intermediate and low efficiency cleavage sites, as compared to the natural high efficiency site.

A DNA sequence encoding the natural high efficiency site was added to the tTA coding region in two steps. Briefly, BamHI and XbaI restriction sites were added to the 5' end and a XhoI restriction site was added to the 3' end of the tTA coding region by PCR with

```
ccggatcctc tagattagat aaaagtaaag tg   (SEQ ID NO: 7)

and gactcgagct agcagtatcc tcgcgccccc      (SEQ ID NO: 8)
taccc,
``` and the TEV NIa-Pro cleavage site was added to the 5' end by ligating an oligonucleotide with the sequence

```
     gagaacctgt acttccag         (SEQ ID NO: 9)
``` between the BamHI and XbaI sites.

This DNA sequence was modified to encode the intermediate and low efficiency cleavage sites by PCR using:

```
ggatccgaga acctgtactt ccagtacaga   (SEQ ID NO: 10)
tta, and ctcgagagat cctcgcgccc cctacccacc.  (SEQ ID NO: 11)
for ENLYFQY,                       (SEQ ID NO: 12)

and ggatccgaga acctgtactt ccagctaaga   (SEQ ID NO: 13)
tta, and ctcgagagat cctcgcgccc cctacccacc   (SEQ ID NO: 11)
for ENLYFQL.                       (SEQ ID NO: 14)
```

These PCR steps also introduced a BamHI restriction site 5' to the sequence encoding each cleavage site, and an XhoI restriction site 3' to tTA stop codon.

The thus modified ADRB2 coding region was digested with PstI, which cuts at nucleotide position 260 in the coding region, and BamHI. This 3' fragment was ligated with the three variants of tTA modified with the TEV NIa-Pro cleavage sites, that had been digested with BamHI and XhoI, and the resulting complexes were cloned into pBlueScript II, which had been digested with PstI and XhoI.

A NotI restriction site was introduced 5' to the start codon of the ADRB2 coding region, again via PCR, using

```
gcggccgcca ccatgaacgg taccgaaggc   (SEQ ID NO: 15)
cca, and ctggtgggtg gcccggtacc a.           (SEQ ID NO: 16)
```

The 5' fragment of modified ADRB2 coding region was isolated, via digestion with NotI and PstI and was ligated into each of the constructs of the 3' fragment of ADRB2-TEV-NIa-Pro-cleavage site tTA fusions that had been digested previously, to produce three, full length constructs encoding fusion proteins.

Each construct was digested with NotI and XhoI, and was then inserted into the commercially available expression vector pcDNA 3, digested with NotI and XhoI.

EXAMPLE 2

A second construct was also made, whereby the coding sequence for "βarrestin 2 or ARRB2" hereafter (GenBank, NM_004313) (SEQ ID NO: 17), was ligated to the catalytic domain of the TEV NIa protease (i.e., amino acids 189–424 of mature NIa protease, residues 2040–2279) in the TEV protein. To do this, a DNA sequence encoding ARRB2 was modified, so as to add a BamHI restriction site to its 5' end. Further, the sequence was modified to replace the endogenous stop codon with a BamHI site. The oligonucleotides

```
caggatcctc tggaatgggg gagaaacccg    (SEQ ID NO: 18)
ggacc,
``` and

```
ggatccgcag agttgatcat catagtcgtc    (SEQ ID NO: 19)
``` were used. The resulting PCR product was cloned into the commercially available vector pGEM-T EASY (Promega). The multiple cloning site of the pGEM-T EASY vector includes an EcoRI site 5' to the start codon of ARRB2.

The TEV NIa-Pro coding region was then modified to replace the endogenous start codon with a BglII site, and to insert at the 3' end a sequence which encodes influenza hemagluttinin epitope YPYDVPDYA (SEQ ID NO: 20) in accordance with Kolodziej, et al., *Meth. Enzymol.*, 194: 508–519 (1991), followed by a stop codon, and a NotI restriction site. This was accomplished via PCR, using

```
agatctagct tgtttaaggg accacgtg,    (SEQ ID NO: 21)
``` and

```
gcggccgctc aagcgtaatc tggaacatca    (SEQ ID NO: 22)
tatgggtacg agtacaccaa ttcattcatg
ag.
```

The resulting, modified ARRB2 coding region was digested with EcoRI and BamHI, while the modified TEV coding region was cleaved with BglII and NotI. Both fragments were ligated into a commercially available pcDNA3 expression vector, digested with EcoRI and NotI.

EXAMPLE 3

Plasmids encoding ADRB2-TEV-NIa-Pro cleavage site-tTA and the ARRB2-TEV-NIa protease fusion proteins were transfected into HEK-293T cells, and into "clone 41," which is a derivative of HEK-293T, that has a stably integrated β-galactosidase gene under control of a tTA dependent promoter. About $5 \times 10^4$ cells were plated in each well of a 24 well plate, in DMEM medium supplemented with 10% fetal bovine serum, 2mM L-glutamine, 100 units/ml penicillin, 100 μg/ml G418, and 5 μg/ml purimycin. Cells were grown to reach 50% confluency the next day, and were then transfected, using 0.4 μg plasmid DNA, and 2 μl Fugene (a proprietary transfection reagent containing lipids and other material). The mix was combined in 100 μl of DMEM medium, and incubated for 15 minutes at room temperature prior to adding cells. Transfected cells were incubated for 8–20 hours before testing by adding drugs which are known agonists for the receptor, and then 16–24 hours after drug addition.

EXAMPLE 4

The levels of β-galactosidase activity in the cells were first measured by staining the cells with a chromogenic substance, i.e., "X-gal," as taught by MacGregor, et al., *Somat. Cell Mol. Genet.*, 13:253–265 (1987), incorporated by reference. Following culture, cells were washed, twice, in D-PBS with calcium and magnesium, fixed for 5 minutes in 4% paraformaldehyde, and then washed two additional times with D-PBS, calcium and magnesium, for 10 minutes each time. Fixed cells were incubated with 5 mM potassium ferricyanide, 5 mM potassium ferrocyanide, 2 mM $MgCl_2$, 0.1% X-Gal, that had been prepared from a 1:40 dilution of 4% X-Gal stock in dimethylformamide, in D-PBS with calcium and magnesium.

The reaction was incubated in the dark at room temperature for from 3–4 hours, to overnight. Substrate solution was removed, and cells were mounted under glass coverslips with mowiol mounting medium (10% mowiol, 0.1% 1.4-diazabicyclo[2.2.2]octane, 24% glycerol).

The results indicated that cells transfected with either the ADRB2-TEV-NIa-Pro cleavage site-tTA plasmid alone or the ARRB2-TEV-NIa protease plasmid alone did not express β-galactosidase. A small fraction of cells transfected with both plasmids did express β-galactosidase, probably due to basal levels of interaction between unstimulated ADRB2 and ARRB2. About 3–5 fold more cells expressed the reporter gene after treatment with either 10 μM isoproterenol, or 10 μM epinephrine, both of which are ADRB2 agonists.

When the cells were pretreated for 5 minutes with the ADRB2 antagonist alprenolol (10 μM), the agonist induced increase in β-galactosidase expressing cells was blocked, and treatment with alprenolol alone had no apparent effect.

These results show that one can link agonist binding and GPCR stimulation to transcriptional activation of a reporter gene.

EXAMPLE 5

A set of experiments were carried out in order to quantify the level of reporter gene activity in the cells more precisely and to maximize the signal-to-background ratio of the assay. This was accomplished by measuring the level of reporter gene induction using a commercially available chemiluminescence assay for β-galactosidase activity. Clone 41 cells were transfected with the ADRB2-tTA fusion constructs, containing either the high, medium or low efficiency cleavage sites, and the ARRB2-TEV-NIa protease expression plasmid described supra. Cells were either untreated or treated with 1 μM isoproterenol 20 hours after the transfection, and the luminescence assay was carried out 24 hours after the drug addition. In brief, following cell culture, the medium was removed, and 50 μl of lysis buffer (100 mM potassium phosphate, pH7.8, 0.2% Triton X-100) was added to each well. The cells were lysed via incubation for 5 minutes, at room temperature, with mild agitation. Lysates were collected and analyzed via commercially available products.

In all cases, treatment with agonist increased levels of β-galactosidase activity. However, the background level of reporter gene activity in untreated cells was lowest with the low efficiency cleavage site, relative to the medium and high efficiency sites. Further, agonist treatment resulted in a 4.8-fold stimulation of reporter gene activity in cells transfected with the low efficiency cleavage site, compared to 2.8-fold for the medium efficiency cleavage site and 1.2-fold for the high efficiency cleavage site. Thus, the highest signal-to-background ratio is obtained by using the low efficiency protease cleavage site.

EXAMPLE 6

These experiments were designed to verify that the agonist stimulated increase in reporter gene expression is dependent on binding and activation of the receptor by the agonist.

To do this, variants of the ADRB2-tTA fusion constructs were generated following the protocols supra, except each contained a mutant form of the receptor with a single amino acid change from D to S at position 113, which results in a greatly reduced affinity for the agonist isoproterenol. See Strader, et al., *J. Biol. Chem.*, 266:5–8 (1991). Three forms of the mutant receptor-tTA fusion construct with each of the different cleavage sites were formed.

The levels of β-galactosidase activity were measured in clone 41 cells co-transfected with the ADRB2-tTA fusion constructs containing the D113S point mutation and the ARRB2-TEV-NIa protease expression plasmid described previously. The activity tests were carried out exactly as described, supra. The results indicated that the agonist isoproterenol did not stimulate reporter gene expression in cells expressing the mutant ADRB2-tTA fusion contructs.

EXAMPLE 7

These experiments were designed to examine whether the agonist stimulated increase in reporter gene expression is dependent on fusion of TEV NIa-Pro to ARRB2.

To do this, the levels of β-galactosidase activity were measured in clone 41 cells co-transfected with the ADRB2-tTA fusion construct containing the low efficiency cleavage site and either the ARRB2-TEV-NIa protease expression plasmid described supra, or a control TEV-NIa protease fusion to the SH2 domain of phospholipase C. The activity tests were carried out exactly as described, supra. The results indicated that agonist-stimulated increase in reporter gene expression was detected only when the TEV protease was fused to ARRB2 and not when fused to an unrelated polypeptide.

EXAMPLE 8

These experiments were designed to determine if gene expression is induced selectively by agonists of the target receptor, or if it can be stimulated by other molecules.

ATP is an agonist for G protein coupled receptors P2Y1 and P2Y2, which are expressed endogenously by HEK-293T cells.

Experiments were carried out using clone 41 cells which were cotransfected with the ADRB2-tTA fusion construct containing the low efficiency cleavage site and the arrestin-TEV-NIa protease fusion as described supra, which were treated with isoproterenol, ATP, or untreated. The assays were carried out as described, supra.

The results indicated that induction of reporter gene activity was specific to activation of target receptor. Stimulation of another GPCR pathway was irrelevant.

EXAMPLE 9

Figure 2A:
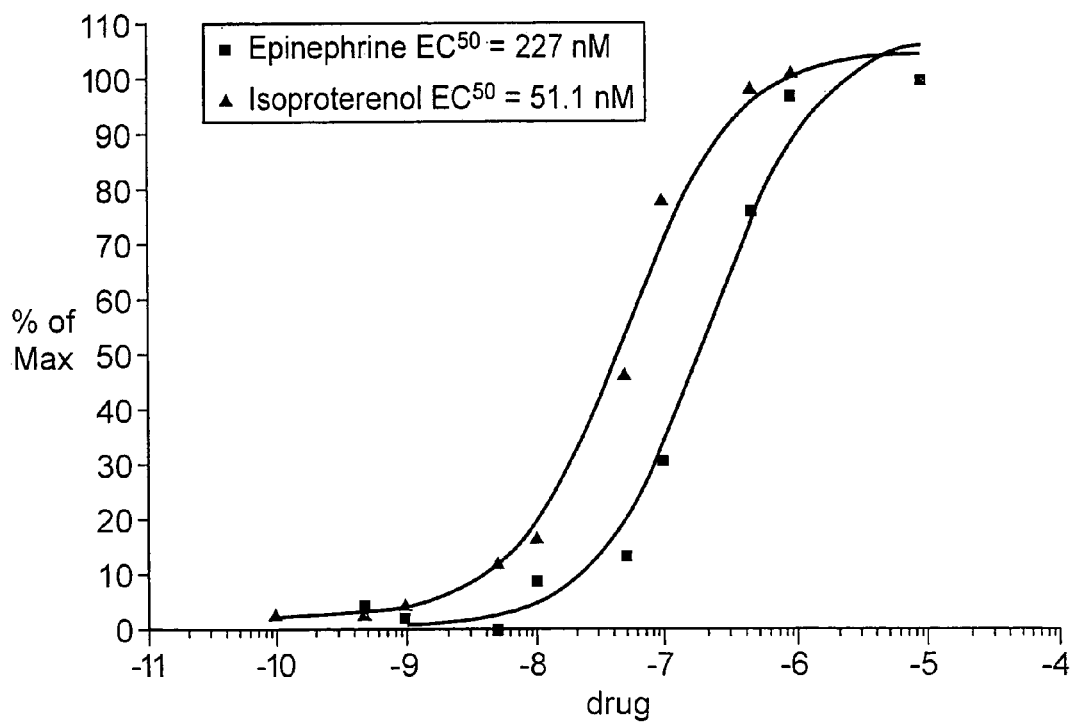
FIGS. 2a and 2b show that the response of targets in assays in accordance with the invention is dose dependent, both for agonists and antagonists.

A set of experiments were carried out using clone 41 cells which were cotransfected with the ADRB2-tTA fusion construct containing the low efficiency cleavage site and the ARRB2-TEV-NIa protease fusion as described supra, which were treated with varying amounts of one of the adrenergic receptor agonists isoproterenol and epinephrine. The assays were carried out as described, supra. The results presented in FIG. 2a show a dose-response curve for the stimulation of reporter gene expression by these two ligands. Each point represents the mean value obtained from three experiments.

Figure 2B:
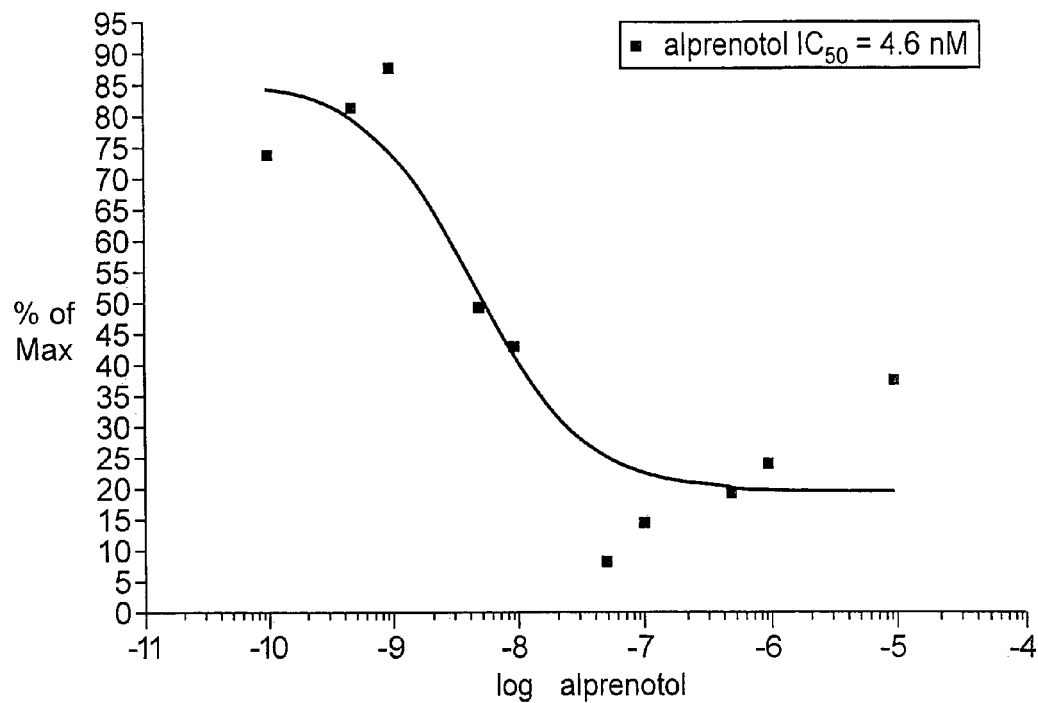

A set of experiments were carried out as described supra, in which the co-transfected clone 41 cells were pretreated with varying concentrations of the adrenergic receptor antagonist alprenolol for 15 minutes, followed by treatment with 1 μM epinephrine. The results shown in FIG. 2b indicate a dose-inhibition curve for this antagonist.

EXAMPLE 10

A similar set of constructs were made to establish an assay for the G protein coupled arginine vasopressin receptor 2 (AVPR2). The AVPR2 coding region (Genbank Accession Number: NM_000054) (SEQ ID NO: 23) was modified to place an EcoRI site at the 5' end and replace the stop codon with a BamHI site using PCR with the primers

```
gaattcatgc tcatggcgtc caccac      (SEQ ID NO: 24)
``` and

```
ggatcccgat gaagtgtcct tggccag.    (SEQ ID NO: 25)
```

The modified AVPR2 coding region was ligated into the three ADRB2- tTA constructs described supra, which had been cut with EcoRI and BamHI. This replaced the entire coding sequence of the ADRB2 with the coding sequence of AVPR2.

Figure 3:
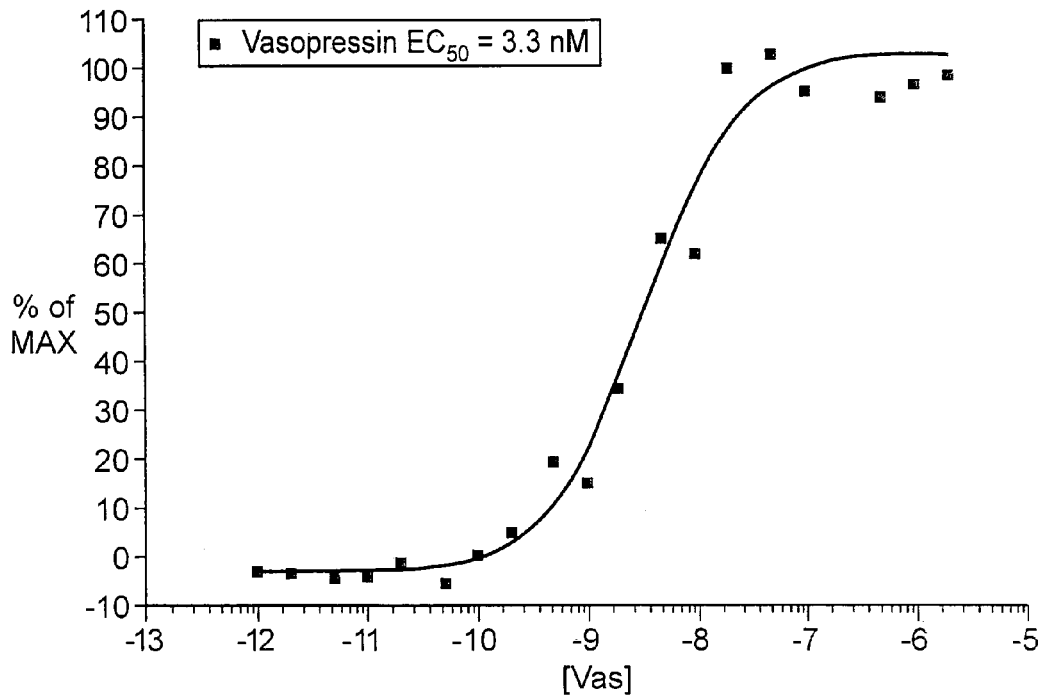
FIG. 3 shows that a dose response curve results with a different target and a different agonist as well.

Clone 41 cells were co-transfected with the AVPR2-tTA fusion construct containing the low efficiency cleavage site and the ARRB2-TEV-NIa protease fusion described supra, and assays were carried out using varying concentrations (1 pM to 2 μM) of [Arg8] vasopressin, an agonist for AVPR2. The data, presented in FIG. 3, shows a dose-response curve for this agonist, with an EC50 of 3.3 nM, which agrees with previously published data (Oakley, R., et. al., *Assay and Drug Development Technologies*, 1:21–30, (2002)). The maximal response resulted in an approximately 40-fold induction of reporter gene expression over the background level.

EXAMPLE 11

A similar set of constructs were made to establish an assay for the G protein coupled serotonin receptor 1a (HTR1A). The HTR1A coding region,(Genbank Accession Number: NM_000524) (SEQ ID NO: 26) was modified to place an EcoRI site at the 5' end and replace the stop codon with a BamHI site using PCR with the primers

```
gaattcatgg atgtgctcag ccctgg      (SEQ ID NO: 27)
``` and

```
ggatccctgg cggcagaact tacac.      (SEQ ID NO: 28)
```

The modified HTR1A coding region was ligated into the AVPR2-tTA constructs described supra, which had been cut with EcoRI and BamHI. This replaced the entire coding sequence of AVPR2 with the coding sequence of HTR1A. The resulting construct will be referred to as "HTR1A-tTA" hereafter.

Clone 41 cells were co-transfected with the HTR1A-tTA fusion construct containing the low efficiency cleavage site and the ARRB2-TEV-NIa protease fusion construct described supra, and assays were carried out using 10 μM 8-hydroxy-DPAT HBr (OH-DPAT), an agonist for the HTR1A, as well as with 10 μM serotonin, a natural agonist for HTR1A. The assays were carried out as described, supra. The maximal response to OH-DPAT resulted in a 6.3-fold induction of reporter gene expression over background level and the maximal response to serotonin resulted in a 4.6-fold induction of reporter gene expression over background level.

EXAMPLE 12

Similar constructs were made to establish an assay for the G protein coupled m2 muscarinic acetylcholine receptor (CHRM2). The CHRM2 coding region (Genbank Accession Number: NM_000739) (SEQ ID NO: 29) was modified to place an EcoRI site at the 5' end and replace the stop codon with a BglII site using PCR with the primers

```
gaattcatga ataactcaac aaactcc      (SEQ ID NO: 30)

and agatctcctt gtagcgccta tgttc.       (SEQ ID NO: 31)
```

The modified CHRM2 coding region was ligated into the AVPR2-tTA constructs described supra, which had been cut with EcoRI and BamHI. This replaced the entire coding sequence of AVPR2 with the coding sequence of CHRM2.

Clone 41 cells were co-transfected with the CHRM2-tTA fusion construct containing the high efficiency cleavage site and the ARRB2-TEV-NIa protease fusion described supra, where the ARRB2-protease fusion protein was expressed under the control of the Herpes Simplex Virus thymidine kinase (HSV-TK) promoter, and assays were carried out using 10 μM carbamylcholine Cl (carbochol), an agonist for CHRM2, as described supra. The maximal response to carbochol resulted in a 7.2-fold induction of reporter gene expression over background.

EXAMPLE 13

α Constructs were also made to establish an assay for the G protein coupled chemokine (C-C motif) receptor 5 (CCR5). The CCR5 coding region (Genbank Accession Number: NM_000579) (SEQ ID NO: 32) was modified to place Not I site at the 5' end and replace the stop codon with a BamHI site using PCR with the primers

```
gcggccgcat ggattatcaa gtgtcaagtc c (SEQ ID NO: 33)

and ggatccctgg cggcagaact tacac.       (SEQ ID NO: 34)
```

The CCR5 coding region was also modified to place a BsaI site at the 5' end which, when cut, leaves a nucleotide overhang which is compatible with EcoRI cut DNA using the primers

```
ggtctccaat tcatggatta tcaagtgtca   (SEQ ID NO: 35)

agt and gacgacagcc aggtacctat c.           (SEQ ID NO: 36)
```

The first modified coding region was cut with ClaI and BamHI and the second was cut with BsaI and ClaI. Both fragments were ligated into the AVPR2-tTA constructs described supra, which had been cut with EcoRI and BamHI. This replaced the entire coding sequence of AVPR2 with the coding sequence of CCR5.

The CCR5-tTA fusion construct containing the low efficiency cleavage site was transfected into "clone 34" cells, which are a derivative of the HEK cell line "clone 41" described supra, but which contain a stably integrated ARRB2-TEV-NIa protease fusion gene under the control of the CMV promoter. Assays were carried out using 1 μg/ml "Regulated on Activation, Normal T-Cell Expressed and Secreted" (RANTES), a known agonist for CCR5. The maximal response to RANTES, measured as described supra resulted in an approximately 40-fold induction of reporter gene expression over the background.

EXAMPLE 14

Next, a set of constructs were made to establish an assay for the G protein coupled dopamine 2 receptor (DRD2). The DRD2 coding region (Genbank Accession Number: NM_000795) (SEQ ID NO: 37) was modified to place an EcoRI site at the 5' end and replace the stop codon with a BglII site using PCR with the primers

```
gaattcatgg atccactgaa tctgtcc      (SEQ ID NO: 38)

and agatctgcag tggaggatct tcagg.       (SEQ ID NO: 39)
```

The modified DRD2 coding region was ligated into the AVPR2-tTA constructs described supra, cut with EcoRI and BamHI. This replaced the entire coding sequence of AVPR,2 with the coding sequence of DRD2.

Clone 41 cells were co-transfected with the DRD2-tTA fusion construct containing the medium efficiency cleavage site and the ARRB2-TEV-NIa protease fusion described supra, and assays were carried out using 10 μM dopamine HCl (dopamine), an agonist for DRD2. Results were measured as in the assays described supra. The maximal response to dopamine resulted in a 2.7-fold induction of reporter gene expression over the background.

EXAMPLE 15

These experiments were designed to demonstrate enhancements of the assay using arrestin variants that bind agonist-occupied GPCRs more stably. First, a fusion of the TEV NIa protease to β-arrestin-1 (ARRB1) was constructed. The coding region of ARRB1 (Genbank Accession Number: NM_004041) (SEQ ID NO: 40) was modified to place an Asp718 site at the 5' end and replace the stop codon with a BamHI site using PCR with the primers

```
ggtaccatgg gcgacaaagg gacgcgagtg    (SEQ ID NO: 41)

and ggatcctctg ttgttgagct gtggagagcc    (SEQ ID NO: 42)
tgtaccatcc tcctcttc.
```

The resulting modified ARRB1 coding region was cut with Asp718 and EcoRI and with EcoRI and BamHI, while the modified TEV NIa-Pro coding region described supra was cut with BglII and NotI. All three fragments were ligated into a commercially available pcDNA3 expression vector, which had digested with Asp718 and NotI.

Clone 41 cells were co-transfected with the DRD2-tTA fusion construct containing the medium efficiency cleavage site and the ARRB1-TEV-NIa protease fusion, and assays were carried out using 10 µM dopamine HCl (dopamine), an agonist for the D2 receptor, as described supra. The maximal response to dopamine resulted in a 2.1-fold induction of reporter gene expression over the background.

Truncation of ARRB1 following amino acid 382 has been reported to result in enhanced affinity for agonist-bound GPCRs, independent of GRK-mediated phosphorylation (Kovoor A., et. al., *J. Biol. Chem.*, 274(11):6831–6834 (1999)). To demonstrate the use of such a "constitutively active" arrestin in the present assay, the coding region of β-arrestin-1 was modified to place an Asp718 site at the 5' end and a BamHI site after amino acid 382 using PCR with SEQ ID NO: 41, supra and

```
   ggatccattt gtgtcaagtt ctatgag (SEQ ID NO: 43).
```

This results in a an ARRb1 coding region which is 36 amino acids shorter than the fill-length coding region. The resulting modified ARRB1 coding region, termed "ARRB1 (Δ383)", was cut with Asp718 and EcoRI and with EcoRI and BamHI, while the modified TEV NIa-Pro coding region described supra was cut with BglII and NotI. All three fragments were ligated into a commercially available pcDNA3 expression vector, digested with Asp718 and NotI.

Clone 41 cells were co-transfected with the DRD2-tTA fusion construct containing the medium efficiency cleavage site and the ARRB1 (Δ383)-TEV-NIa protease fusion, and assays were carried out using 10 µM dopamine HCl (dopamine), an agonist for the DRD2 receptor, as described supra. The maximal response to dopamine resulted in an 8.3-fold induction of reporter gene expression over the background.

To examine the effect of a comparable truncation of the ARRB2 coding region the coding region of ARRB2 was modified to place an Asp718 site at the 5' end and replaced 81 nucleotides at the 3' end with a BamHI site using PCR with the primers

```
   ggtaccatgg gggagaaacc cgggacc    (SEQ ID NO: 44)

and ggatcctgtg gcatagttgg tatc.      (SEQ ID NO: 45)
```

This results in a ARRB2 coding region which is 27 amino acids shorter than the full-length coding region. The resulting modified ARRB2 coding region was cut with Asp718 and BamHI, while the modified TEV NIa-Pro coding region described supra was cut with BglII and NotI. Both fragments were ligated into a commercially available pcDNA3 expression vector, digested with Asp718 and NotI.

Clone 41 cells were co-transfected with the DRD2-tTA fusion construct containing the medium efficiency cleavage site and the ARRB2 (Δ383)-TEV-NIa protease fusion, and assays were carried out using 10 µM dopamine HCl (dopamine), an agonist for the DRD2 receptor, as described supra. The maximal response to dopamine resulted in a 2.1-fold induction of reporter gene expression over the background.

Figure 4:
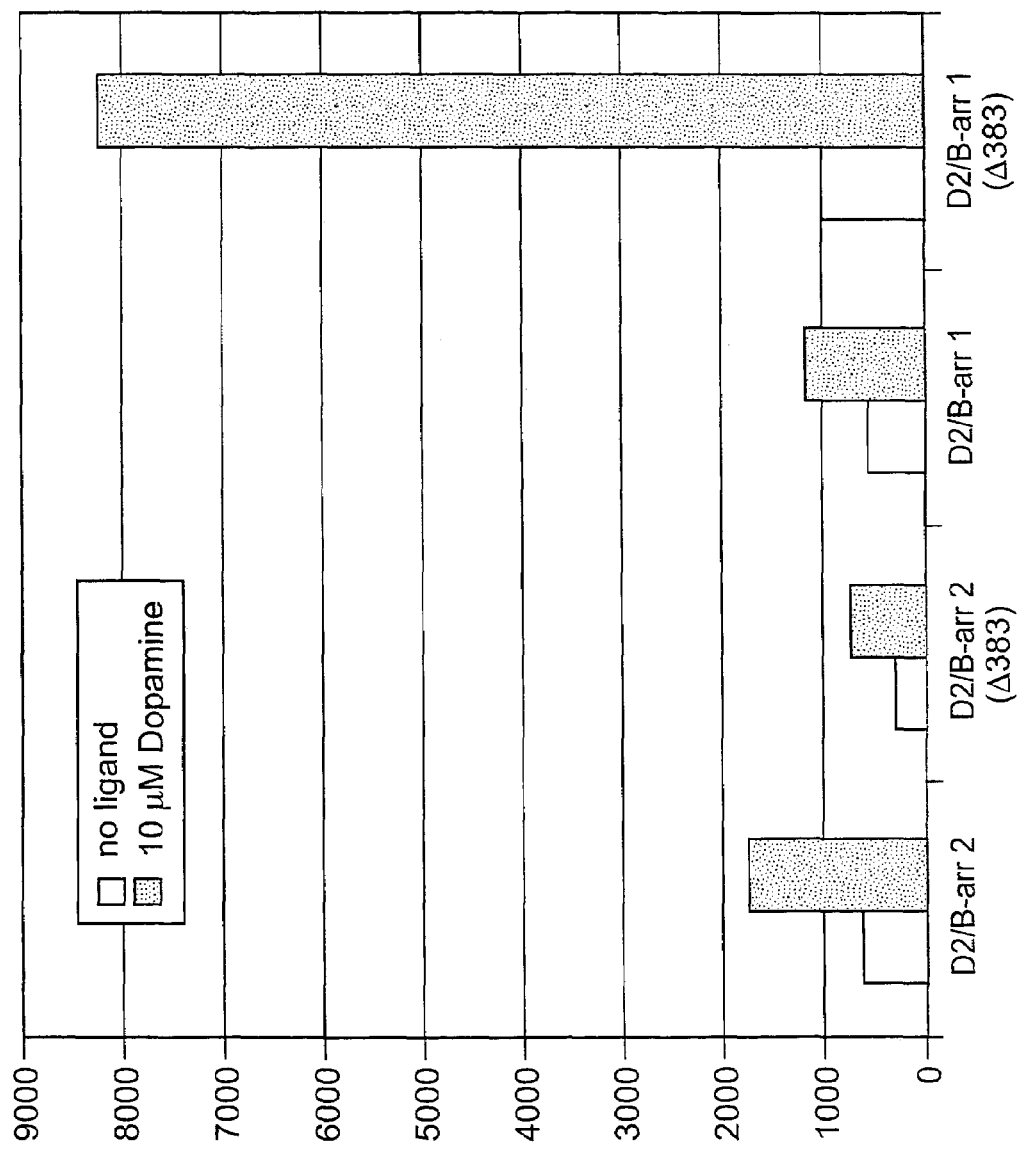
FIG. 4 depicts results obtained in accordance with the invention, using the D2 dopamine receptor.

These results, presented in FIG. 4, demonstrate that DRD2 dopamine receptor assay shows the highest signal-to-background ratio using the arrestin variant ARRB1 (Δ383).

EXAMPLE 16

This set of experiments was carried out to demonstrate enhancements of the assay using receptor modifications that are designed to increase affinity for the interacting protein. In this example, the C-terminal tail domain of a test receptor was replaced with the corresponding tail domain from AVPR2, a receptor known to bind arrestins with high affinity. In these examples the fusion junction was made 15–18 amino acids after the conserved NPXXY motif at the end of the seventh transmembrane helix, which typically corresponds to a position immediately after a putative palmitoylation site in the receptor C-terminus.

First, PCR was used to produce a DNA fragment encoding the C-terminal 29 amino acids from AVPR2, followed by the low efficiency TEV cleavage site and tTA transcription factor. The fragment was also designed such that the first two amino acids (Ala, A and Arg, R) are encoded by the BssHII restriction site GCGCGC. This was accomplished by amplifying the AVPR2-tTA construct with the low efficiency cleavage site described supra with the primers

```
tgtgcgcgcg gacgcacccc acccagcctg   (SEQ ID NO: 46)

ggt and ctcgagagat cctcgcgccc cctacccacc.  (SEQ ID NO: 11)
```

Next, the coding region of the DRD2 was modified to place an EcoRI site at the 5' end and to insert a BssHII site after the last amino acid in the coding region (Cys-443). This was done using PCR with the primers

```
gaattcatgg atccactgaa tctgtcc      (SEQ ID NO: 47)

and tgtgcgcgcg cagtggagga tcttcaggaa   (SEQ ID NO: 48)
ggc.
```

The resulting modified D2 coding region was cut with EcoRI and BssHII and the resulting AVPR2 C-terminal tail-low efficiency cleavage site-tTA fragment was cut with BssHII and BamHI. Both fragments were ligated into the AVPR2-low efficiency cleavage site-tTA construct described supra, cut with EcoRI and BamHI.

Clone 41 cells were co-transfected with the DRD2-AVPR2 Tail-tTA fusion construct containing the low efficiency TEV cleavage site and the ARRB2-TEV-NIa protease fusion described supra, and assays were carried out using 10 µM dopamine HCl (dopamine), an agonist for the DRD2 receptor. The maximal response to dopamine resulted in an approximately 60-fold induction of reporter gene expression over the background.

A construct was made which modified the ADRB2 receptor coding region by inserting an Asp718 site at the 5' end and by placing a BssHII site after Cys-341. This was done using PCR with the primers

```
gcggccgcca ccatgaacgg taccgaaggc    (SEQ ID NO: 49)
cca
``` and

```
tgtgcgcgcg cacagaagct cctggaaggc.   (SEQ ID NO: 50)
```

The modified ADRB2 receptor coding region was cut with EcoRI and BssHII and the AVPR2 C-terminal tail-low efficiency cleavage site-tTA fragment was cut with BssHII and BamHI. Both fragments were ligated into the AVPR2-low efficiency cleavage site-tTA construct described supra cut, with EcoRI and BamHI. The resulting construct is "ADRB2-AVPR2 Tail-tTA." (Also see published application U.S. 2002/0106379, supra, SEQ ID NO: 3 in particular.)

Clone 41 cells were co-transfected with the ADRB2-AVPR2 Tail-tTA fusion construct containing the low efficiency TEV cleavage site and the ARRB2-TEV-NIa protease fusion described supra, and assays were carried out using 10 µM isoproterenol, an agonist for the ADRB2 receptor. The maximal response to isoproterenol resulted in an approximately 10-fold induction of reporter gene expression over the background.

A construct was made which modified the kappa opioid receptor (OPRK; Genbank Accession Number: NM_000912) (SEQ ID NO: 51) coding region by placing a BssHII site after Cys-345. This was done using PCR with the primers

```
ggtctacttg atgaattcct ggcc          (SEQ ID NO: 52)
``` and

```
gcgcgcacag aagtcccgga aacaccg       (SEQ ID NO: 53)
```

The modified OPRK receptor coding region was cut with EcoRI and BssHII and AVPR2 C-terminal tail-low efficiency cleavage site-tTA fragment was cut with BssHII and XhoI. Both fragments were ligated into a plasmid containing the modified OPRK receptor sequence, cloned into pcDNA3.1+ at Asp718 (5') and XhoI (3'), which had been digested with EcoRI and XhoI.

Clone 41 cells were co-transfected with the OPRK-AVPR2 Tail-tTA fusion construct containing the low efficiency cleavage site and the ARRB2-TEV-NIa protease fusion described supra, and assays were carried out using 10 µM U-69593, an agonist for the OPRK. The maximal response to U-69593 resulted in an approximately 12-fold induction of reporter gene expression over the background.

EXAMPLE 17

This experiment was designed to demonstrate the use of the assay to measure the activity of two test receptors simultaneously using a multiplex format.

Clone 41 cells and "clone 1H10" cells, which are cells of an HEK-293T cell line containing a stable integration of the luciferase gene under the control of a tTA-dependent promoter, were each plated on 24-well culture dishes and were transiently transfected with the chimeric ADRB2-AVPR2 Tail-tTA or the DRD2-AVPR2 Tail-tTA fusion constructs described supra, respectively. Transient transfections were performed using 100 µl of media, 0.4 µg of DNA and 2 µl of FuGene reagent per well. After 24 hr of incubation, Clone 41 cells expressing ADRB2-AVPR2 Tail-tTA and clone 1H10 cells expressing DRD2-AVPR2 Tail-tTA were trypsinized, mixed in equal amounts, and replated in 12 wells of a 96-well plate. Triplicate wells were incubated without drug addition or were immediately treated with 1 µM isoproterenol, 1 µM dopamine, or a mixture of both agonists at 1 µM. Cells were assayed for reporter gene activity approximately 24 hours after ligand addition. Medium was discarded, cells were lysed in 40 µl lysis buffer [100 mM potassium phosphate pH 7.8, 0.2% Triton X-100] and the cell lysate was assayed for beta-galactosidase and for luciferase activity using commercially available luminescent detection reagents.

The results are presented in FIGS. 5A and 5B. Treatment with isoproterenol resulted in an approximately seven-fold induction of beta-galactosidase reporter gene activity, whereas luciferase activity remained unchanged. Treatment with dopamine resulted in a 3.5-fold induction of luciferase activity, while beta-galactosidase activity remained unchanged. Treatment with both isoproterenol and dopamine resulted in seven-fold and three-fold induction of beta-galactosidase and luciferase activity, respectively.

EXAMPLE 18

This experiment was designed to demonstrate the use of the assay to measure the activity of two test receptors simultaneously using a multiplex format.

Figure 6:
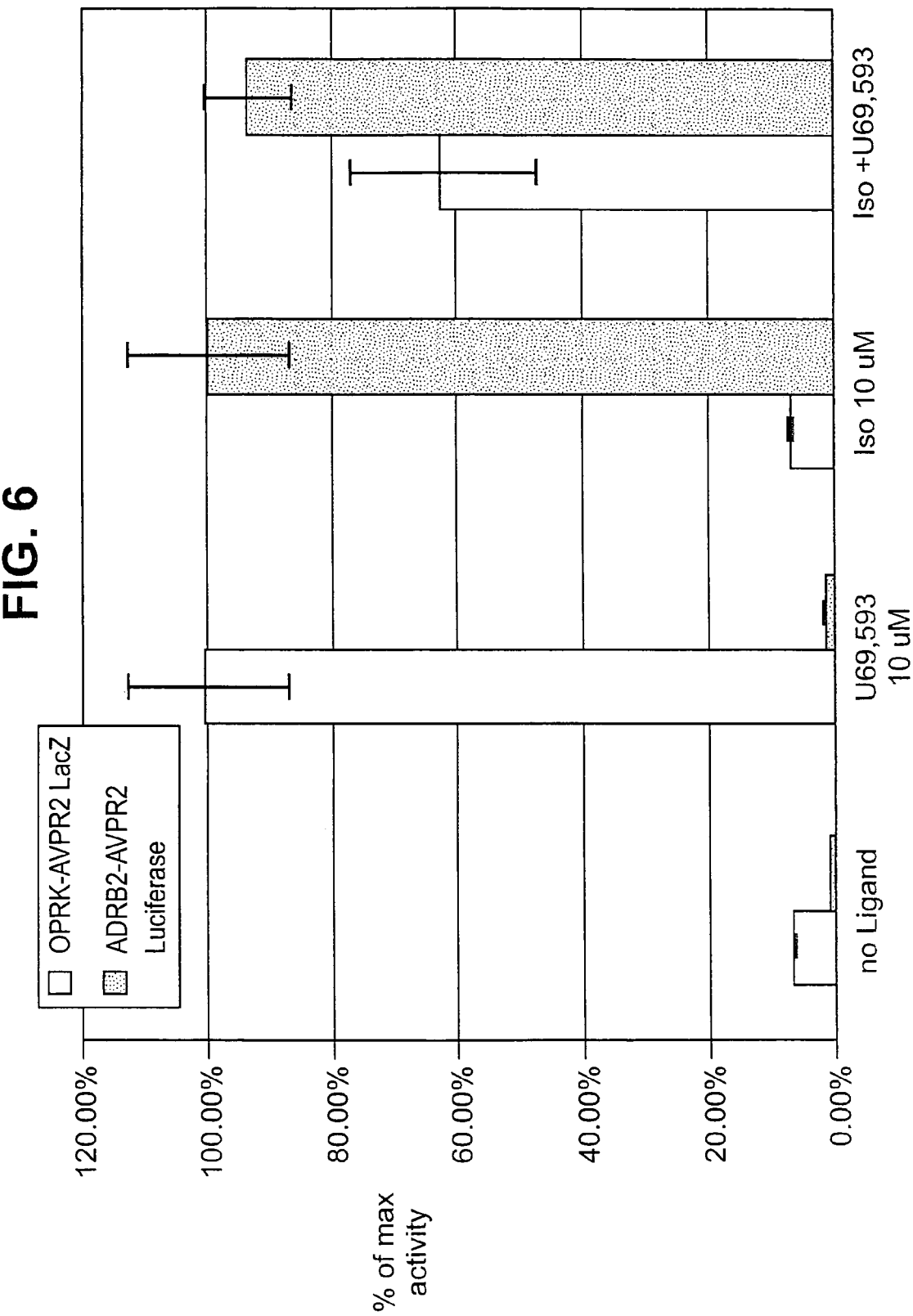
FIG. 6 sets forth the result of another "multiplex" assay, i.e., one where two molecules are studied simultaneously.

"Clone 34.9" cells, which are a derivative of clone 41 cells and containing a stably integrated ARRB2-TEV NIa protease fusion protein gene, were transiently transfected with the chimeric OPRK-AVPR2 Tail-TEV-NIa-Pro cleavage (Leu)-tTA fusion construct described supra. In parallel, "clone HTL 5B8.1" cells, which are an HEK-293T cell line containing a stable integrated luciferase gene under the control of a tTA-dependent promoter, were transiently transfected with the ADRB-AVPR2 Tail-TEV-NIa-Pro cleavage (Leu)-tTA fusion construct described supra. In each case 5×10⁵ cells were plated in each well of a 6-well dish, and cultured for 24 hours in DMEM supplemented with 10% fetal bovine serum, 2 mM L-Glutamine, 100 units/ml penicillin, 500 µg/ml G418, and 3 µg/ml puromycin. Cells were transiently transfected with 100 µl of DMEM, 0.5 µg of OPRK-AVPR2 Tail-TEV-NIa-Pro cleavage (Leu)-tTA DNA, and 2.5 µl Fugene ("clone 34.9 cells") or with 100 µl of DMEM, 0.5 µg of ADRB2-AVPR2 Tail-TEV-NIa-Pro cleavage (Leu)-tTA DNA, 0.5 µg of ARRB2-TEV NIa Protease DNA and 5 µl Fugene ("clone HTL 5B8.1 cells"). Transiently transfected cells were cultured for about 24 hours, and were then trypsinized, mixed in equal amounts and replated in wells of a 96 well plate. Cell were incubated for 24 hours before treatment with 10 µM U-69593, 10 µM isoproterenol or a mixture of both agonists at 10 µM. Sixteen wells were assayed for each experimental condition. After 24 hours, cells were lysed and the activity of both beta-galactosidase and luciferase reporter genes were assayed as described supra. The results are presented in FIG. 6. Treatment with U-69593 resulted in an approximately 15-fold induction of beta-galactosidase reporter gene activity, whereas luciferase activity remained unchanged. Treatment with isoproterenol resulted in a 145-fold induction of luciferase activity, while beta-galactosidase activity remained unchanged. Treatment with both U-69593 and isoproterenol resulted in nine-fold and 136-fold induction of beta-galactosidase and luciferase activity, respectively.

EXAMPLE 19

This experiment was carried out to demonstrate the use of a different transcription factor and promoter in the assay of the invention.

A fusion construct was created, comprising DNA encoding AVPR2, fused in frame to a DNA sequence encoding the amino acid linker GSENLYFQLR (SEQ ID NO: 54) which included the low efficiency cleavage site for TEV N1a-Pro described supra, fused in frame to a DNA sequence encoding amino acids 2–147 of the yeast GAL4 protein (GenBank Accession Number P04386) (SEQ ID NO: 55) followed by a linker, i.e., of the sequence PELGSASAELTMVF (SEQ ID NO: 56), followed by amino acids 368–549 of the murine nuclear factor kappa-B chain p65 protein (GenBank Accession Number A37932) (SEQ ID NO: 57). The CMV promoter was placed upstream of the AVPR2 coding region and a polyA sequence was placed downstream of the GAL4-NFkB region. This construct was designated AVPR2-TEV-NIa-Pro cleavage (Leu)-GAL4.

HUL 5C1.1 is a derivative of HEK-293T cells, which contain a stably integrated luciferase reporter gene under the control of a GAL4 upstream activating sequence (UAS), commercially available pFR-LUC.

This AVPR2-TEV-NIa-Pro cleavage (Leu)-GAL4 plasmid was co-transfected along with the β-arrestin2-TEV N1a Protease described supra into HUL 5C1.1 cells. About $2.5 \times 10^4$ cells were plated into each well of a 96 well-plate, in DMEM medium supplemented with 10% fetal bovine serum, 2 mM L-Glutamine, 100 units/ml penicillin, 500 µg/ml G418, and 3 µg/ml puromycin. Cells were grown to reach 50% confluency the next day and were transfected with 10 µl per well of a mixture consisting of 85 µl of DMEM, 0.1 µg of AVPR2-TEV-Nia-Pro cleavage (Leu)-GAL4 DNA, 0.1 µof ARRB2-TEV N1a Protease DNA, and 1 µl Fugene, which had been incubated for 15 minutes at room temperature prior to addition to the cells. Transfected cells were cultured for about 16 hours before treatment with 10 µM vasopressin. After six hours, cells were lysed and luciferase activity was assayed as described supra. Under these conditions, treatment with vasopressin resulted in a 180-fold increase in reporter gene activity.

EXAMPLE 20

This set of experiments were carried out to demonstrate enhancements of the assay using further receptor modifications that are designed to increase the affinity for the interacting protein. In this example, the C-terminal tail domain of the test receptor is replaced with the corresponding tail domain of one of the following receptors: apelin J receptor—AGTRL1 (accession number: NM_005161) (SEQ ID NO: 58), gastrin-releasing peptide receptor—GRPR (accession number: NM_005314) (SEQ ID NO: 59), proteinase-activated receptor 2—F2RL1 (accession number: NM_005242) (SEQ ID NO: 60), CCR4 (accession number: NM_005508) (SEQ ID NO: 61), chemokine (C-X-C motif) receptor 4—CXCR4 (accession number: NM_003467) (SEQ ID NO: 62), and interleukin 8 receptor, beta—CXCR2/IL8b (accession number: NM_001557) (SEQ ID NO: 63).

First PCR was used to produce a DNA fragment encoding the C-terminal tail of the above receptors. These fragments were designed such that the first two amino acids (Ala, A and Arg, R) are encoded by the BssHII restriction site.

The AGTRL1 C-terminal fragment was amplified with the primers

```
tgtgcgcgcg gccagagcag gtgcgca    (SEQ ID NO: 64)
and
gaggatccgt caaccacaag ggtctc.    (SEQ ID NO: 65)
```

The GRPR C-terminal fragment was amplified with the primers

```
tgtgcgcgcg gcctgatcat ccggtct    (SEQ ID NO: 66)
and
gaggatccga cataccgctc gtgaca.    (SEQ ID NO: 67)
```

The F2RL1 C-terminal fragment was amplified with the primers

```
tgtgcgcgca gtgtccgcac tgtaaagc    (SEQ ID NO: 68)
and
gaggatccat aggaggtctt aacagt.    (SEQ ID NO: 69)
```

The CCR4 C-terminal fragment was amplified with the primers

```
tgtgcgcgcg gccttttttgt gctctgc    (SEQ ID NO: 70)
and
gaggatccca gagcatcatg aagatc.    (SEQ ID NO: 71)
```

The CXCR2/IL8b C-terminal fragment was amplified with the primers

```
tgtgcgcgcg gcttgatcag caagggac    (SEQ ID NO: 72)
and
gaggatccga gagtagtgga agtgtg.    (SEQ ID NO: 73)
```

The CXCR4 C-terminal fragment was amplified with the primers

```
tgtgcgcgcg ggtccagcct caagatc    (SEQ ID NO: 74)
and
gaggatccgc tggagtgaaa acttga.    (SEQ ID NO: 75)
```

The resulting DNA fragments encoding the modified C-terminal tail domains of these receptors were cut with BssHII and BamHI and the fragments were ligated in frame to the OPRK receptor coding region, replacing the AVPR2-C-terminal tail fragment, in the OPRK-AVPR2 Tail-TEV-NIa-Pro cleavage (Leu)-tTA expression construct described supra.

HTL 5B8.1 cells described supra were co-transfected with each of the above modified OPRK coding region—TEV-NIa-Pro cleavage (Leu)—tTA constructs and the β-arrestin 2—TEV NIa protease fusion described supra. About $2.5 \times 10^4$ cells per well were plated onto a 96 well-plate, in DMEM medium supplemented with 10% fetal bovine serum, 2 mM L-Glutamine, 100 units/ml penicillin, 500 µg/ml G418, and 3 µg/ml puromycin. Cells were grown to reach 50% confluency the next day and were transfected with 10 μl per well of a mixture consisting of 85 μl of DMEM, 0.25 μg of AVPR2-TEV-NIa-Pro cleavage (Leu)-GAL4 DNA, 0.25 μg of ARRB2-TEV NIa protease DNA, and 2.5 μl Fugene (a proprietary transfection reagent containing lipids and other material), which had been incubated for 15 minutes at room temperature prior to addition to the cells. Transfected cells were cultured for about 16 hours before treatment 10 μM U-69593. After six hours, cells were lysed and luciferase activity was assayed as described supra. Under these conditions, treatment with U-69593 resulted in the following relative increases in reporter gene activity for each of the modified OPRK receptors: OPRK-AGTRL1 C-terminal tail—30 fold; OPRK-GRPR C-terminal tail—312 fold; OPRK-F2RL1 C-terminal tail—69.5 fold; OPRK-CCR4 C-terminal tail—3.5 fold; OPRK-CXCR4 C-terminal tail—9.3 fold; OPRK-IL8b C-terminal tail—113 fold.

EXAMPLE 21

This experiment was designed to produce a cell line that stably expressed the ARRB2-TEV NIa protease fusion protein described supra.

A plasmid was made which expressed the ARRB2-TEV NIa protease fusion protein under the control of the EF1α promoter and also expressed the hygromycin resistance gene under the control of the thymidine kinase (TK) promoter.

This plasmid was transfected into HTL 5B8.1, and clones containing a stable genomic integration of the plasmid were selected by culturing in the presence of 100 μg/ml hygromycin. Resistant clones were isolated and expanded and were screened by transfection of the ADRB2-AVPR2 Tail-TEV-NIa-Pro cleavage (Leu)-tTA plasmid described supra. Three cell lines that were selected using this procedure were designated "HTLA 4C2.10", "HTLA 2C11.6" and "HTLA 5D4". About $2.5 \times 10^4$ cells per well were plated onto a 96 well-plate, in DMEM medium supplemented with 10% fetal bovine serum, 2 mM L-Glutamine, 100 units/ml penicillin, 500 μg/ml G418, 3 μg/ml puromycin, and 100 μg/ml hygromycin. Cells were grown to reach 50% confluency the next day and were transfected with 10 μl per well of a mixture consisting of 85 μl of DMEM, 0.25 μg of ADRB2-AVPR2-TEV-NIa-Pro cleavage (Leu)-GAL4 DNA and 0.5 μl Fugene, which had been incubated for 15 minutes at room temperature prior to addition to the cells. Transfected cells were cultured for about 16 hours before treatment 10 μM isoproterenol. After six hours, cells were lysed and luciferase activity was assayed as described supra. Under these conditions, treatment with isoproterenol resulted in a 112-fold ("HTLA 4C2.10"), 56-fold ("HTLA 2C11.6") and 180-fold ("HTLA 5D4") increase in reporter gene activity in the three cell lines, respectively.

EXAMPLE 22

This experiment was designed to produce a cell line that stably expressed the ARRB2-TEV NIa protease and the ADRB2-AVPR2 Tail-TEV-NIa-Pro cleavage (Leu)-tTA fusion proteins described supra.

The ARRB2-TEV NIa protease plasmid containing the hygromycin resistance gene was transfected together with the ADRB2-AVPR2 Tail-TEV-NIa-Pro cleavage (Leu)-tTA fusion protein plasmid described supra into HTL 5B8.1 cells and clones containing stable genomic integration of the plasmids were selected by culturing in the presence of 100 μg/ml hygromycin. Resistant clones were isolated and expanded, and were screened by treating with 10 μM isoproterenol and measuring the induction of reporter gene activity as described supra. Three cell lines that were selected using this procedure were designated "HTLAR 1E4", "HTLAR 1C10" and "HTLAR 2G2". Treatment with isoproterenol for 6 hours resulted in a 208-fold ("HTLAR 1E4"), 197-fold ("HTLAR 1C10") and 390-fold ("HTLAR 2G2") increase in reporter gene activity in the three cell lines, respectively.

EXAMPLE 23

This experiment was designed to demonstrate the use of the assay to measure the activity of the receptor tyrosine kinase epidermal growth factor receptor (EGFR).

A first fusion construct was created, comprising DNA encoding the human EGFR, which can be found at GenBank under the Accession Number NM_005228 (SEQ ID NO: 76), fused in frame to a DNA sequence encoding amino acids 3–335 of the tetracycline-controlled transactivator tTA, described supra. Inserted between these sequences is a DNA sequence encoding the amino acid sequence GGSG-SENLYFQL (SEQ ID NO: 77) which includes the low efficiency cleavage site for TEV NIa-Pro, ENLYFQL (SEQ ID NO: 14), described supra. The CMV promoter was placed upstream of the Epidermal Growth Factor Receptor coding region, and a polyA sequence was placed downstream of the tTA region. This construct is designated EGFR-TEV-NIa-Pro cleavage (Leu)-tTA.

A second fusion construct was created, comprising DNA encoding the two SH2 domains of human Phospholipase C Gamma 1, corresponding to amino acids 538–759 (GeneBank accession number NP_002651.2) (SEQ ID NO: 78) fused in frame to a DNA sequence encoding the catalytic domain of mature TEV NIa protease, described supra, corresponding to amino acids 2040–2279 (GeneBank accession number AAA47910) (SEQ ID NO: 79). Inserted between these sequences is a linker DNA sequence encoding the amino acids NSSGGNSGS (SEQ ID NO: 80). The CMV promoter was placed upstream of the PLC-Gamma SH2 domain coding sequence and a polyA sequence was placed downstream of the TEV NIa protease sequence. This construct is designated PLC Gammal-TEV.

Figure 7:
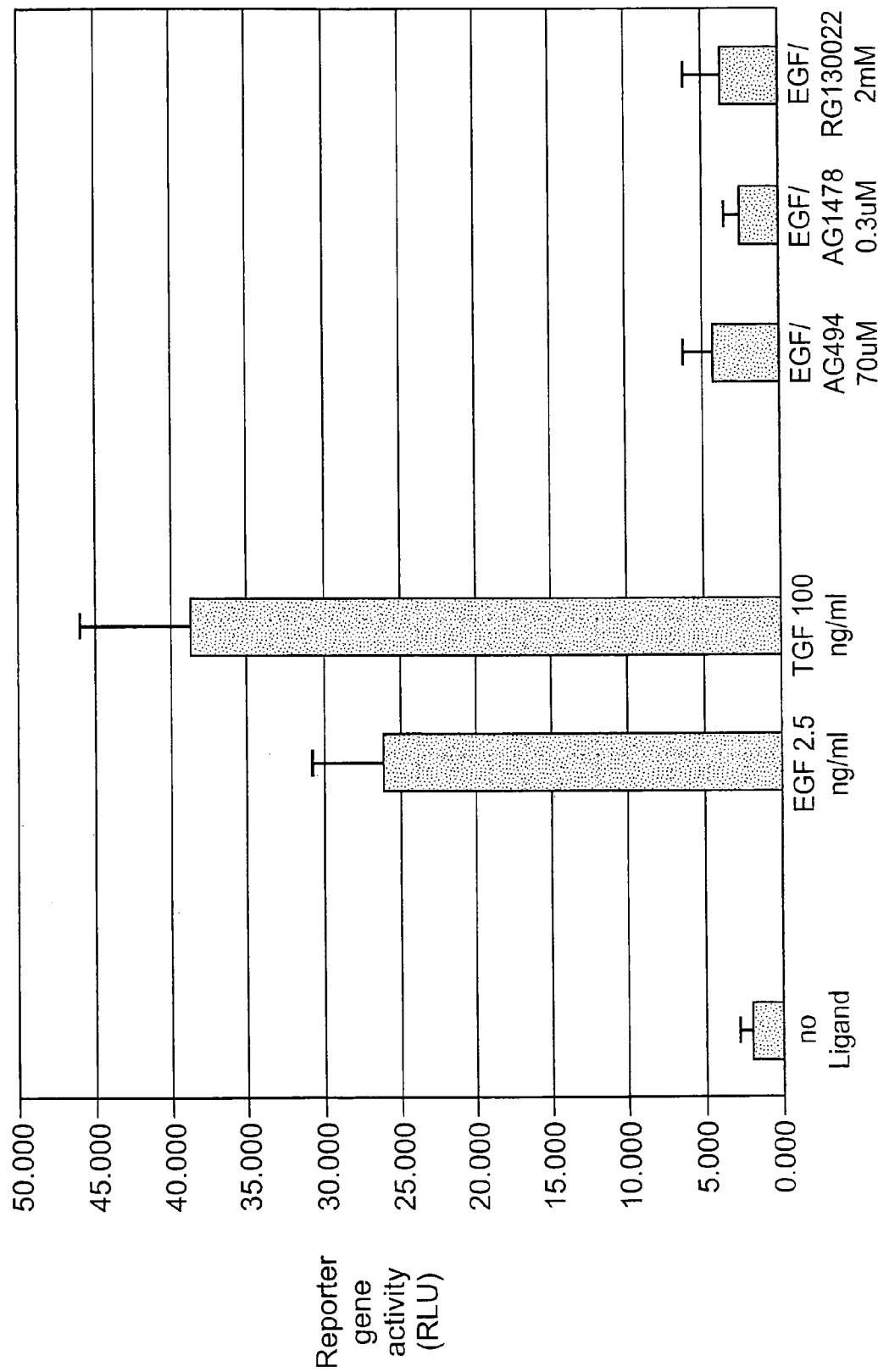
FIG. 7 presents data obtained from assays measuring EGFR activity.

The EGFR-TEV-NIa-Pro cleavage (Leu)-tTA and PLC Gammal-TEV fusion constructs were transfected into clone HTL5B8.1 cells described supra. About $2.5 \times 10^4$ cells were plated into each well of a 96 well-plate, in DMEM medium supplemented with 10% fetal bovine serum, 2 mM L-Glutamine, 100 units/ml penicillin, 500 μg/ml G418, and 3 μg/ml puromycin. Cells were grown to reach 50% confluency the next day and were transfected with 15 μl per well of a mixture consisting of 100 μl of DMEM, 0.4 μg of pcDNA3 DNA ("carrier" vector DNA), 0.04 μg of EGFR-TEV-NIa-Pro cleavage (Leu)-tTA DNA, 0.04 μg of PLC Gammal-TEV DNA, and 2 μl Fugene (a proprietary transfection reagent containing lipids and other material), which had been incubated for 15 minutes at room temperature prior to addition to the cells. Transfected cells were cultured for about 16 hours before treatment with specified receptor agonists and inhibitors. After six hours, cells were lysed and luciferase activity was assayed as described supra. Results are shown in FIG. 7.

The addition of 2.5 ng/ml human Epidermal Growth Factor (corresponding to the EC80 for this ligand) resulted in a 12.3 fold increase of luciferase reporter gene activity, while addition of 100 ng/ml human Transforming Growth Factor—Alpha resulted in an 18.3 fold increase. Prior treatment with tyrosine kinase inhibitors (70 μM AG-494; 0.3

μM AG-1478; 2 mM RG-130022) before addition of human Epidermal Growth Factor blocked the induction of reporter gene activity.

EXAMPLE 24

This experiment was designed to demonstrate the use of the assay to measure the activity of the human Type I Interferon Receptor.

A fusion construct was created, comprising DNA encoding human Interferon Receptor I (IFNAR1) (557 amino acids), which can be found in Genbank under Accession Number NM_000629 (SEQ ID NO: 81), fused in frame to a DNA sequence encoding amino acids 3–335 of the tetracycline controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the Human Interferon Receptor I (IFNAR1) coding region, and a poly A sequence was placed downstream of the tTA region. This construct is designated IFNAR1-TEV-NIa-Pro cleavage (L)-tTA.

second fusion construct was created, using DNA encoding Human Interferon Receptor 2, splice variant 2 (IFNAR2.2) (515 amino acids), which can be found at Genbank, under Accession Number L41942 (SEQ ID NO: 83), fused in frame to a DNA sequence encoding the catalytic domain of the TEV NIa protease, described supra corresponding to amino acids 2040–2279 (GenBank accession number AAA47910) (SEQ ID NO: 84). Inserted between these sequences is a DNA sequence encoding the amino acid sequence RS (Arg-Ser). The CMV promoter region was placed upstream of the Human Interferon Receptor 2 (IFNAR2.2) coding region, and a poly A sequence was placed downstream of the TEV region. This construct is designated IFNAR2.2-TEV.

Expression constructs were also generated in which the genes for Human Signal Transducer and Activator of Transcription 1 (STAT1), found in Genbank, under Accession Number NM_007315 (SEQ ID NO: 85), and Human Signal Transducer and Activator of Transcription 2 (STAT2) found in Genbank, under Accession Number NM_005419 (SEQ ID NO: 86), were expressed under the control of the CMV promoter region. These constructs were designated CMV-STAT1 and CMV-STAT2 respectively.

Figure 8:
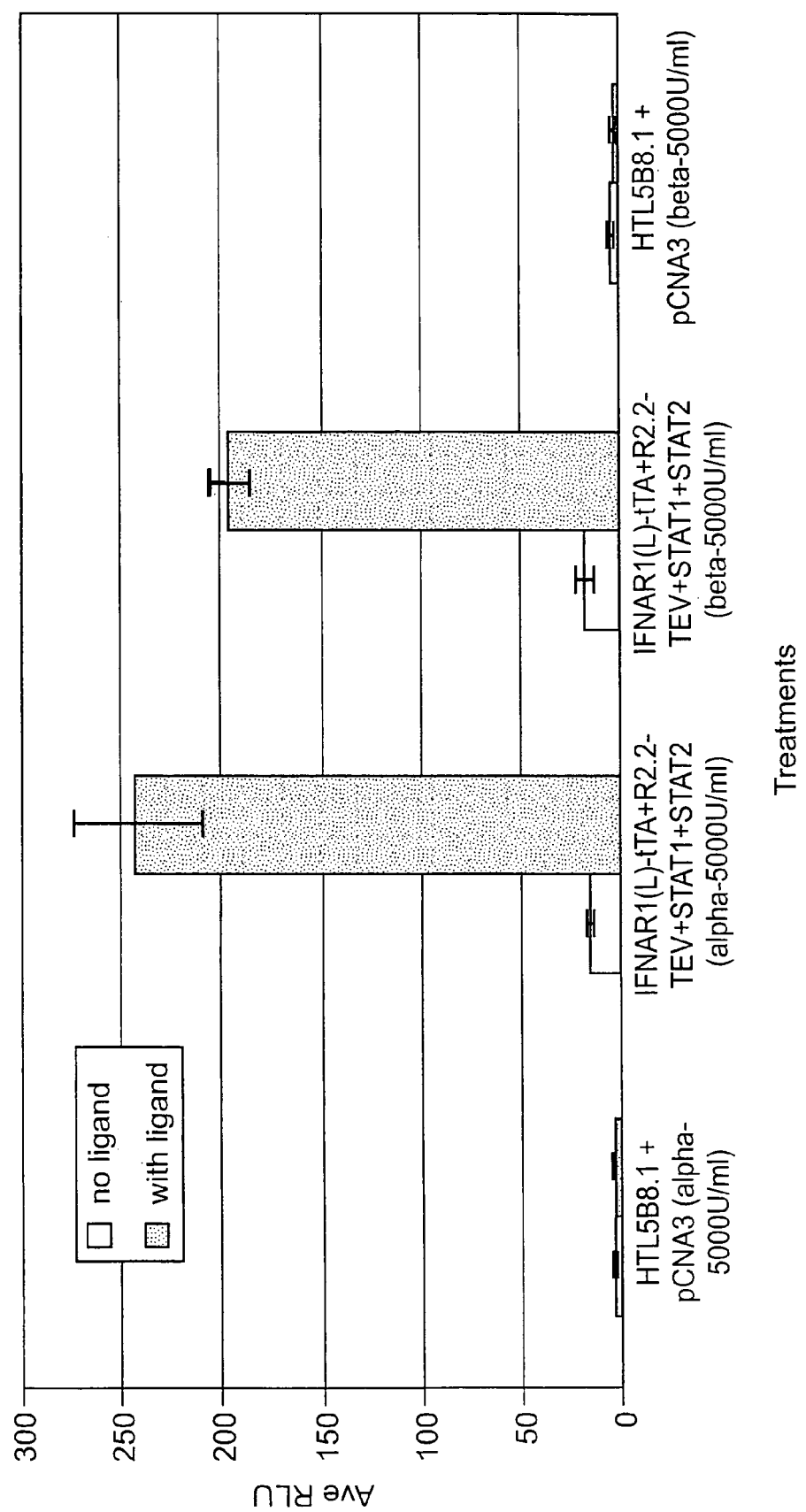
FIG. 8 presents data obtained from assays in accordance with the invention, designed to measure the activity of human type I interferon receptor.
Figure 9:
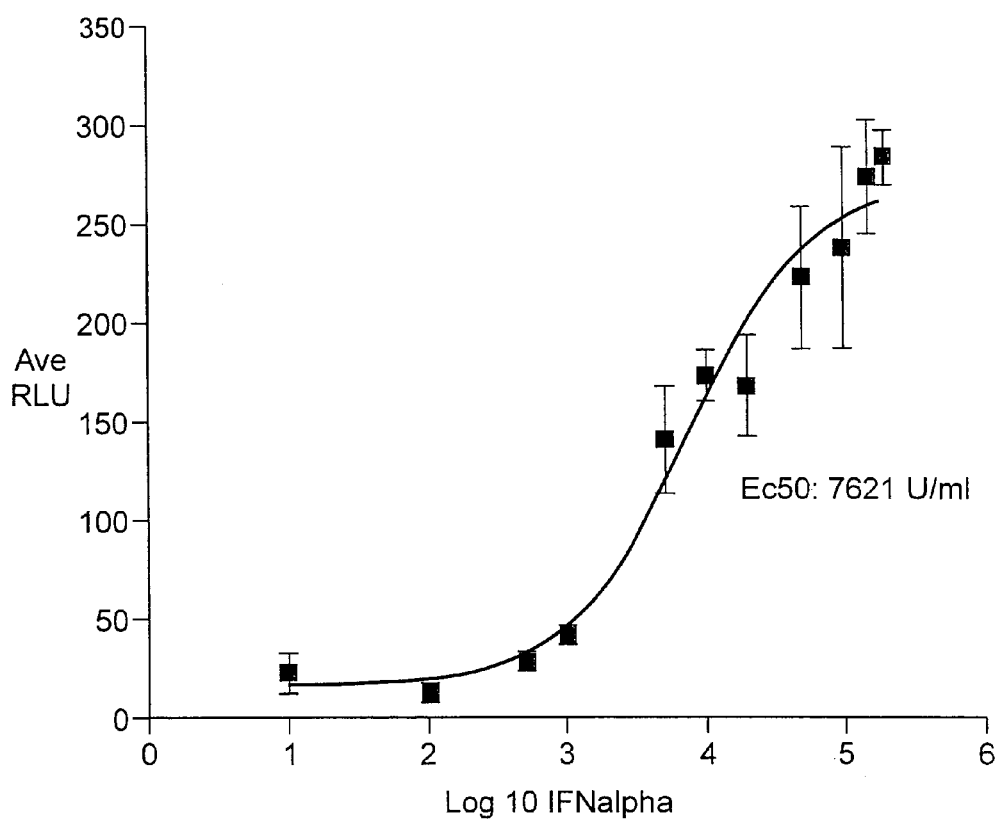
FIG. 9 elaborates on the results in FIG. 7, showing a dose response curve for IFN-α in the cells used to generate FIG. 7.

The IFNAR1-TEV-NIa-Pro cleavage (L)-tTA and IFNAR2.2-TEV fusion constructs, together with CMV-STAT1 and CMV-STAT2 were transiently transfected into HTL5B8.1 cells described supra. About $2.5 \times 10^4$ cells were seeded in each well of a 96 well plate and cultured in DMEM medium supplemented with 10% fetal bovine serum, 2 mM L-glutamine, 100 units/ml penicillin, 100 μg/ml G418, and 5 μg/ml puromycin. After 24 hours of incubation, cells were transfected with 15 ng of each IFNAR1-TEV-NIa-Pro cleavage (L)-tTA, IFNAR2.2-TEV, CMV-STAT1 and CMV-STAT2 DNA, or with 60 ng control pcDNA plasmid, together with 0.3 μl Fugene per well. Transfected cells were cultured for 8–20 hours before treatment with 5000 U/ml human interferon-alpha or 5000 U/ml human interferon-beta. At the time of interferon addition, medium was aspirated and replaced with 293 SFM II media supplemented with 2 mM L-glutamine, 100 units/ml penicillin, 3 μg/ml puromycin and 500 μg/ml of G418. Interferon-treated cells were cultured for an additional 18–20 hours before they were assayed for luciferase reporter gene activity as described supra. Results are shown in FIG. 8. Treatment with 5000 U/ml IFN-α resulted in 15-fold increase in reporter gene activity, while treatment with 5000 U/ml IFN-β resulted in a 10-fold increase. Interferon treatment of HTL5B8.1 cells transfected with the control plasmid pcDNA3 had no effect on reporter gene activity. FIG. 9 shows a dose-response curve generated for IFN-α in HTL5B8.1 cells transfected with IFNAR1(ENLYFQ(L)-tTa, IFNAR2.2-TEV, STAT1 and STAT2 expression constructs as described supra.

EXAMPLE 25

This experiment was designed to demonstrate the use of the assay to measure the activity of the human Type I Interferon Receptor using a different transcription factor and a different cell line.

A fusion construct was created, using DNA encoding Human Interferon Receptor I (IFNAR1), fused in frame to a DNA sequence encoding the GAL4-NF-κB-fusion, described supra. Inserted between these sequences is a DNA sequence encoding the amino acid sequence GSENLYFQL (SEQ ID NO: 87), which includes the low efficiency cleavage site for TEV NIa-Pro, ENLYFQL (SEQ ID NO: 14), described supra. The CMV promoter was placed upstream of the Human Interferon Receptor I (IFNAR1) coding region, and a poly A sequence was placed downstream of the GAL4-NF-κB region. This construct is designated IFNAR1-TEV- NIa-Pro cleavage (L)-GAL4-NF-κB.

CHO-K1 cells were then transiently transfected with a mixture of five plasmids: IFNAR1-TEV-NIa-Pro cleavage (L)-GAL4-NF-κB, IFNAR2.2-TEV, CMV-STAT1, CMV-STAT2 and pFR-Luc, a luciferase reporter gene plasmid under the control of a GAL4-dependent promoter. About $1.0 \times 10^4$ cells per well were seeded in a 96 well plate 24 hours prior to transfections in DMEM medium supplemented with 10% fetal bovine serum, 2 mM L-glutamine, 100 units/ml penicillin. Cells were transfected the following day with 10 ng of reporter plasmid (pFR-Luc), plus 20 ng of each of the expression constructs described supra or with 10 ng reporter plasmid plus 80 ng of control pcDNA3 plasmid, together with 0.3 μl Fugene per well. Transfected cells were cultured for 8–20 hours before treatment with 5000 U/ml human interferon-alpha. At the time of interferon addition. medium was aspirated and replaced with DMEM media supplemented with 2 mM L-glutamine, 100 units/ml penicillin. Interferon-treated cells were cultured for an additional 6 hours before they were assayed for luciferase reporter gene activity as described supra. Results are shown in FIG. 10. IFN-α treatment of CHO-K1 cells transfected with the reporter, IFNAR and STAT constructs resulted in 3-fold increase in reporter gene activity, while interferon treatment of cells transfected with the reporter and control plasmids had no effect on reporter gene activity.

EXAMPLE 26

This set of experiments was carried out to demonstrate additional enhancements of the assay using receptor modifications designed to increase the affinity of the test receptor for the interacting protein. In these examples, the fusion junction between the test receptor and a C-terminal tail domain of GRPR (Genbank Accession Number: NM_005314) (SEQ ID NO: 59) was made 17–23 amino acids after the conserved NPXXY motif at the end of the seventh transmembrane helix.

First, PCR was used to produce a DNA fragment encoding the C-terminal 42 amino acids from GRPR beginning 2 amino acids after the putative palmitoylation site (hereafter referred to as GRPR 42aa). The fragment was designed such that the first amino acid of the C-terminal tail is preceded by two amino acids (Ser, S and Arg, R) which are encoded by the XbaI restriction site TCTAGA, and the stop codon is replaced by two amino acids (Gly, G and Ser, S) which are encoded by a BamHI restriction site GGATCC. This was accomplished by amplifying a plasmid containing the GRPR coding region with primers

```
tctagaggcctgatcatccggtctcac    (SEQ ID NO: 88)

and gaggatccgacataccgctcgtgaca     (SEQ ID NO: 67)
```

Next the coding region of OPRK (Genbank Accession Number: NM_000912) (SEQ ID NO: 51) was modified to place insert an XbaI site after Pro-347. This was done using PCR with the primers

```
ggtctacttgatgaattcctggcc       (SEQ ID NO: 52)

and tctagatggaaaacagaagtcccggaaac  (SEQ ID NO: 89)
```

In addition, the coding region of ADRA1A (Genbank Accession Number: NM_000680) (SEQ ID NO: 90) was modified to insert an XbaI site after Lys-349. This was done using PCR with the primers

```
ctcggatatctaaacagctgcatcaa     (SEQ ID NO: 91)

and tctagactttctgcagagacactggattc  (SEQ ID NO: 92)
```

In addition, the coding region of DRD2 (Genbank Accession Number: NM_000795) (SEQ ID NO: 37) was modified to insert two amino acids (Leu and Arg) and an XbaI site after Cys-343. This was done using PCR with the primers

```
gaattcatggatccactgaatctgtcc    (SEQ ID NO: 38)

and tctagatcgaaggcagtggaggatcttcagg (SEQ ID NO: 93)
```

The modified OPRK receptor coding region was cut with EcoRI and XbaI and the GRPR 42aa C-terminal tail fragment was cut with XbaI and BamHI. Both fragments were ligated into a plasmid containing the OPRK receptor with the AVPR2 C-terminal tail-low-efficiency cleavage site-tTA described supra which had been digested with EcoRI and BamHI.

The modified ADRA1A receptor coding region was cut with EcoRV and XbaI and the OPRK-GRPR 42aa Tail-tTA fusion construct containing the low efficiency cleavage site was cut with XbaI and XhoI. Both fragments were ligated into a plasmid containing the ADRA1A receptor which had been digested with EcoRV and XhoI.

The modified DRD2 receptor coding region was cut with EcoRI and XbaI and the OPRK-GRPR 42aa Tail-tTA fusion construct containing the low efficiency cleavage site was cut with XbaI and XhoI. Both fragments were ligated into a pcDNA6 plasmid digested with EcoRI and XhoI HTLA 2C11.6 cells, described supra, were transfected with OPRK-GRPR 42aa Tail-tTA fusion construct containing the low efficiency cleavage site and assays were carried out using 10 µM U-69593, an agonist for OPRK. The maximal response to U-69593 resulted in an approximately 200-fold increase in reporter gene activity.

HTLA 2C11.6 cells were transfected with ADRA1A-GRPR 42aa Tail-tTA fusion construct containing the low efficiency cleavage site and assays were carried out using 10 µM epinephrine, an agonist for ADRA1A. The maximal response to epinephrine resulted in an approximately 14-fold increase in reporter gene activity.

HTLA 2C11.6 cells were transfected with DRD2-GRPR 42aa Tail-tTA fusion construct containing the low efficiency cleavage site and assays were carried out using 10 µM dopamine, an agonist for DRD2. The maximal response to dopamine resulted in an approximately 30-fold increase in reporter gene activity.

EXAMPLE 27

This set of experiments were carried out to demonstrate further enhancements of the assay using a different set of test receptor modifications designed to increase the affinity for the interacting protein. In these examples, the C-terminal domain of the test receptor was replaced with a portion of the endogenous C-terminal tail domain of GRPR.

First, PCR was used to produce a DNA fragment encoding the truncated GRPR tail, specifically a sequence encoding 23 amino acids from Gly-343 to Asn-365. The fragment was designed such that the first amino acid of the C-terminal tail is preceded by two amino acids (Ser, S and Arg, R) which are encoded by the XbaI restriction site TCTAGA. and the Ser-366 is replaced by two amino acids (Gly, G and Ser, S) which are encoded by a BamHI restriction site GGATCC. This was accomplished by amplifying a plasmid containing the GRPR coding region with primers

```
tctagaggcctgatcatccggtctcac    (SEQ ID NO: 94)

and cggatccgttggtactcttgagg        (SEQ ID NO: 95)
```

Next the truncated GRPR fragment (hereafter referred to as GRPR 23aa Tail) was cut with XbaI and BamHI and inserted into the OPRK-GRPR 42aa Tail-tTA fusion construct containing the low efficiency cleavage site described herein, digested with XbaI and BamHI.

Similarly, the GRPR 23aa Tail fragment was cut with XbaI and BamHI and inserted into the ADRA1A-GRPR 42aa Tail-tTA fusion construct containing the low efficiency cleavage site described herein, digested with XbaI and BamHI.

HTLA 2C11.6 cells were transfected with OPRK-GRPR 23aa Tail -tTA fusion construct containing the low efficiency cleavage site and assays were carried out using 10 µM U-69593, an agonist for OPRK. The maximal response to U-69593 resulted in an approximately 115-fold induction of reporter gene expression over the background.

HTLA 2C11.6 cells were transfected with ADRA1A-GRPR 23aa Tail-tTA fusion construct containing the low efficiency cleavage site and assays were carried out using 10 µM epinephrine, an agonist for ADRA1A. The maximal response to epinephrine resulted in an approximately 102-fold induction of reporter gene expression over the background.

EXAMPLE 28

This experiment was designed to demonstrate the use of the assay to measure the activity of the receptor tyrosine kinase Insulin-like Growth Factor-1 Receptor (IGF1R), specifically by monitoring the ligand-induced recruitment of the intracellular signaling protein SHC1 (Src homology 2 domain-containing transforming protein 1).

A first fusion construct was created, comprising DNA encoding the human IGF-1R, which can be found at GenBank under the Accession Number NM_000875 (SEQ ID NO: 96), fused in frame to a DNA sequence encoding amino acids 3–335 of the tetracycline-controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the IGF1R coding region, and a polyA sequence was placed downstream of the tTA region. This construct is designated IGF1R-TEV-NIa-Pro cleavage (Leu)-tTA.

A second fusion construct was created, comprising DNA encoding the PTB domain of human SHC1, corresponding to amino acids 1–238 (GeneBank accession number BC014158) (SEQ ID NO: 97) fused in frame to a DNA sequence encoding the catalytic domain of mature TEV NIa protease, described supra, corresponding to amino acids 2040–2279 (GeneBank accession number AAA47910) (SEQ ID NO: 79). Inserted between these sequences is a linker DNA sequence encoding the amino acids NSGS (SEQ ID NO: 98). The CMV promoter was placed upstream of the SHC1 PTB domain coding sequence and a polyA sequence was placed downstream of the TEV NIa protease sequence. This construct is designated SHC1-TEV.

The IGF1R-TEV-NIa-Pro cleavage (Leu)-tTA and SHC1-TEV fusion constructs were transfected into clone HTL5B8.1 cells described supra. About $2.5 \times 10^4$ cells were plated into each well of a 96 well-plate, in DMEM medium supplemented with 10% fetal bovine serum, 2 mM L-Glutamine, 100 units/ml penicillin, 500 μg/ml G418, and 3 μg/ml puromycin. Cells were grown to reach 50% confluency the next day and were transfected with 15 μl per well of a mixture consisting of 100 μl of DMEM, 0.2 μg of IGF1R-TEV-NIa-Pro cleavage (Leu)-tTA DNA, 0.2 μg of SHC1-TEV DNA, and 2 μl Fugene (a proprietary transfection reagent containing lipids and other material), which had been incubated for 15 minutes at room temperature prior to addition to the cells. Transfected cells were cultured for about 16 hours before treatment with a specific receptor agonist. After 24 hours, cells were lysed and luciferase activity was assayed as described supra.

The addition of 1 μM human Insulin-like Growth Factor 1 resulted in a 90 fold increase of luciferase reporter gene activity.

EXAMPLE 29

This experiment was designed to demonstrate the use of the assay to measure the interaction of two test proteins that are not normally membrane bound. In this example, the assay was used to measure the ligand-induced dimerization of the nuclear steroid hormone receptors, ESR1 (estrogen receptor 1 or ER alpha) and ESR2 (estrogen receptor 2 or ER beta). In this example, ESR1 is fused to the transcription factor tTA, where the cleavage site for the TEV NIa-Pro protease is inserted between the ESR1 and tTA sequences. This ESR1-tTA fusion is tethered to the membrane by a fusion to the intracellular, C-terminal end of the transmembrane protein CD8. CD8 essentially serves as an inert scaffold that tethers ESR1 to the cytoplasmic side of the cell membrane. The transcription factor fused thereto cannot enter the nucleus until interaction with ESR2 and protease. Any transmembrane protein could be used. This CD8-ESR1-TEV NIa Pro cleavage-tTA fusion protein is expressed together with a second fusion protein comprised of ESR2 and the TEV NIa-Pro protease in a cell line containing a tTA-dependent reporter gene. The estrogen-induced dimerization of ESR1 and ESR2 thereby triggers the release of the tTA transcription factor from the membrane bound fusion, which is detected by the subsequent induction in reporter gene activity.

A fusion construct was created, comprising DNA encoding human CD8 gene (235 amino acids), which can be found in Genbank under Accession Number NM_001768 (SEQ ID NO: 99), fused in frame to a DNA sequence encoding the human ESR1 (596 amino acids), which can be found in Genbank under Accession Number NM_000125 (SEQ ID NO: 100). Inserted between these sequences is a DNA sequence encoding the amino acid sequence GRA (Gly-Arg-Ala). The resulting construct is then fused in frame to a DNA sequence encoding amino acids 3–335 of the tetracycline controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the Human CD8 coding region, and a poly A sequence was placed downstream of the tTA region. This construct is designated CD8-ESR1-TEV-NIa-Pro cleavage (L)-tTA.

A second fusion construct was created, using DNA encoding Human Estrogen Receptor beta (ESR2) (530 amino acids), which can be found at Genbank, under Accession Number NM_001437 (SEQ ID NO: 101), fused in frame to a DNA sequence encoding the catalytic domain of the TEV NIa protease, described supra, corresponding to amino acids 2040–2279 (GenBank accession number AAA47910) (SEQ ID NO: 84). Inserted between these sequences is a DNA sequence encoding the amino acid sequence RS (Arg-Ser). The CMV promoter region was placed upstream of the Human Estrogen Receptor beta (ESR2) coding region, and a poly A sequence was placed downstream of the TEV region. This construct is designated ESR2-TEV.

The CD8-ESR1-TEV-NIa-Pro cleavage (L)-tTA and ESR2-TEV fusion constructs, together with pCDNA3 were transiently transfected into HTL5B8.1 cells described supra. About $2.0 \times 10^4$ cells were seeded in each well of a 96 well plate and cultured in phenol-free DMEM medium supplemented with 10% fetal bovine serum., 2 mM L-glutamine, 100 units/ml penicillin, 100 μg/ml G418, and 5 μg/ml puromycin. After 24 hours of incubation, cells were transfected with a mixture of 5 ng of ESR1-TEV-Nia-Pro cleavage (L)-tTA, 15 ng of ESR2-TEV and 40 ng of pCDNA3, together with 0.3 μl Fugene per well. 6 hours after transfection, the cells were washed with PBS and incubated in 100 μl of phenol-free DMEM without serum for 24 hours before treatment with 50 nM 17-β Estradiol. Ligand-treated cells were cultured for an additional 18–20 hours before they were assayed for luciferase reporter gene activity as described supra. Treatment with 50 nM 17-β Estradiol resulted in a 16-fold increase in reporter gene activity.

Other features of the invention will be clear to the skilled artisan and need not be reiterated here.

We claim:

1. A method for determining if a test compound modulates a specific protein/protein interaction of interest, comprising contacting said compound to a cell which has been transformed or transfected with:
   (a) a first nucleic acid molecule which encodes a first, fusion protein, said first nucleic acid molecule comprising:
      (i) a nucleotide sequence which encodes a first test protein,
      (ii) a nucleotide sequence encoding a cleavage site for a protease or a portion of a protease, and
      (iii) a nucleotide sequence which encodes a protein which activates a reporter gene in said cell, and
   (b) a second nucleic acid molecule which encodes a second, fusion protein, said second nucleic acid molecule comprising:
      (i) a nucleotide sequence which encodes a second test protein whose interaction with said first test protein in the presence of said test compound is to be measured, and
      (ii) a nucleotide sequence which encodes a protease or a portion of a protease which is specific for said cleavage site,
   and determining activity of said reporter gene as a determination of whether said compound modulates said protein/protein interaction.

2. The method of claim 1, wherein said first test protein is a membrane bound protein.

3. The method of claim 1, wherein said protease or portion of a protease is tobacco etch virus nuclear inclusion A protease.

4. The method of claim 1, wherein said protein which activates said reporter gene is a transcription factor.

5. The method of claim 1, wherein said second protein is an inhibitory protein.

6. The method of claim 1, wherein said cell is a eukaryote.

7. The method of claim 1, wherein said reporter gene is an exogenous gene.

8. The method of claim 1, wherein the nucleotide sequence encoding said first test protein is modified to increase interaction with said second test protein.

9. The method of claim 1, comprising contacting more than one compound to a plurality of samples of cells, each of said samples being contacted by one or more of said compounds, wherein each of said cell samples have been transformed or transfected with (a) and (b), and determining activity of reporter genes in said plurality of said samples to determine if any of said compounds modulates said specific, protein/protein interaction.

10. The method of claim 2, wherein said membrane bound protein is a transmembrane receptor.

11. The method of claim 2, wherein said membrane bound protein is ÿ2-adrenergic receptor (ADRB2), arginine vasopressin receptor 2 (AVPR2), serotonin receptor 1a (HTR1A), m2 muscarinic acetylcholine receptor (CHRM2), chemokine (C-C motif) receptor 5 (CCR5), dopamine D2 receptor (DRD2), kappa opioid receptor (OPRK), or ADRA1A.

12. The method of claim 10, wherein said transmembrane receptor is a GPCR.

13. The method of claim 4, wherein said transcription factor is tTA or GAL4.

14. The method of claim 5, wherein said inhibitory protein is an arrestin, and said first protein is a transmembrane receptor.

15. The method of claim 7, wherein said exogenous gene encodes ÿ-galactosidase or luciferase.

16. The method of claim 8, wherein said modification comprises replacing all or part of the nucleotide sequence of the C-terminal region of said first test protein with a nucleotide sequence which encodes an amino acid sequence which has higher affinity for said second test protein than the original sequence.

17. The method of claim 16, wherein the nucleotide sequence of said C-terminal region is replaced by a nucleotide sequence encoding all or a part of the C-terminal region of AVPR2, AGTRLI, GRPR, F2PL1, CXCR2/IL-8B, CCR4, or GRPR.

18. The method of claim 9, comprising contacting each of said samples with one compound, each of which differs from all others.

19. The method of claim 9, comprising contacting each of said samples with a mixture of said compounds.

20. The method of claim 19, wherein said mixture of compounds comprises a biological sample.

21. A method for determining if a test compound modulates one or more of a plurality of protein interactions of interest, comprising contacting said test compound to a plurality of samples of cells, each of which has been transformed or transfected with
   (a) a first nucleic acid molecule which encodes a first, fusion proteins, said first nucleic acid molecule comprising:
      (i) a nucleotide sequence which encodes a first test protein,
      (ii) a nucleotide sequence encoding a cleavage site for a protease, and
      (iii) a nucleotide sequence which encodes a protein which activates a reporter gene in said cell,
   (b) a second nucleic acid molecule which encodes a second, fusion protein said second nucleic acid molecule comprising:
      (i) a nucleotide sequence which encodes a second test protein whose interaction with said first test protein in the presence of said test compound of interest is to be measured,
      (ii) a nucleotide sequence which encodes a protease or a protease which is specific for said cleavage site, wherein said first test protein differs from other first test proteins in each of said plurality of samples,
   and determining activity of said reporter gene in at one or more of said plurality of samples as a determination of modulation of one or more protein interactions of interest.

22. The method of claim 21, wherein said second test protein is different in each sample.

23. The method of claim 21, wherein said second test protein is the same in each sample.

24. The method of claim 21, wherein all of said samples are combined in a common receptacle, and each samples comprises a different pair of first and second test proteins.

25. The method of claim 21, wherein each sample is tested in a different receptacle.

26. The method of claim 21, wherein the reporter gene in a given sample differs from the reporter gene in other samples.

27. The method of claim 20, wherein said biological sample is cerebrospinal fluid, urine, blood, serum, pus, ascites, synovial fluid, a tissue extract, or an exudate.

28. A test kit useful for determining if a test compound modulates a specific protein/protein interaction of interest comprising a separate portion of each of:
  (a) a first nucleic acid molecule which encodes a first, fusion protein, said first nucleic acid molecule comprising:
    (i) a nucleotide sequence which encodes said first test protein,
    (ii) a nucleotide sequence encoding a cleavage site for a protease or a portion of a protease,
    (iii) a nucleotide sequence which encodes a protein which activates a reporter gene in said cell, and
  (b) a second nucleic acid molecule which encodes a second, fusion protein, said second nucleic acid molecule comprising:
    (i) a nucleotide sequence which encodes a second test protein whose interaction with said first test protein in the presence of said test compound is to be measured,
    (ii) a nucleotide sequence which encodes a protease or a portion of a protease which is specific for said cleavage site, and
  (c) container means for holding each of (a) and (b) separately from each other.

29. The test kit of claim 28, wherein said first test protein is a membrane bound protein.

30. The test kit of claim 28, wherein said protease or portion of a protease is tobacco etch virus nuclear inclusion A protease.

31. The test kit of claim 28, wherein said protein which activates said reporter gene is a transcription factor.

32. The test kit of claim 28, wherein said second protein is an inhibitory protein.

33. The test kit of claim 28, further comprising a separate portion of an isolated nucleic acid molecule which encodes a reporter gene.

34. The test kit of claim 28, wherein the nucleotide sequence encoding said first test protein is modified to increase interaction with said second test protein.

35. The test kit of claim 29, wherein said membrane bound protein is a transmembrane receptor.

36. The test kit of claim 29, wherein said membrane bound protein is ADRB2, AVPR2, HTR1A, CHRM2, CCR5, DRD2, or OPRK.

37. The test kit of claim 35, wherein said transmembrane receptor is a GPCR.

38. The test kit of claim 31, wherein said transcription factor is tTA or GAL4.

39. The test kit of claim 32, wherein said inhibitory protein is an arrestin, and said first protein is a transmembrane receptor.

40. The test kit of claim 33, wherein said reporter gene encodes ÿ-galactosidase or luciferase.

41. The test kit of claim 34, wherein said modification comprises replacing all or part of the nucleotide sequence of the C-terminal region of said first test protein with a nucleotide sequence which encodes an amino acid sequence which has higher affinity for said second test protein than the original sequence.

42. The test kit of claim 41, wherein said nucleotide sequence of said C-terminal region is replaced by a nucleotide sequence encoding the C-terminal region of AVPR2, AGTRLI, GRPR, F2PL1, CXCR2/IL-8B or CCR4.

* * * * *

SEQUENCE LISTING

<160> NUMBER OF SEQ ID NOS: 101

<210> SEQ ID NO 1
<211> LENGTH: 2015
<212> TYPE: DNA
<213> ORGANISM: Homo sapiens

<400> SEQUENCE: 1

```
actgcgaagc ggcttcttca gagcacgggc tggaactggc aggcaccgcg agccctagc      60
acccgacaag ctgagtgtgc aggacgagtc cccaccacac ccacaccaca gccgctgaat    120
gaggcttcca ggcgtccgct cgcggcccgc agagcccgc cgtgggtccg cccgctgagg    180
cgccccagc cagtgcgctt acctgccaga ctgcgcgcca tggggcaacc cgggaacggc     240
agcgccttct tgctggcacc caatagaagc catgcgccgg accacgacgt cacgcagcaa    300
agggacgagg tgtgggtggt gggcatgggc atcgtcatgt ctctcatcgt cctggccatc    360
gtgtttggca atgtgctggt catcacagcc attgccaagt tcgagcgtct gcagacggtc    420
accaactact tcatcacttc actggcctgt gctgatctgg tcatgggcct ggcagtggtg    480
cccttttgggg ccgcccatat tcttatgaaa atgtggactt ttggcaactt ctggtgcgag    540
ttttggactt ccattgatgt gctgtgcgtc acggccagca ttgagaccct gtgcgtgatc    600
gcagtggatc gctactttgc cattacttca cctttcaagt accagagcct gctgaccaag    660
aataaggccc gggtgatcat tctgatggtg tggattgtgt caggccttac ctccttcttg    720
cccattcaga tgcactggta ccgggccacc caccaggaag ccatcaactg ctatgccaat    780
gagacctgct gtgacttctt cacgaaccaa gcctatgcca ttgcctcttc catcgtgtcc    840
ttctacgttc ccctggtgat catggtcttc gtctactcca gggtctttca ggaggccaaa    900
aggcagctcc agaagattga caaatctgag ggccgcttcc atgtccagaa ccttagccag    960
gtggagcagg atgggcggac ggggcatgga ctccgcagat cttccaagtt ctgcttgaag   1020
gagcacaaag ccctcaagac gttaggcatc atcatgggca ctttcaccct ctgctggctg   1080
cccttcttca tcgttaacat tgtgcatgtg atccaggata acctcatccg taaggaagtt   1140
tacatcctcc taaattggat aggctatgtc aattctggtt tcaatcccct tatctactgc   1200
cggagcccag atttcaggat tgccttccag gagcttctgt gcctgcgcag gtcttctttg   1260
aaggcctatg ggaatggcta ctccagcaac ggcaacacag gggagcagag tggatatcac   1320
gtggaacagg agaaagaaaa taaactgctg tgtgaagacc tcccaggcac ggaagacttt   1380
gtgggccatc aaggtactgt gcctagcgat aacattgatt cacaagggag gaattgtagt   1440
acaaatgact cactgctgta aagcagtttt tctacttta aagacccccc cccccccaac    1500
agaacactaa acagactatt taacttgagg gtaataaaact tagaataaaa ttgtaaaaat   1560
tgtatagaga tatgcagaag gaagggcatc cttctgcctt ttttatttt ttaagctgta    1620
aaaagagaga aaacttattt gagtgattat ttgttatttg tacagttcag ttcctctttg    1680
catggaattt gtaagtttat gtctaaagag ctttagtcct agaggacctg agtctgctat    1740
attttcatga ctttttccatg tatctacctc actattcaag tattaggggt aatatattgc    1800
tgctggtaat ttgtatctga aggagatttt ccttcctaca cccttggact tgaggatttt   1860
gagtatctcg gacctttcag ctgtgaacat ggactcttcc cccactcctc ttatttgctc    1920
```

```
acacgggta ttttaggcag ggatttgagg agcagcttca gttgttttcc cgagcaaagg    1980
tctaaagttt acagtaaata aatgtttga ccatg                               2015
```

<210> SEQ ID NO 2
<211> LENGTH: 26
<212> TYPE: DNA
<213> ORGANISM: Homo Sapiens

<400> SEQUENCE: 2

```
gattgaagat ctgccttctt gctggc                                          26
```

<210> SEQ ID NO 3
<211> LENGTH: 27
<212> TYPE: DNA
<213> ORGANISM: Homo Sapiens

<400> SEQUENCE: 3

```
gcagaacttg aagacctgc ggagtcc                                          27
```

<210> SEQ ID NO 4
<211> LENGTH: 27
<212> TYPE: DNA
<213> ORGANISM: Homo Sapiens

<400> SEQUENCE: 4

```
ggactccgca ggtcttccaa gttctgc                                         27
```

<210> SEQ ID NO 5
<211> LENGTH: 27
<212> TYPE: DNA
<213> ORGANISM: Homo Sapiens

<400> SEQUENCE: 5

```
ttcggatcct agcagtgagt catttgt                                         27
```

<210> SEQ ID NO 6
<211> LENGTH: 7
<212> TYPE: PRT
<213> ORGANISM: Homo Sapiens

<400> SEQUENCE: 6

Glu Asn Leu Tyr Phe Gln Ser
            5

<210> SEQ ID NO 7
<211> LENGTH: 32
<212> TYPE: DNA
<213> ORGANISM: Homo Sapiens

<400> SEQUENCE: 7

```
ccggatcctc tagattagat aaaagtaaag tg                                   32
```

<210> SEQ ID NO 8
<211> LENGTH: 35
<212> TYPE: DNA
<213> ORGANISM: Homo Sapiens

<400> SEQUENCE: 8

```
gactcgagct agcagtatcc tcgcgccccc taccc                                35
```

<210> SEQ ID NO 9
<211> LENGTH: 18

```
<212> TYPE: DNA
<213> ORGANISM: Homo Sapiens

<400> SEQUENCE: 9
gagaacctgt acttccag                                                 18

<210> SEQ ID NO 10
<211> LENGTH: 33
<212> TYPE: DNA
<213> ORGANISM: Homo Sapiens

<400> SEQUENCE: 10
ggatccgaga acctgtactt ccagtacaga tta                                33

<210> SEQ ID NO 11
<211> LENGTH: 30
<212> TYPE: DNA
<213> ORGANISM: Homo Sapiens

<400> SEQUENCE: 11
ctcgagagat cctcgcgccc cctacccacc                                    30

<210> SEQ ID NO 12
<211> LENGTH: 7
<212> TYPE: PRT
<213> ORGANISM: Homo Sapiens

<400> SEQUENCE: 12

Glu Asn Leu Tyr Phe Gln Tyr
                5

<210> SEQ ID NO 13
<211> LENGTH: 33
<212> TYPE: DNA
<213> ORGANISM: Homo Sapiens

<400> SEQUENCE: 13
ggatccgaga acctgtactt ccagctaaga tta                                33

<210> SEQ ID NO 14
<211> LENGTH: 7
<212> TYPE: PRT
<213> ORGANISM: Homo Sapiens

<400> SEQUENCE: 14

Glu Asn Leu Tyr Phe Gln Leu
                5

<210> SEQ ID NO 15
<211> LENGTH: 33
<212> TYPE: DNA
<213> ORGANISM: Homo Sapiens

<400> SEQUENCE: 15
gcggccgcca ccatgaacgg taccgaaggc cca                                33

<210> SEQ ID NO 16
<211> LENGTH: 21
<212> TYPE: DNA
<213> ORGANISM: Homo Sapiens

<400> SEQUENCE: 16
ctggtgggtg gcccggtacc a                                             21
```

<210> SEQ ID NO 17
<211> LENGTH: 1936
<212> TYPE: DNA
<213> ORGANISM: Homo sapiens

<400> SEQUENCE: 17

```
ccccgcgtgt ctgctaggag agggcgggca gcgccgcggc gcgcgcgatc cggctgacgc      60
atctggcccc ggttccccaa gaccagagcg gggccgggag ggaggggggaa gaggcgagag    120
cgcggagggc gcgcgtgcgc attggcgcgg ggaggagcag ggatcttggc agcgggcgag    180
gaggctgcga gcgagccgcg aaccgagcgg gcggcgggcc cgcgcaccat ggggagaaa      240
cccgggacca gggtcttcaa gaagtcgagc cctaactgca agctcaccgt gtacttgggc    300
aagcgggact tcgtagatca cctggacaaa gtggaccctg tagatggcgt ggtgcttgtg    360
gaccctgact acctgaagga ccgcaaagtg tttgtgaccc tcacctgcgc cttccgctat    420
ggccgtgaag acctggatgt gctgggcttg tccttccgca agacctgtt catcgccacc      480
taccaggcct tcccccggt gcccaaccca ccccggcccc ccaccgcct gcaggaccgg        540
ctgctgagga gctgggcca gcatgccac cccttcttct tcaccatacc ccagaatctt       600
ccatgctccg tcacactgca gccaggccca gaggatacag gaaaggcctg cggcgtagac    660
tttgagattc gagccttctg tgctaaatca ctagaagaga aaagccacaa aaggaactct    720
gtgcggctgg tgatccgaaa ggtgcagttc gccccggaga acccggcc ccagccttca       780
gccgaaacca cacgccactt cctcatgtct gaccggtccc tgcacctcga ggcttccctg    840
gacaaggagc tgtactacca tggggagccc ctcaatgtaa atgtccacgt caccaacaac    900
tccaccaaga ccgtcaagaa gatcaaagtc tctgtgagac agtacgccga catctgcctc    960
ttcagcaccg cccagtacaa gtgtcctgtg gctcaactcg aacaagatga ccaggtatct  1020
cccagctcca cattctgtaa ggtgtacacc ataaccccac tgctcagcga caaccgggag  1080
aagcggggtc tcgccctgga tgggaaactc aagcacgagg acaccaacct ggcttccagc  1140
accatcgtga aggagggtgc caacaaggag gtgctgggaa tcctggtgtc ctacagggtc  1200
aaggtgaagc tggtggtgtc tcgaggcggg gatgtctctg tggagctgcc ttttgttctt  1260
atgcacccca gccccacga ccacatcccc ctccccagac cccagtcagc cgctccggag    1320
acagatgtcc ctgtggacac caacctcatt gaatttgata ccaactatgc cacagatgat  1380
gacattgtgt ttgaggactt tgcccggctt cggctgaagg ggatgaagga tgacgactat  1440
gatgatcaac tctgctagga agcggggtgg gaagaaggga ggggatgggg ttgggagagg  1500
tgagggcagg attaagatcc ccactgtcaa tgggggattg tcccagcccc tcttcccttc  1560
ccctcacctg gaagcttctt caaccaatcc cttcacactc tctcccccat cccccaaga    1620
tacacactgg accctctctt gctgaatgtg ggcattaatt ttttgactgc agctctgctt  1680
ctccagcccc gccgtgggtg gcaagctgtg ttcataccta aattttctgg aaggggacag  1740
tgaaaagagg agtgacagga gggaagggg gagacaaaac tcctactctc aacctcacac   1800
caacacctcc cattatcact ctctctgccc ccattccttc aagaggagac ctttggggga  1860
caaggccgtt tctttgtttc tgagcataaa gaagaaaata aatctttac taagcatgaa    1920
aaaaaaaaaa aaaaaa                                                   1936
```

<210> SEQ ID NO 18
<211> LENGTH: 35
<212> TYPE: DNA
<213> ORGANISM: Homo Sapiens

```
<400> SEQUENCE: 18
caggatcctc tggaatgggg gagaaacccg ggacc                                  35

<210> SEQ ID NO 19
<211> LENGTH: 30
<212> TYPE: DNA
<213> ORGANISM: Homo Sapiens

<400> SEQUENCE: 19
ggatccgcag agttgatcat catagtcgtc                                        30

<210> SEQ ID NO 20
<211> LENGTH: 9
<212> TYPE: PRT
<213> ORGANISM: Homo Sapiens

<400> SEQUENCE: 20

Tyr Pro Tyr Asp Val Pro Asp Tyr Ala
                5

<210> SEQ ID NO 21
<211> LENGTH: 28
<212> TYPE: DNA
<213> ORGANISM: Homo Sapiens

<400> SEQUENCE: 21
agatctagct tgtttaaggg accacgtg                                          28

<210> SEQ ID NO 22
<211> LENGTH: 62
<212> TYPE: DNA
<213> ORGANISM: Homo Sapiens

<400> SEQUENCE: 22
gcggccgctc aagcgtaatc tggaacatca tatgggtacg agtacaccaa ttcattcatg       60
ag                                                                      62

<210> SEQ ID NO 23
<211> LENGTH: 1809
<212> TYPE: DNA
<213> ORGANISM: Homo sapiens

<400> SEQUENCE: 23
agaagatcct gggttctgtg catccgtctg tctgaccatc cctctcaatc ttccctgccc       60
aggactggcc atactgccac cgcacacgtg cacacacgcc aacaggcatc tgccatgctg     120
gcatctctat aagggctcca gtccagagac cctgggccat tgaacttgct cctcaggcag     180
aggctgagtc cgcacatcac ctccaggccc tcagaacacc tgccccagcc ccaccatgct     240
catggcgtcc accacttccg ctgtgcctgg catccctct ctgcccagcc tgcccagcaa      300
cagcagccag gagaggccac tggacacccg gacccgctg ctagcccggg cggagctggc      360
gctgctctcc atagtctttg tggctgtggc cctgagcaat ggcctggtgc tggcggccct     420
agctcggcgg ggccggcggg ccactgggc acccatacac gtcttcattg ccacttgtg      480 cctggccgac ctggcgtgg ctctgttcca agtgctgccc cagctggcct ggaaggccac      540
cgaccgcttc cgtgggccag atgccctgtg tcgggccgtg aagtatctgc agatggtggg     600
catgtatgcc tcctcctaca tgatcctggc catgacgctg gaccgccacc gtgccatctg     660
ccgtcccatg ctggcgtacc gccatggaag tgggctcac tggaaccggc cggtgctagt      720
```

-continued

```
ggcttgggcc ttctcgctcc ttctcagcct gccccagctc ttcatcttcg cccagcgcaa      780
cgtggaaggt ggcagcgggg tcactgactg ctgggcctgc tttgcggagc cctggggccg      840
tcgcacctat gtcacctgga ttgccctgat ggtgttcgtg gcacctaccc tgggtatcgc      900
cgcctgccag gtgctcatct tccgggagat tcatgccagt ctggtgccag ggccatcaga      960
gaggcctggg gggcgccgca ggggacgccg acaggcagc cccggtgagg gagcccacgt       1020
gtcagcagct gtggccaaga ctgtgaggat gacgctagtg attgtggtcg tctatgtgct      1080
gtgctgggca cccttcttcc tggtgcagct gtgggccgcg tgggacccgg aggcacctct      1140
ggaaggggcg ccctttgtgc tactcatgtt gctggccagc ctcaacagct gcaccaaccc      1200
ctggatctat gcatctttca gcagcagcgt gtcctcagag ctgcgaagct tgctctgctg      1260
tgcccgggga cgcaccccac ccagcctggg tccccaagat gagtcctgca ccaccgccag      1320 ctcctcctg gccaaggaca cttcatcgtg aggagctgtt gggtgtcttg cctctagagg       1380
ctttgagaag ctcagctgcc ttcctggggc tggtcctggg agccactggg agggggaccc      1440
gtggagaatt ggccagagcc tgtggccccg aggctgggac actgtgtggc cctggacaag      1500
ccacagcccc tgcctgggtc tccacatccc cagctgtatg aggagagctt caggccccag      1560
gactgtgggg gcccctcagg tcagctcact gagctgggtg taggagggc tgcagcagag       1620 gcctgaggag tggcaggaaa gagggagcag gtgcccccag gtgagacagc ggtcccaggg      1680
gcctgaaaag gaaggaccag gctggggcca ggggaccttc ctgtctccgc ctttctaatc      1740
cctccctcct cattctctcc ctaataaaaa ttggagctct tttccacatg gcaagggtc       1800 tccttggaa                                                              1809
```

<210> SEQ ID NO 24
<211> LENGTH: 26
<212> TYPE: DNA
<213> ORGANISM: Homo Sapiens

<400> SEQUENCE: 24

```
gaattcatgc tcatggcgtc caccac                                            26
```

<210> SEQ ID NO 25
<211> LENGTH: 27
<212> TYPE: DNA
<213> ORGANISM: Homo Sapiens

<400> SEQUENCE: 25

```
ggatcccgat gaagtgtcct tggccag                                           27
```

<210> SEQ ID NO 26
<211> LENGTH: 1266
<212> TYPE: DNA
<213> ORGANISM: Homo sapiens

<400> SEQUENCE: 26

```
atggatgtgc tcagccctgg tcagggcaac aacaccacat caccaccggc tcccttttgag     60 accggcggca acactactgg tatctccgac gtgaccgtca gctaccaagt gatcacctct      120
ctgctgctgg gcacgctcat cttctgcgcg gtgctgggca atgcgtgcgt ggtggctgcc     180
atcgccttgg agcgctccct gcagaacgtg gccaattatc ttattggctc tttggcggtc     240
accgacctca tggtgtcggt gttggtgctg cccatggccg cgctgtatca ggtgctcaac      300
aagtggacac tgggccaggt aacctgcgac ctgttcatcg ccctcgacgt gctgtgctgc      360
```

```
acctcatcca tcttgcacct gtgcgccatc gcgctggaca ggtactgggc catcacggac      420
cccatcgact acgtgaacaa gaggacgccc cggccgcgtg cgctcatctc gctcacttgg      480
cttattggct tcctcatctc tatcccgccc atcctgggct ggcgcacccc ggaagaccgc      540 tcggacccog acgcatgcac cattagcaag gatcatggct acactatcta ttccaccttt      600
ggagctttct acatcccgct gctgctcatg ctggttctct atgggcgcat attccgagct      660
gcgcgcttcc gcatccgcaa gacggtcaaa aggtggaga agaccggagc ggacacccgc      720
catggagcat ctcccgcccc gcagcccaag aagagtgtga atggagagtc ggggagcagg      780
aactggaggc tgggcgtgga gagcaaggct ggggtgctc tgtgcgccaa tggcgcggtg      840
aggcaaggtg acgatggcgc cgccctggag gtgatcgagg tgcaccgagt gggcaactcc      900
aaagagcact tgcctctgcc cagcgaggct ggtcctaccc cttgtgcccc cgcctctttc      960
gagaggaaaa atgagcgcaa cgccgaggcg aagcgcaaga tggccctggc ccgagagagg     1020
aagacagtga agacgctggg catcatcatg ggcaccttca tcctctgctg gctgcccttc     1080
ttcatcgtgg ctcttgttct gcccttctgc gagagcagct gccacatgcc caccctgttg     1140
ggcgccataa tcaattggct gggctactcc aactctctgc ttaaccccgt catttacgca     1200
tacttcaaca aggactttca aaacgcgttt aagaagatca ttaagtgtaa cttctgccgc     1260
cagtga                                                              1266

<210> SEQ ID NO 27
<211> LENGTH: 26
<212> TYPE: DNA
<213> ORGANISM: Homo Sapiens

<400> SEQUENCE: 27
gaattcatgg atgtgctcag ccctgg                                           26

<210> SEQ ID NO 28
<211> LENGTH: 25
<212> TYPE: DNA
<213> ORGANISM: Homo Sapiens

<400> SEQUENCE: 28
ggatccctgg cggcagaact tacac                                            25

<210> SEQ ID NO 29
<211> LENGTH: 1401
<212> TYPE: DNA
<213> ORGANISM: Homo Sapiens

<400> SEQUENCE: 29
atgaataact caacaaactc ctctaacaat agcctggctc ttacaagtcc ttataagaca       60
tttgaagtgg tgtttattgt cctggtggct ggatccctca gtttggtgac cattatcggg      120
aacatcctag tcatggtttc cattaaagtc aaccgccacc tccagaccgt caacaattac      180 ttttattca gcttggcctg tgctgacctt atcataggtg ttttctccat gaacttgtac      240
accctctaca ctgtgattgg ttactggcct ttgggacctg tggtgtgtga cctttggcta      300
gccctggact atgtggtcag caatgcctca gttatgaatc tgctcatcat cagctttgac      360
aggtacttct gtgtcacaaa acctctgacc tacccagtca gcggaccac aaaaatggca      420 ggtatgatga ttgcagctgc ctgggtcctc tctttcatcc tctgggctcc agccattctc      480
ttctggcagt tcattgtagg ggtgagaact gtggaggatg gggagtgcta cattcagttt      540
ttttccaatg ctgctgtcac ctttggtacg gctattgcag ccttctattt gccagtgatc      600
```

```
atcatgactg tgctatattg gcacatatcc cgagccagca agagcaggat aaagaaggac    660
aagaaggagc ctgttgccaa ccaagacccc gtttctccaa gtctggtaca aggaaggata    720
gtgaagccaa acaataacaa catgcccagc agtgacgatg cctggagca caacaaaatc     780
cagaatggca aagcccccag ggatcctgtg actgaaaact gtgttcaggg agaggagaag    840
gagagctcca atgactccac ctcagtcagt gctgttgcct ctaatatgag agatgatgaa    900
ataacccagg atgaaaacac agtttccact tccctgggcc attccaaaga tgagaactct    960
aagcaaacat gcatcagaat tggcaccaag accccaaaaa gtgactcatg tacccaact     1020
aataccaccg tggaggtagt gggtcttca ggtcagaatg gagatgaaaa gcagaatatt     1080
gtagcccgca agattgtgaa gatgactaag cagcctgcaa aaaagaagcc tcctccttcc    1140
cgggaaaaga agtcaccag acaatcttg gctattctgt tggctttcat catcacttgg      1200
gccccataca atgtcatggt gctcattaac accttttgtg caccttgcat ccccaacact    1260
gtgtggacaa ttggttactg gctttgttac atcaacagca ctatcaaccc tgcctgctat    1320
gcactttgca atgccacctt caagaagacc tttaaacacc ttctcatgtg tcattataag    1380
aacataggcg ctacaaggta a                                              1401

<210> SEQ ID NO 30
<211> LENGTH: 27
<212> TYPE: DNA
<213> ORGANISM: Homo Sapiens

<400> SEQUENCE: 30
gaattcatga ataactcaac aaactcc                                        27

<210> SEQ ID NO 31
<211> LENGTH: 25
<212> TYPE: DNA
<213> ORGANISM: Homo Sapiens

<400> SEQUENCE: 31
agatctcctt gtagcgccta tgttc                                          25

<210> SEQ ID NO 32
<211> LENGTH: 3655
<212> TYPE: DNA
<213> ORGANISM: Homo sapiens

<400> SEQUENCE: 32
cttcagatag attatatctg gagtgaagga tcctgccacc tacgtatctg gcatagtatt    60
ctgtgtagtg ggatgagcag agaacaaaaa caaaataatc cagtgagaaa agcccgtaaa    120
taaaccttca gaccagagat ctattctcca gcttatttta agctcaactt aaaaagaaga    180
actgttctct gattcttttc gccttcaata cacttaatga tttaactcca ccctccttca    240
aaagaaacag catttcctac ttttatactg tctatatgat tgatttgcac agctcatctg    300
gccagaagag ctgagacatc cgttccccta caagaaactc tccccgggtg aacaagatg     360
gattatcaag tgtcaagtcc aatctatgac atcaattatt atacatcgga gccctgccaa    420
aaaatcaatg tgaagcaaat cgcagcccgc ctcctgcctc cgctctactc actggtgttc    480
atctttggtt ttgtgggcaa catgctggtc atcctcatcc tgataaactg caaaaggctg    540
aagagcatga ctgacatcta cctgctcaac ctggccatct ctgacctgtt tttccttctt    600
actgtcccct tctgggctca ctatgctgcc gcccagtggg actttggaaa tacaatgtgt    660
```

| | |
|---|---:|
| caactcttga cagggctcta ttttataggc ttcttctctg gaatcttctt catcatcctc | 720 |
| ctgacaatcg ataggtacct ggctgtcgtc catgctgtgt ttgctttaaa agccaggacg | 780 |
| gtcacctttg gggtggtgac aagtgtgatc acttgggtgg tggctgtgtt tgcgtctctc | 840 |
| ccaggaatca tctttaccag atctcaaaaa gaaggtcttc attacacctg cagctctcat | 900 |
| tttccataca gtcagtatca attctggaag aatttccaga cattaaagat agtcatcttg | 960 |
| gggctggtcc tgccgctgct tgtcatggtc atctgctact cgggaatcct aaaaactctg | 1020 |
| cttcggtgtc gaaatgagaa gaagaggcac agggctgtga ggcttatctt caccatcatg | 1080 |
| attgtttatt ttctcttctg ggctccctac aacattgtcc ttctcctgaa cacctttccag | 1140 |
| gaattctttg gcctgaataa ttgcagtagc tctaacaggt tggaccaagc tatgcaggtg | 1200 |
| acagagactc ttgggatgac gcactgctgc atcaacccca tcatctatgc ctttgtcggg | 1260 |
| gagaagttca gaaactacct cttagtcttc ttccaaaagc acattgccaa acgcttctgc | 1320 |
| aaatgctgtt ctattttcca gcaagaggct cccgagcgag caagctcagt ttacacccga | 1380 |
| tccactgggg agcaggaaat atctgtgggc ttgtgacacg gactcaagtg ggctggtgac | 1440 |
| ccagtcagag ttgtgcacat ggcttagttt tcatacacag cctgggctgg gggtggggtg | 1500 |
| ggagaggtct tttttaaaag gaagttactg ttatagaggg tctaagattc atccatttat | 1560 |
| ttggcatctg tttaaagtag attagatctt ttaagcccat caattataga aagccaaatc | 1620 |
| aaaatatgtt gatgaaaaat agcaacccttt ttatctcccc ttcacatgca tcaagttatt | 1680 |
| gacaaactct cccttcactc cgaaagttcc ttatgtatat ttaaaagaaa gcctcagaga | 1740 |
| attgctgatt cttgagttta gtgatctgaa cagaaatacc aaaattattt cagaaatgta | 1800 |
| caacttttta cctagtacaa ggcaacatat aggttgtaaa tgtgtttaaa acaggtctttt | 1860 |
| gtcttgctat ggggagaaaa gacatgaata tgattagtaa agaaatgaca cttttcatgt | 1920 |
| gtgatttccc ctccaaggta tggttaataa gtttcactga cttagaacca ggcgagagac | 1980 |
| ttgtggcctg ggagagctgg ggaagcttct taaatgagaa ggaatttgag ttggatcatc | 2040 |
| tattgctggc aaagacagaa gcctcactgc aagcactgca tgggcaagct ggctgtaga | 2100 |
| aggagacaga gctggttggg aagacatggg gaggaaggac aaggctagat catgaagaac | 2160 |
| cttgacggca ttgctccgtc taagtcatga gctgagcagg gagatcctgg ttggtgttgc | 2220 |
| agaaggttta ctctgtggcc aaaggagggt caggaaggat gagcatttag ggcaaggaga | 2280 |
| ccaccaacag ccctcaggtc agggtgagga tggcctctgc taagctcaag gcgtgaggat | 2340 |
| gggaaggagg gaggtattcg taaggatggg aaggaggag gtattcgtgc agcatatgag | 2400 |
| gatgcagagt cagcagaact ggggtggatt tggtttggaa gtgagggtca gagaggagtc | 2460 |
| agagagaatc cctagtcttc aagcagattg gagaaaccct tgaaaagaca tcaagcacag | 2520 |
| aaggaggagg aggaggttta ggtcaagaag aagatggatt ggtgtaaaag gatgggtctg | 2580 |
| gtttgcagag cttgaacaca gtctcaccca gactccaggc tgtctttcac tgaatgcttc | 2640 |
| tgacttcata gatttccttc ccatcccagc tgaaatactg aggggtctcc aggaggagac | 2700 |
| tagatttatg aatacacgag gtatgaggtc taggaacata cttcagctca cacatgagat | 2760 |
| ctaggtgagg attgattacc tagtagtcat ttcatggggtt gttgggagga ttctatgagg | 2820 |
| caaccacagg cagcatttag cacatactac acattcaata agcatcaaac tcttagttac | 2880 |
| tcattcaggg atagcactga gcaaagcatt gagcaaaggg gtcccatata ggtgagggaa | 2940 |
| gcctgaaaaa ctaagatgct gcctgcccag tgcacacaag tgtaggtatc attttctgca | 3000 |
| tttaaccgtc aataggcaaa ggggggaagg gacatattca tttggaaata agctgccttg | 3060 |

-continued

```
agccttaaaa cccacaaaag tacaatttac cagcctccgt atttcagact gaatgggggt    3120
ggggggggcg ccttaggtac ttattccaga tgccttctcc agacaaacca gaagcaacag    3180
aaaaaatcgt ctctccctcc ctttgaaatg aatatacccc ttagtgtttg ggtatattca    3240
tttcaaaggg agagagagag gttttttttct gttctttctc atatgattgt gcacatactt    3300
gagactgttt tgaatttggg ggatggctaa aaccatcata gtacaggtaa ggtgagggaa    3360
tagtaagtgg tgagaactac tcagggaatg aaggtgtcag aataataaga ggtgctactg    3420
actttctcag cctctgaata tgaacggtga gcattgtggc tgtcagcagg aagcaacgaa    3480
gggaaatgtc tttccttttg ctcttaagtt gtggagagtg caacagtagc ataggaccct    3540
accctctggg ccaagtcaaa gacattctga catcttagta tttgcatatt cttatgtatg    3600
tgaaagttac aaattgcttg aaagaaaata tgcatctaat aaaaaacacc ttcta         3655
```

<210> SEQ ID NO 33
<211> LENGTH: 31
<212> TYPE: DNA
<213> ORGANISM: Homo Sapiens

<400> SEQUENCE: 33

```
gcggccgcat ggattatcaa gtgtcaagtc c                                    31
```

<210> SEQ ID NO 34
<211> LENGTH: 25
<212> TYPE: DNA
<213> ORGANISM: Homo Sapiens

<400> SEQUENCE: 34

```
ggatccctgg cggcagaact tacac                                           25
```

<210> SEQ ID NO 35
<211> LENGTH: 33
<212> TYPE: DNA
<213> ORGANISM: Homo Sapiens

<400> SEQUENCE: 35

```
ggtctccaat tcatggatta tcaagtgtca agt                                  33
```

<210> SEQ ID NO 36
<211> LENGTH: 21
<212> TYPE: DNA
<213> ORGANISM: Homo Sapiens

<400> SEQUENCE: 36

```
gacgacagcc aggtacctat c                                               21
```

<210> SEQ ID NO 37
<211> LENGTH: 2643
<212> TYPE: DNA
<213> ORGANISM: Homo sapiens

<400> SEQUENCE: 37

```
ggcagccgtc cggggccgcc actctcctcg gccggtccct ggctcccgga ggcggccgcg    60
cgtggatgcg gcgggagctg gaagcctcaa gcagccggcg ccgtctctgc ccgggggcgc   120
cctatggctt gaagagcctg gccacccagt ggctccaccg ccctgatgga tccactgaat   180
ctgtcctggt atgatgatga tctggagagg cagaactgga gccggccctt caacgggtca   240
gacgggaagg cggacagacc ccactacaac tactatgcca cactgctcac cctgctcatc   300
```

```
gctgtcatcg tcttcggcaa cgtgctggtg tgcatggctg tgtcccgcga gaaggcgctg     360
cagaccacca ccaactacct gatcgtcagc ctcgcagtgg ccgacctcct cgtcgccaca     420
ctggtcatgc cctgggttgt ctacctggag gtggtaggtg agtggaaatt cagcaggatt     480
cactgtgaca tcttcgtcac tctggacgtc atgatgtgca cggcgagcat cctgaacttg     540
tgtgccatca gcatcgacag gtacacagct gtggccatgc ccatgctgta caatacgcgc     600
tacagctcca agcgccgggt caccgtcatg atctccatcg tctgggtcct gtccttcacc     660
atctcctgcc cactcctctt cggactcaat aacgcagacc agaacgagtg catcattgcc     720
aacccggcct tcgtggtcta ctcctccatc gtctccttct acgtgccctt cattgtcacc     780
ctgctggtct acatcaagat ctacattgtc ctccgcagac gccgcaagcg agtcaacacc     840
aaacgcagca gccgagcttt cagggcccac ctgagggctc cactaaaggg caactgtact     900
caccccgagg acatgaaact ctgcaccgtt atcatgaagt ctaatgggag tttcccagtg     960
aacaggcgga gagtggaggc tgcccggcga gcccaggagc tggagatgga gatgctctcc    1020
agcaccagcc cacccgagag gacccggtac agccccatcc cacccagcca ccaccagctg    1080
actctccccg acccgtccca ccatggtctc cacagcactc ccgacagccc cgccaaacca    1140
gagaagaatg ggcatgccaa agaccacccc aagattgcca agatctttga gatccagacc    1200
atgcccaatg gcaaaacccg gacctccctc aagaccatga gccgtaggaa gctctcccag    1260
cagaaggaga agaaagccac tcagatgctc gccattgttc tcggcgtgtt catcatctgc    1320
tggctgccct tcttcatcac acacatcctg aacatacact gtgactgcaa catcccgcct    1380
gtcctgtaca gcgccttcac gtggctgggc tatgtcaaca gcgccgtgaa ccccatcatc    1440
tacaccacct tcaacattga gttccgcaag gccttcctga agatcctcca ctgctgactc    1500
tgctgcctgc ccgcacagca gcctgcttcc cacctccctg cccaggccgg ccagcctcac    1560
ccttgcgaac cgtgagcagg aaggcctggg tggatcggcc tcctcttcac cccggcaggc    1620
cctgcagtgt tcgcttggct ccatgctcct cactgcccgc acaccctcac tctgccaggg    1680
cagtgctagt gagctgggca tggtaccagc cctggggctg ggccccccag ctcaggggca    1740
gctcatagag tccccctcc cacctccagt ccccctatcc ttggcaccaa agatgcagcc    1800
gccttccttg accttcctct ggggctctag ggttgctgga gcctgagtca gggcccagag    1860
gctgagtttt ctctttgtgg ggcttggcgt ggagcaggcg gtggggagag atggacagtt    1920
cacaccctgc aaggcccaca ggaggcaagc aagctctctt gccgaggagc caggcaactt    1980
cagtcctggg agacccatgt aaataccaga ctgcaggttg accccagag attcccaagc     2040 caaaaccttt agctccctcc cgcacccga tgtggacctc tactttccag gctagtccgg    2100
acccacctca ccccgttaca gctccccaag tggtttccac atgctctgag aagaggagcc    2160
ctcatcttga agggcccagg agggtctatg gggagaggaa ctccttggcc tagcccaccc    2220
tgctgccttc tgacgcccct gcaatgtatc ccttctcaca gcacatgctg ccagcctggg    2280
ggcctggcag ggaggtcagg ccctggaact ctatctgggc ctgggctagg ggacatcaga    2340
ggttctttga gggactgcct ctgccacact ctgacgcaaa accactttcc ttttctattc    2400
cttctggcct ttcctctctc ctgtttccct tcccttccac tgcctctgcc ttagaggagc    2460
ccacggctaa gaggctgctg aaaaccatct ggcctggcct ggccctgccc tgaggaagga    2520
ggggaagctg cagcttggga gagcccctgg ggcctagact ctgtaacatc actatccatg    2580 caccaaaacta ataaaacttt gacgagtcac cttccaggac ccctgggtaa aaaaaaaaaa    2640
aaa                                                                   2643
```

<210> SEQ ID NO 38
<211> LENGTH: 27
<212> TYPE: DNA
<213> ORGANISM: Homo Sapiens

<400> SEQUENCE: 38

```
gaattcatgg atccactgaa tctgtcc                                           27
```

<210> SEQ ID NO 39
<211> LENGTH: 25
<212> TYPE: DNA
<213> ORGANISM: Homo Sapiens

<400> SEQUENCE: 39

```
agatctgcag tggaggatct tcagg                                             25
```

<210> SEQ ID NO 40
<211> LENGTH: 1301
<212> TYPE: DNA
<213> ORGANISM: Homo sapiens

<400> SEQUENCE: 40

```
atgggcgaca aagggacgcg agtgttcaag aaggccagtc caaatggaaa gctcaccgtc        60
tacctgggaa agcggactt tgtggaccac atcgacctcg tggaccctgt ggatggtgtg       120
gtcctggtgg atcctgagta tctcaaagag cggagagtct atgtgacgct gacctgcgcc      180
ttccgctatg ccgggagga cctggatgtc ctgggcctga cctttcgcaa ggacctgttt       240
gtggccaacg tacagtcgtt cccaccggcc cccgaggaca agaagcccct gacgcggctg      300
caggaacgcc tcatcaagaa gctgggcgag cacgcttacc ctttcacctt tgagatccct      360
ccaaaccttc catgttctgt gacactgcag ccggggcccg aagacacggg gaaggcttgc      420
ggtgtggact atgaagtcaa agccttctgc gcggagaatt tggaggagaa gatccacaag      480
cggaattctg tgcgtctggt catccggaag gttcagtatg ccccagagag gcctggcccc      540
cagcccacag ccgagaccac caggcagttc ctcatgtcgg acaagccctt gcacctagaa      600
gcctctctgg ataaggagat ctattaccat ggagaaccca tcagcgtcaa cgtccacgtc      660
accaacaaca ccaacaagac ggtgaagaag atcaagatct cagtgcgcca gtatgcagac      720
atctgccttt tcaacacagc tcagtacaag tgccctgttg ccatggaaga ggctgatgac      780
actgtggcac ccagctcgac gttctgcaag gtctacacac tgacccccett cctagccaat      840
aaccgagaga gcggggcct cgccttggac gggaagctca agcacgaaga cacgaacttg      900
gcctctagca ccctgttgag ggaaggtgcc aaccgtgaga tcctggggat cattgtttcc      960
tacaaagtga agtgaagct ggtggtgtct cggggcggcc tgttgggaga tcttgcatcc     1020
agcgacgtgg ccgtggaact gcccttcacc ctaatgcacc ccaagcccaa agaggaaccc     1080
ccgcatcggg aagttccaga gaacgagacg ccagtagata ccaatctcat agaacttgac     1140
acaaatgatg acgacattgt atttgaggac tttgctcgcc agagactgaa aggcatgaag     1200
gatgacaagg aggaagagga ggatggtacc ggctctccac agctcaacaa cagatagacg     1260
ggccggccct gcctccacgt ggctccggct ccactctcgt g                         1301
```

<210> SEQ ID NO 41
<211> LENGTH: 30
<212> TYPE: DNA
<213> ORGANISM: Homo Sapiens

```
<400> SEQUENCE: 41
ggtaccatgg gcgacaaagg gacgcgagtg                                      30

<210> SEQ ID NO 42
<211> LENGTH: 48
<212> TYPE: DNA
<213> ORGANISM: Homo Sapiens

<400> SEQUENCE: 42
ggatcctctg ttgttgagct gtggagagcc tgtaccatcc tcctcttc                  48

<210> SEQ ID NO 43
<211> LENGTH: 27
<212> TYPE: DNA
<213> ORGANISM: Homo Sapiens

<400> SEQUENCE: 43
ggatccattt gtgtcaagtt ctatgag                                         27

<210> SEQ ID NO 44
<211> LENGTH: 27
<212> TYPE: DNA
<213> ORGANISM: Homo Sapiens

<400> SEQUENCE: 44
ggtaccatgg gggagaaacc cgggacc                                         27

<210> SEQ ID NO 45
<211> LENGTH: 24
<212> TYPE: DNA
<213> ORGANISM: Homo Sapiens

<400> SEQUENCE: 45
ggatcctgtg gcatagttgg tatc                                            24

<210> SEQ ID NO 46
<211> LENGTH: 33
<212> TYPE: DNA
<213> ORGANISM: Homo Sapiens

<400> SEQUENCE: 46
tgtgcgcgcg gacgcacccc acccagcctg ggt                                  33

<210> SEQ ID NO 47
<211> LENGTH: 27
<212> TYPE: DNA
<213> ORGANISM: Homo Sapiens

<400> SEQUENCE: 47
gaattcatgg atccactgaa tctgtcc                                         27

<210> SEQ ID NO 48
<211> LENGTH: 33
<212> TYPE: DNA
<213> ORGANISM: Homo Sapiens

<400> SEQUENCE: 48
tgtgcgcgcg cagtggagga tcttcaggaa ggc                                  33

<210> SEQ ID NO 49
<211> LENGTH: 33
<212> TYPE: DNA
<213> ORGANISM: Homo Sapiens
```

<400> SEQUENCE: 49
gcggccgcca ccatgaacgg taccgaaggc cca          33

<210> SEQ ID NO 50
<211> LENGTH: 30
<212> TYPE: DNA
<213> ORGANISM: Homo Sapiens

<400> SEQUENCE: 50
tgtgcgcgcg cacagaagct cctggaaggc          30

<210> SEQ ID NO 51
<211> LENGTH: 1602
<212> TYPE: DNA
<213> ORGANISM: Homo sapiens

<400> SEQUENCE: 51
gagctccgtg ctgggaggtg ggaaggggc ttgaccctgg ggactcaggc agtctgggga          60
cagttccacc aggggccggt gcctagaatt ggtgagggag gcacctcagg ggctggggga         120
gaaggaacga gcgctcttcg cccctctctg gcacccagcg gcgcgcctgc tggccggaaa         180
ggcagcgaga agtccgttct ccctgtcctg ccccggcga cttgcggccc gggtgggagt         240
ccgcaggctc cgggtcccca gcgccgctgg ccagggcgcg ggcaaagttt gcctctccgc         300
gtccagccgg ttctttcgct cccgcagcgc gcaggtgcc gcctgtcctc gccttcctgc         360
tgcaatcgcc ccaccatgga ctccccgatc cagatcttcc gcggggagcc gggccctacc         420
tgcgccccga gcgcctgcct gccccccaac agcagcgcct ggtttccgg ctgggccgag          480
cccgacagca acggcagcgc cggctcggag gacgcgcagc tggagcccgc gcacatctcc         540
ccggccatcc cggtcatcat cacggcggtc tactccgtag tgttcgtcgt gggcttggtg         600
ggcaactcgc tggtcatgtt cgtgatcatc cgatacacaa agatgaagac agcaaccaac         660
atttacatat ttaacctggc tttggcagat gctttagtta ctacaaccat gcccttcag          720
agtacggtct acttgatgaa ttcctggcct tttgggatg tgctgtgcaa gatagtaatt         780
tccattgatt actacaacat gttccaccag atcttcacct tgaccatgat gagcgtggac         840
cgctacattg ccgtgtgcca ccccgtgaag gctttggact ccgcacacac cttgaaggca         900
aagatcatca atatctgcat ctggctgctg tcgtcatctg ttggcatctc tgcaatagtc         960
cttggaggca ccaaagtcag ggaagacgtc gatgtcattg agtgctcctt gcagttccca        1020
gatgatgact actcctggtg ggacctcttc atgaagatct gcgtcttcat ctttgccttc        1080
gtgatccctg tcctcatcat catcgtctgc tacacccctg atcctgcg tctcaagagc         1140
gtccggctcc tttctggctc ccgagagaaa gatcgcaacc tgcgtaggat caccagactg        1200
gtcctggtgg tggtggcagt cttcgtcgtc tgctggactc ccattcacat attcatcctg        1260
gtggaggctc tggggagcac ctcccacagc acagctgctc tctccagcta ttacttctgc        1320
atcgccttag ctataccaa cagtagcctg aatcccattc tctacgcctt tcttgatgaa        1380
aacttcaagc ggtgtttccg ggacttctgc tttccactga agatgaggat ggagcggcag        1440
agcactagca gagtccgaaa tacagttcag gatcctgctt acctgaggga catcgatggg        1500
atgaataaac cagtatgact agtcgtggag atgtcttcgt acagttcttc gggaagagag        1560
gagttcaatg atctaggttt aactcagatc actactgcag tc                           1602

<210> SEQ ID NO 52

```
<211> LENGTH: 24
<212> TYPE: DNA
<213> ORGANISM: Homo Sapiens

<400> SEQUENCE: 52
ggtctacttg atgaattcct ggcc                                              24

<210> SEQ ID NO 53
<211> LENGTH: 27
<212> TYPE: DNA
<213> ORGANISM: Homo Sapiens

<400> SEQUENCE: 53
gcgcgcacag aagtcccgga aacaccg                                           27

<210> SEQ ID NO 54
<211> LENGTH: 10
<212> TYPE: PRT
<213> ORGANISM: Homo Sapiens

<400> SEQUENCE: 54

Gly Ser Glu Asn Leu Tyr Phe Gln Leu Arg
                5                  10

<210> SEQ ID NO 55
<211> LENGTH: 881
<212> TYPE: PRT
<213> ORGANISM: Homo sapiens

<400> SEQUENCE: 55

Met Lys Leu Leu Ser Ser Ile Glu Gln Ala Cys Asp Ile Cys Arg Leu
                5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
            180                 185                 190

Asn Asn Gly Phe Phe Gly Asp Gly Ser Leu Leu Cys Ile Leu Arg Ser
        195                 200                 205

Ile Gly Phe Lys Pro Glu Asn Tyr Thr Asn Ser Asn Val Asn Arg Leu
    210                 215                 220
```

-continued

```
Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
            245                 250                 255

Ile Val His Ser Pro Thr Leu Met Met Leu Tyr Asn Asn Gln Ile Glu
        260                 265                 270

Ile Ala Ser Lys Asp Gln Trp Gln Ile Leu Phe Asn Cys Ile Leu Ala
    275                 280                 285

Ile Gly Ala Trp Cys Ile Glu Gly Glu Ser Thr Asp Ile Asp Val Phe
290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
            325                 330                 335

Gln Trp Arg Gln Lys Thr Asn Thr Ser Tyr Asn Phe His Ser Phe Ser
        340                 345                 350

Ile Arg Met Ala Ile Ser Leu Gly Leu Asn Arg Asp Leu Pro Ser Ser
    355                 360                 365

Phe Ser Asp Ser Ser Ile Leu Glu Gln Arg Arg Ile Trp Trp Ser
370                 375                 380

Val Tyr Ser Trp Glu Ile Gln Leu Ser Leu Leu Tyr Gly Arg Ser Ile
385                 390                 395                 400

Gln Leu Ser Gln Asn Thr Ile Ser Phe Pro Ser Ser Val Asp Asp Val
            405                 410                 415

Gln Arg Thr Thr Thr Gly Pro Thr Ile Tyr His Gly Ile Ile Glu Thr
        420                 425                 430

Ala Arg Leu Leu Gln Val Phe Thr Lys Ile Tyr Glu Leu Asp Lys Thr
    435                 440                 445

Val Thr Ala Glu Lys Ser Pro Ile Cys Ala Lys Lys Cys Leu Met Ile
450                 455                 460

Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
            485                 490                 495

Trp Leu Ser Phe Thr Arg Phe Glu Leu Lys Trp Lys Gln Leu Ser Leu
        500                 505                 510

Ile Ile Tyr Val Leu Arg Asp Phe Phe Thr Asn Phe Thr Gln Lys Lys
    515                 520                 525

Ser Gln Leu Glu Gln Asp Gln Asn Asp His Gln Ser Tyr Glu Val Lys
530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
            565                 570                 575

Asn Cys Ser Tyr Tyr Leu Phe Asn Ala Val Leu Val Pro Ile Lys Thr
        580                 585                 590

Leu Leu Ser Asn Ser Lys Ser Asn Ala Glu Asn Glu Thr Ala Gln
    595                 600                 605

Leu Leu Gln Gln Ile Asn Thr Val Leu Met Leu Leu Lys Lys Leu Ala
610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
```

-continued

```
                    645                 650                 655
Ile Ser Tyr Asn Asn Ser Asn Gly Ser Ala Ile Lys Asn Ile Val Gly
                660                 665                 670

Ser Ala Thr Ile Ala Gln Tyr Pro Thr Leu Pro Glu Glu Asn Val Asn
            675                 680                 685

Asn Ile Ser Val Lys Tyr Val Ser Pro Gly Ser Val Gly Pro Ser Pro
690                 695                 700

Val Pro Leu Lys Ser Gly Ala Ser Phe Ser Asp Leu Val Lys Leu Leu
705                 710                 715                 720

Ser Asn Arg Pro Pro Ser Arg Asn Ser Pro Val Thr Ile Pro Arg Ser
                725                 730                 735

Thr Pro Ser His Arg Ser Val Thr Pro Phe Leu Gly Gln Gln Gln Gln
            740                 745                 750

Leu Gln Ser Leu Val Pro Leu Thr Pro Ser Ala Leu Phe Gly Gly Ala
        755                 760                 765

Asn Phe Asn Gln Ser Gly Asn Ile Ala Asp Ser Ser Leu Ser Phe Thr
    770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Asn Val His Asp Asn
                805                 810                 815

Phe Met Asn Asn Glu Ile Thr Ala Ser Lys Ile Asp Asp Gly Asn Asn
            820                 825                 830

Ser Lys Pro Leu Ser Pro Gly Trp Thr Asp Gln Thr Ala Tyr Asn Ala
        835                 840                 845

Phe Gly Ile Thr Thr Gly Met Phe Asn Thr Thr Met Asp Asp Val
    850                 855                 860

Tyr Asn Tyr Leu Phe Asp Asp Glu Asp Thr Pro Pro Asn Pro Lys Lys
865                 870                 875                 880

Glu
```

<210> SEQ ID NO 56
<211> LENGTH: 13
<212> TYPE: PRT
<213> ORGANISM: Homo Sapiens

<400> SEQUENCE: 56

```
Pro Gln Lys Gly Ser Ala Ser Glu Lys Thr Met Val Phe
                5                   10
```

<210> SEQ ID NO 57
<211> LENGTH: 549
<212> TYPE: PRT
<213> ORGANISM: Homo sapiens

<400> SEQUENCE: 57

```
Met Asp Asp Leu Phe Pro Leu Ile Phe Pro Ser Glu Pro Ala Gln Ala
                5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80
```

```
Pro Pro His Arg Pro His Pro His Glu Leu Val Gly Lys Asp Cys Arg
                85                  90                  95
Asp Gly Tyr Tyr Glu Ala Asp Leu Cys Pro Asp Arg Ser Ile His Ser
            100                 105                 110
Phe Gln Asn Leu Gly Ile Gln Cys Val Lys Lys Arg Asp Leu Glu Gln
        115                 120                 125
Ala Ile Ser Gln Arg Ile Gln Thr Asn Asn Pro Phe His Val Pro
    130                 135                 140
Ile Glu Glu Gln Arg Gly Asp Tyr Asp Leu Asn Ala Val Arg Leu Cys
145                 150                 155                 160
Phe Gln Val Thr Val Arg Asp Pro Ala Gly Arg Pro Leu Leu Leu Thr
                165                 170                 175
Pro Val Leu Ser His Pro Ile Phe Asp Asn Arg Ala Pro Asn Thr Ala
            180                 185                 190
Glu Leu Lys Ile Cys Arg Val Asn Arg Asn Ser Gly Ser Cys Leu Gly
        195                 200                 205
Gly Asp Glu Ile Phe Leu Leu Cys Asp Lys Val Gln Lys Glu Asp Ile
    210                 215                 220
Glu Val Tyr Phe Thr Gly Pro Gly Trp Glu Ala Arg Gly Ser Phe Ser
225                 230                 235                 240
Gln Ala Asp Val His Arg Gln Val Ala Ile Val Phe Arg Thr Pro Pro
                245                 250                 255
Tyr Ala Asp Pro Ser Leu Gln Ala Pro Val Arg Val Ser Met Gln Leu
            260                 265                 270
Arg Arg Pro Ser Asp Arg Glu Leu Ser Glu Pro Met Glu Phe Gln Tyr
        275                 280                 285
Leu Pro Asp Thr Asp Asp Arg His Arg Ile Glu Glu Lys Arg Lys Arg
    290                 295                 300
Thr Tyr Glu Thr Phe Lys Ser Ile Met Lys Lys Ser Pro Phe Asn Gly
305                 310                 315                 320
Pro Thr Glu Pro Arg Pro Pro Thr Arg Arg Ile Ala Val Pro Thr Arg
                325                 330                 335
Asn Ser Thr Ser Val Pro Lys Pro Ala Pro Gln Pro Tyr Thr Phe Pro
            340                 345                 350
Ala Ser Leu Ser Thr Ile Asn Phe Asp Glu Phe Ser Pro Met Leu Leu
        355                 360                 365
Pro Ser Gly Gln Ile Ser Asn Gln Ala Leu Ala Leu Ala Pro Ser Ser
    370                 375                 380
Ala Pro Val Leu Ala Gln Thr Met Val Pro Ser Ser Ala Met Val Pro
385                 390                 395                 400
Leu Ala Gln Pro Pro Ala Pro Ala Pro Val Leu Thr Pro Gly Pro Pro
                405                 410                 415
Gln Ser Leu Ser Ala Pro Val Pro Lys Ser Thr Gln Ala Gly Glu Gly
            420                 425                 430
Thr Leu Ser Glu Ala Leu Leu His Leu Gln Phe Asp Ala Asp Glu Asp
        435                 440                 445
Leu Gly Ala Leu Leu Gly Asn Ser Thr Asp Pro Gly Val Phe Thr Asp
    450                 455                 460
Leu Ala Ser Val Asp Asn Ser Glu Phe Gln Gln Leu Leu Asn Gln Gly
465                 470                 475                 480
Val Ser Met Ser His Ser Thr Ala Glu Pro Met Leu Met Glu Tyr Pro
                485                 490                 495
```

```
Glu Ala Ile Thr Arg Leu Val Thr Gly Ser Gln Arg Pro Pro Asp Pro
            500                 505                 510
Ala Pro Thr Pro Leu Gly Thr Ser Gly Leu Pro Asn Gly Leu Ser Gly
        515                 520                 525
Asp Glu Asp Phe Ser Ser Ile Ala Asp Met Asp Phe Ser Ala Leu Leu
    530                 535                 540
Ser Gln Ile Ser Ser
545
```

<210> SEQ ID NO 58
<211> LENGTH: 1833
<212> TYPE: DNA
<213> ORGANISM: Homo sapiens

<400> SEQUENCE: 58

| | | |
|---|---|---|
| ggaggtggga ggagggagtg acgagtcaag gaggagacag ggacgcagga gggtgcaagg | 60 |
| aagtgtctta actgagacgg gggtaaggca agagagggtg gaggaaattc tgcaggagac | 120 |
| aggcttcctc cagggtctgg agaacccaga ggcagctcct cctgagtgct gggaaggact | 180 |
| ctgggcatct tcagcccttc ttactctctg aggctcaagc cagaaattca ggctgcttgc | 240 |
| agagtgggtg acagagccac ggagctggtg tccctgggac cctctgcccg tcttctctcc | 300 |
| actccccagc atgaggaag gtggtgattt tgacaactac tatggggcag acaaccagtc | 360 |
| tgagtgtgag tacacagact ggaaatcctc gggggccctc atccctgcca tctacatgtt | 420 |
| ggtcttcctc ctgggcacca cgggcaacgg tctggtgctc tggaccgtgt tcggagcag | 480 |
| ccgggagaag aggcgctcag ctgatatctt cattgctagc ctggcggtgg ctgacctgac | 540 |
| cttcgtggtg acgctgcccc tgtgggctac ctacacgtac cgggactatg actggccctt | 600 |
| tgggaccttc ttctgcaagc tcagcagcta cctcatcttc gtcaacatgt acgccagcgt | 660 |
| cttctgcctc accggcctca gcttcgaccg ctacctggcc atcgtgaggc cagtggccaa | 720 |
| tgctcggctg aggctgcggg tcagcggggc cgtggccacg gcagttcttt gggtgctggc | 780 |
| cgccctcctg gccatgcctg tcatggtgtt acgcaccacc ggggacttgg agaacaccac | 840 |
| taaggtgcag tgctacatgg actactccat ggtggccact gtgagctcag agtgggcctg | 900 |
| ggaggtgggc cttggggtct cgtccaccac cgtgggcttt gtggtgccct tcaccatcat | 960 |
| gctgacctgt tacttcttca tcgcccaaac catcgctggc cacttccgca aggaacgcat | 1020 |
| cgagggcctg cggaagcggc gccggctgct cagcatcatc gtggtgctgg tggtgacctt | 1080 |
| tgccctgtgc tggatgccct accacctggt gaagacgctg tacatgctgg gcagcctgct | 1140 |
| gcactgcccc tgtgactttg acctcttcct catgaacatc ttccctact gcacctgcat | 1200 |
| cagctacgtc aacagctgcc tcaacccctt cctctatgcc ttttcgacc ccgcttccg | 1260 |
| ccaggcctgc acctccatgc tctgctgtgg ccagagcagg tgcgcaggca cctcccacag | 1320 |
| cagcagtggg gagaagtcag ccagctactc ttcggggcac agccagggc ccggccccaa | 1380 |
| catgggcaag ggtggagaac agatgcacga gaaatccatc ccctacagcc aggagaccct | 1440 |
| tgtggttgac tagggctggg agcagagaga agcctggcgc cctcggccct ccccggcctt | 1500 |
| tgcccttgct ttctgaaaat cagagtcacc tcctctgccc agagctgtcc tcaaagcatc | 1560 |
| cagtgaacac tggaagaggc ttctagaagg gaagaaattg tccctctgag gccgccgtgg | 1620 |
| gtgacctgca gagacttcct gcctggaact catctgtgaa ctgggacaga agcagaggag | 1680 |
| gctgcctgct gtgataccc cttacctccc ccagtgcctt cttcagaata tctgcactgt | 1740 |
| cttctgatcc tgttagtcac tgtggttcat caaataaaac tgtttgtgca actgttgtgt | 1800 |

<210> SEQ ID NO 59
<211> LENGTH: 1666
<212> TYPE: DNA
<213> ORGANISM: Homo sapiens

<400> SEQUENCE: 59

```
aactgcagcc agggagactc agactagaat ggaggtagaa agaactgatg cagagtgggt      60
ttaattctaa gccttttttgt ggctaagttt tgttgttgtt aacttattga atttagagtt    120
gtattgcact ggtcatgtga agccagagc agcaccagtg tcaaaatagt gacagagagt     180
tttgaatacc atagttagta tatatgtact cagagtattt ttattaaaga aggcaaagag    240
cccggcatag atcttatctt catcttcact cggttgcaaa atcaatagtt aagaaatagc    300
atctaaggga acttttaggt gggaaaaaaa atctagagat ggctctaaat gactgtttcc    360
ttctgaactt ggaggtggac catttcatgc actgcaacat ctccagtcac agtgcggatc    420
tccccgtgaa cgatgactgg tcccacccgg ggatcctcta tgtcatccct gcagtttatg    480
gggttatcat tctgataggc ctcattggca acatcacttt gatcaagatc ttctgtacag    540
tcaagtccat gcgaaacgtt ccaaacctgt tcatttccag tctggctttg ggagacctgc    600
tcctcctaat aacgtgtgct ccagtggatg ccagcaggta cctggctgac agatggctat    660
ttggcaggat tggctgcaaa ctgatcccct ttatacagct tacctctgtt ggggtgtctg    720
tcttcacact cacggcgctc tcggcagaca gatacaaagc cattgtccgg ccaatggata    780
tccaggcctc ccatgccctg atgaagatct gcctcaaagc cgcctttatc tggatcatct    840
ccatgctgct ggccattcca gaggccgtgt tttctgacct ccatcccttc catgaggaaa    900
gcaccaacca gaccttcatt agctgtgccc catacccaca ctctaatgag cttcaccccca    960
aaatccattc tatggcttcc tttctggtct tctacgtcat cccactgtcg atcatctctg   1020
tttactacta cttcattgct aaaaatctga tccagagtgc ttacaatctt cccgtggaag   1080
ggaatataca tgtcaagaag cagattgaat cccggaagcg acttgccaag acagtgctgg   1140
tgtttgtggg cctgttcgcc ttctgctggc tccccaatca tgtcatctac ctgtaccgct   1200
cctaccacta ctctgaggtg acacctcca tgctccactt tgtcaccagc atctgtgccc   1260
gcctcctggc cttcaccaac tcctgcgtga accccttttgc cctctacctg ctgagcaaga   1320
gtttcaggaa acagttcaac actcagctgc tctgttgcca gctggcctg atcatccggt   1380
ctcacagcac tggaaggagt acaacctgca tgacctccct caagagtacc aaccccctccg   1440
tggccaccttt tagcctcatc aatggaaaca tctgtcacga gcggtatgtc tagattgacc   1500
cttgattttg ccccctgagg gacggttttg cttttatggct agacaggaac ccttgcatcc   1560
attgttgtgt ctgtgccctc caaagagcct tcagaatgct cctgagtggt gtaggtgggg   1620
gtggggaggc ccaaatgatg gatcaccatt atatttttgaa agaagc                  1666
```

<210> SEQ ID NO 60
<211> LENGTH: 2876
<212> TYPE: DNA
<213> ORGANISM: Homo sapiens

<400> SEQUENCE: 60

```
tgaaacctaa cccgccctgg ggaggcgcgc agcagaggct ccgattcggg gcaggtgaga     60
ggctgacttt ctctcggtgc gtccagtgga gctctgagtt tcgaatcggc ggcggcggat    120
```

-continued

```
tccccgcgcg cccggcgtcg gggcttccag gaggatgcgg agccccagcg cggcgtggct    180
gctgggggcc gccatcctgc tagcagcctc tctctcctgc agtggcacca tccaaggaac    240
caatagatcc tctaaaggaa gaagccttat tggtaaggtt gatggcacat cccacgtcac    300
tggaaaagga gttacagttg aaacagtctt ttctgtggat gagttttctg catctgtcct    360
cactggaaaa ctgaccactg tcttccttcc aattgtctac acaattgtgt ttgtggtggg    420
tttgccaagt aacggcatgg ccctgtgggt cttttctttc cgaactaaga agaagcaccc    480
tgctgtgatt tacatggcca atctggcctt ggctgacctc ctctctgtca tctggttccc    540
cttgaagatt gccatcaca tacatggcaa caactggatt tatggggaag ctctttgtaa    600
tgtgcttatt ggcttttttct atggcaacat gtactgttcc attctcttca tgacctgcct    660
cagtgtgcag aggtattggg tcatcgtgaa ccccatgggg cactccagga agaaggcaaa    720
cattgccatt ggcatctccc tggcaatatg gctgctgatt ctgctggtca ccatcccttt    780
gtatgtcgtg aagcagacca tcttcattcc tgccctgaac atcacgacct gtcatgatgt    840
tttgcctgag cagctcttgg tgggagacat gttcaattac ttcctctctc tggccattgg    900
ggtctttctg ttcccagcct tcctcacagc ctctgcctat gtgctgatga tcagaatgct    960
gcgatcttct gccatggatg aaaactcaga gaagaaagg aagagggcca tcaaactcat   1020
tgtcactgtc ctggccatgt acctgatctg cttcactcct agtaaccttc tgcttgtggt   1080
gcattatttt ctgattaaga gccagggcca gagccatgtc tatgccctgt acattgtagc   1140
cctctgcctc tctacccta acagctgcat cgaccccttt gtctattact ttgtttcaca   1200
tgatttcagg gatcatgcaa agaacgctct cctttgccga agtgtccgca ctgtaaagca   1260
gatgcaagta tccctcacct caagaaaaca ctccaggaaa tccagctctt actcttcaag   1320
ttcaaccact gttaagacct cctattgagt tttccaggtc ctcagatggg aattgcacag   1380
taggatgtgg aacctgtttta atgttatgag gacgtgtctg ttatttccta atcaaaaagg   1440
tctcaccaca taccatgtgg atgcagcacc tctcaggatt gctaggagct cccctgtttg   1500
catgagaaaa gtagtccccc aaattaacat cagtgtctgt ttcagaatct ctctactcag   1560 atgacccag aaactgaacc aacagaagca gacttttcag aagatggtga agacagaaac   1620
ccagtaactt gcaaaaagta gacttggtgt gaagactcac ttctcagctg aaattatata   1680
tatacacata tatatatttt acatctggga tcatgataga cttgttaggg cttcaaggcc   1740
ctcagagatg atcagtccaa ctgaacgacc ttacaaatga ggaaaccaag ataaatgagc   1800
tgccagaatc aggtttccaa tcaacagcag tgagttggga ttggacagta gaatttcaat   1860
gtccagtgag tgaggttctt gtaccacttc atcaaaatca tggatcttgg ctgggtgcgg   1920
tgcctcatgc ctgtaatcct agcactttgg gaggctgagg caggcaatca cttgaggtca   1980
ggagttcgag accagcctgg ccatcatggc gaaacctcat ctctactaaa aatacaaaag   2040
ttaaccaggt gtgtggtgca cgtttgtaat cccagttact caggaggctg aggcacaaga   2100
attgagtatc actttaactc aggaggcaga ggttgcagtg agccgagatt gcaccactgc   2160
actccagctt gggtgataaa ataaataaa atagtcgtga atcttgttca aaatgcagat   2220
tcctcagatt caataatgag agctcagact gggaacaggg cccaggaatc tgtgtggtac   2280
aaacctgcat ggtgtttatg cacacagaga tttgagaacc attgttctga atgctgcttc   2340
catttgacaa agtgccgtga taattttga aaagagaagc aaacaatggt gtctctttta   2400
tgttcagctt ataatgaaat ctgtttgttg acttattagg actttgaatt atttctttat   2460
taaccctctg agttttttgta tgtattatta ttaaagaaaa atgcaatcag gattttaaac   2520
```

-continued

```
atgtaaatac aaattttgta taacttttga tgacttcagt gaaattttca ggtagtctga    2580
gtaatagatt gttttgccac ttagaatagc atttgccact tagtatttta aaaataatt     2640 gttggagtat ttattgtcag ttttgttcac ttgttatcta atacaaaatt ataaagcctt    2700
cagagggttt ggaccacatc tctttggaaa atagtttgca acatatttaa gagatacttg    2760
atgccaaaat gactttatac aacgattgta tttgtgactt ttaaaaataa ttattttatt    2820
gtgtaattga tttataaata acaaaatttt ttttacaact taaaaaaaaa aaaaaa         2876
```

<210> SEQ ID NO 61
<211> LENGTH: 1668
<212> TYPE: DNA
<213> ORGANISM: Homo sapiens

<400> SEQUENCE: 61

```
gggagataac tcgtgctcac aggaagccac gcacccttga aaggcaccgg gtccttctta      60
gcatcgtgct tcctgagcaa gcctggcatt gcctcacaga ccttcctcag agccgctttc    120
agaaaagcaa gctgcttctg gttgggccca gacctgcctt gaggagcctg tagagttaaa    180
aaatgaaccc cacggatata gcagacacca ccctcgatga aagcatatac agcaattact    240
atctgtatga agtatccccc aagccttgca ccaaagaagg catcaaggca tttggggagc    300
tcttcctgcc cccactgtat tccttggttt ttgtatttgg tctgcttgga aattctgtgg    360
tggttctggt cctgttcaaa tacaagcggc tcaggtccat gactgatgtg tacctgctca    420
accttgccat ctcggatctg ctcttcgtgt tttccctccc tttttggggc tactatgcag    480
cagaccagtg ggttttttgg ctaggtctgt gcaagatgat ttcctggatg tacttggtgg    540
gcttttacag tggcatattc tttgtcatgc tcatgagcat tgatagatac ctggcaattg    600
tgcacgcggt gttttccttg agggcaagga ccttgactta tgggggtcatc accagtttgg    660 ctacatggtc agtggctgtg ttcgcctccc ttcctggctt tctgttcagc acttgttata    720
ctgagcgcaa ccatacctac tgcaaaacca gtactctct caactccacg acgtggaagg    780
ttctcagctc cctggaaatc aacattctcg gattggtgat ccccttaggg atcatgctgt    840
tttgctactc catgatcatc aggaccttgc agcattgtaa aaatgagaag aagaacaagg    900
cggtgaagat gatcttgcc gtggtggtcc tcttccttgg gttctggaca ccttacaaca    960
tagtgctctt cctagagacc ctggtggagc tagaagtcct tcaggactgc accttgaaa    1020 gatacttgga ctatgccatc caggccacag aaactctggc ttttgttcac tgctgcctta    1080
atcccatcat ctactttttt ctgggggaga aatttcgcaa gtacatccta cagctcttca    1140
aaacctgcag gggcctttttt gtgctctgcc aatactgtgg gctcctccaa atttactctg    1200
ctgacacccc cagctcatct tacacgcagt ccaccatgga tcatgatctt catgatgctc    1260
tgtagaaaaa tgaaatggtg aaatgcagag tcaatgaact ttccacattc agagcttact    1320
taaaattgta ttttggtaag agatccctga gccagtgtca ggaggaaggc ttacacccac    1380
agtggaaaga cagcttctca tcctgcaggc agcttttttct ctcccactag acaagtccag    1440
cctggcaagg gttcacctgg gctgaggcat ccttcctcac accaggcttg cctgcaggca    1500
tgagtcagtc tgatgagaac tctgagcagt gcttgaatga agttgtaggt aatattgcaa    1560
ggcaaagact attcccttct aacctgaact gatgggtttc tccagaggga attgcagagt    1620
actggctgat ggagtaaatc gctaccttt gctgtggcaa atgggccc                  1668
```

<210> SEQ ID NO 62

<211> LENGTH: 1679
<212> TYPE: DNA
<213> ORGANISM: Homo sapiens

<400> SEQUENCE: 62

| | |
|---|---|
| gtttgttggc tgcggcagca ggtagcaaag tgacgccgag ggcctgagtg ctccagtagc | 60 |
| caccgcatct ggagaaccag cggttaccat ggagggatc agtatataca cttcagataa | 120 |
| ctacaccgag gaaatgggct caggggacta tgactccatg aaggaaccct gtttccgtga | 180 |
| agaaaatgct aatttcaata aaatcttcct gcccaccatc tactccatca tcttcttaac | 240 |
| tggcattgtg ggcaatggat tggtcatcct ggtcatgggt taccagaaga aactgagaag | 300 |
| catgacggac aagtacaggc tgcacctgtc agtggccgac ctcctctttg tcatcacgct | 360 |
| tcccttctgg gcagttgatg ccgtggcaaa ctggtacttt gggaacttcc tatgcaaggc | 420 |
| agtccatgtc atctacacag tcaacctcta cagcagtgtc ctcatcctgg ccttcatcag | 480 |
| tctggaccgc tacctggcca tcgtccacgc caccaacagt cagaggccaa ggaagctgtt | 540 |
| ggctgaaaag gtggtctatg ttggcgtctg gatccctgcc ctcctgctga ctattcccga | 600 |
| cttcatcttt gccaacgtca gtgaggcaga tgacagatat atctgtgacc gcttctaccc | 660 |
| caatgacttg tgggtggttg tgttccagtt tcagcacatc atggttggcc ttatcctgcc | 720 |
| tggtattgtc atcctgtcct gctattgcat tatcatctcc aagctgtcac actccaaggg | 780 |
| ccaccagaag cgcaaggccc tcaagaccac agtcatcctc atcctggctt tcttcgcctg | 840 |
| ttggctgcct tactacattg ggatcagcat cgactcctcc atcctcctgg aaatcatcaa | 900 |
| gcaagggtgt gagtttgaga cactgtgca caagtggatt tccatcaccg aggccctagc | 960 |
| tttcttccac tgttgtctga cccccatcct ctatgctttc cttggagcca aatttaaaac | 1020 |
| ctctgcccag cacgcactca cctctgtgag cagagggtcc agcctcaaga tcctctccaa | 1080 |
| aggaaagcga ggtggacatt catctgtttc cactgagtct gagtcttcaa gttttcactc | 1140 |
| cagctaacac agatgtaaaa gactttttttt tatacgataa ataacttttt tttaagttac | 1200 |
| acattttttca gatataaaag actgaccaat attgtacagt ttttattgct tgttggattt | 1260 |
| ttgtcttgtg tttctttagt ttttgtgaag tttaattgac ttatttatat aaattttttt | 1320 |
| tgtttcatat tgatgtgtgt ctaggcagga cctgtggcca agttcttagt tgctgtatgt | 1380 |
| ctcgtggtag gactgtagaa aagggaactg aacattccag agcgtgtagt gaatcacgta | 1440 |
| aagctagaaa tgatccccag ctgtttatgc atagataatc tctccattcc cgtggaacgt | 1500 |
| ttttcctgtt cttaagacgt gattttgctg tagaagatgg cacttataac caaagcccaa | 1560 |
| agtggtatag aaatgctggt ttttcagttt tcaggagtgg gttgatttca gcacctacag | 1620 |
| tgtacagtct tgtattaagt tgttaataaa agtacatgtt aaacttactt agtgttatg | 1679 |

<210> SEQ ID NO 63
<211> LENGTH: 2859
<212> TYPE: DNA
<213> ORGANISM: Homo sapiens

<400> SEQUENCE: 63

| | |
|---|---|
| cattcagaga cagaaggtgg atagacaaat ctccaccttc agactggtag gctcctccag | 60 |
| aagccatcag acaggaagat gtgaaaatcc ccagcactca tcccagaatc actaagtggc | 120 |
| acctgtcctg ggccaaagtc ccaggacaga cctcattgtt cctctgtggg aatacctccc | 180 |
| caggagggca tcctggattt ccccccttgca acccaggtca gaagtttcat cgtcaaggtt | 240 |
| gtttcatctt ttttttcctg tctaacagct ctgactacca cccaaccttg aggcacagtg | 300 |

```
aagacatcgg tggccactcc aataacagca ggtcacagct gctcttctgg aggtgtccta    360
caggtgaaaa gcccagcgac ccagtcagga tttaagttta cctcaaaaat ggaagatttt    420
aacatggaga gtgacagctt tgaagatttc tggaaaggtg aagatcttag taattacagt    480
tacagctcta ccctgccccc ttttctacta gatgccgccc catgtgaacc agaatccctg    540
gaaatcaaca agtattttgt ggtcattatc tatgccctgg tattcctgct gagcctgctg    600
ggaaactccc tcgtgatgct ggtcatctta tacagcaggg tcggccgctc cgtcactgat    660
gtctacctgc tgaacctagc cttggccgac ctactctttg ccctgacctt gcccatctgg    720
gccgcctcca aggtgaatgg ctggattttt ggcacattcc tgtgcaaggt ggtctcactc    780
ctgaaggaag tcaacttcta tagtggcatc ctgctactgg cctgcatcag tgtggaccgt    840
tacctggcca ttgtccatgc cacacgcaca ctgacccaga agcgctactt ggtcaaattc    900
atatgtctca gcatctgggg tctgtccttg ctcctggccc tgcctgtctt acttttccga    960
aggaccgtct actcatccaa tgttagccca gcctgctatg aggacatggg caacaataca   1020
gcaaactggc ggatgctgtt acggatcctg ccccagtcct ttggcttcat cgtgccactg   1080
ctgatcatgc tgttctgcta cggattcacc ctgcgtacgc tgtttaaggc ccacatgggg   1140
cagaagcacc gggccatgcg ggtcatcttt gctgtcgtcc tcatcttcct gctctgctgg   1200 ctgcccctaca acctggtcct gctggcagac accctcatga ggacccaggt gatccaggag   1260
acctgtgagc gccgcaatca catcgaccgg gctctggatg ccaccgagat tctgggcatc   1320
cttcacagct gcctcaaccc cctcatctac gccttcattg ccagaagtt tcgccatgga   1380 ctcctcaaga ttctagctat acatggcttg atcagcaagg actccctgcc caaagacagc   1440
aggccttcct ttgttggctc ttcttcaggg cacacttcca ctactctcta agacctcctg   1500
cctaagtgca gccccgtggg gttcctcccc tctcttcaca gtcacattcc aagcctcatg   1560
tccactggtt cttcttggtc tcagtgtcaa tgcagccccc attgtggtca caggaagtag   1620
aggaggccac gttcttacta gtttcccttg catggtttag aaagcttgcc ctggtgcctc   1680
accccttgcc ataattacta tgtcatttgc tggagctctg cccatcctgc ccctgagccc   1740
atggcactct atgttctaag aagtgaaaat ctacactcca gtgagacagc tctgcatact   1800
cattaggatg gctagtatca aaagaaagaa atcaggctg gccaacgggg tgaaaccctg    1860
tctctactaa aaatacaaaa aaaaaaaaaa attagccggg cgtggtggtg agtgcctgta   1920
atcacagcta cttgggaggc tgagatggga gaatcacttg aacccgggag gcagaggttg   1980
cagtgagccg agattgtgcc cctgcactcc agcctgagcg acagtgagac tctgtctcag   2040
tccatgaaga tgtagaggag aaactggaac tctcgagcgt tgctgggggg gattgtaaaa   2100
tggtgtgacc actgcagaag acagtatggc agctttcctc aaaacttcag acatagaatt   2160
aacacatgat cctgcaattc cacttatagg aattgaccca caagaaatga agcagggac    2220 ttgaaccat atttgtacac caatattcat agcagcttat tcacaagacc caaaaggcag    2280
aagcaaccca aatgttcatc aatgaatgaa tgaatggcta agcaaaatgt gatatgtacc    2340
taacgaagta tccttcagcc tgaaagagga atgaagtact catacatgtt acaacacgga   2400
cgaaccttga aactttatg ctaagtgaaa taagccagac atcaacagat aaatagttta    2460
tgattccacc tacatgaggt actgagagtg aacaaattta cagagacaga aagcagaaca   2520
gtgattacca gggactgagg ggaggggagc atgggaagtg acggtttaat gggcacaggg   2580
tttatgttta ggatgttgaa aaagttctgc agataaacag tagtgatagt tgtaccgcaa   2640
```

```
tgtgacttaa tgccactaaa ttgacactta aaaatggttt aaatggtcaa ttttgttatg   2700
tatattttat atcaatttaa aaaaaaacct gagccccaaa aggtatttta atcaccaagg   2760
ctgattaaac caaggctaga accacctgcc tatatttttt gttaaatgat ttcattcaat   2820 atctttttt taataaacca tttttacttg ggtgtttat                           2859
```

<210> SEQ ID NO 64
<211> LENGTH: 27
<212> TYPE: DNA
<213> ORGANISM: Homo Sapiens

<400> SEQUENCE: 64

```
tgtgcgcgcg gccagagcag gtgcgca                                       27
```

<210> SEQ ID NO 65
<211> LENGTH: 26
<212> TYPE: DNA
<213> ORGANISM: Homo Sapiens

<400> SEQUENCE: 65

```
gaggatccgt caaccacaag ggtctc                                        26
```

<210> SEQ ID NO 66
<211> LENGTH: 27
<212> TYPE: DNA
<213> ORGANISM: Homo Sapiens

<400> SEQUENCE: 66

```
tgtgcgcgcg gcctgatcat ccggtct                                       27
```

<210> SEQ ID NO 67
<211> LENGTH: 26
<212> TYPE: DNA
<213> ORGANISM: Homo Sapiens

<400> SEQUENCE: 67

```
gaggatccga cataccgctc gtgaca                                        26
```

<210> SEQ ID NO 68
<211> LENGTH: 28
<212> TYPE: DNA
<213> ORGANISM: Homo Sapiens

<400> SEQUENCE: 68

```
tgtgcgcgca gtgtccgcac tgtaaagc                                      28
```

<210> SEQ ID NO 69
<211> LENGTH: 26
<212> TYPE: DNA
<213> ORGANISM: Homo Sapiens

<400> SEQUENCE: 69

```
gaggatccat aggaggtctt aacagt                                        26
```

<210> SEQ ID NO 70
<211> LENGTH: 27
<212> TYPE: DNA
<213> ORGANISM: Homo Sapiens

<400> SEQUENCE: 70

```
tgtgcgcgcg gccttttgt gctctgc                                        27
```

<210> SEQ ID NO 71
<211> LENGTH: 26
<212> TYPE: DNA
<213> ORGANISM: Homo Sapiens

<400> SEQUENCE: 71
gaggatccca gagcatcatg aagatc                                        26

<210> SEQ ID NO 72
<211> LENGTH: 28
<212> TYPE: DNA
<213> ORGANISM: Homo Sapiens

<400> SEQUENCE: 72
tgtgcgcgcg gcttgatcag caagggac                                      28

<210> SEQ ID NO 73
<211> LENGTH: 26
<212> TYPE: DNA
<213> ORGANISM: Homo Sapiens

<400> SEQUENCE: 73
gaggatccga gagtagtgga agtgtg                                        26

<210> SEQ ID NO 74
<211> LENGTH: 27
<212> TYPE: DNA
<213> ORGANISM: Homo Sapiens

<400> SEQUENCE: 74
tgtgcgcgcg ggtccagcct caagatc                                       27

<210> SEQ ID NO 75
<211> LENGTH: 26
<212> TYPE: DNA
<213> ORGANISM: Homo Sapiens

<400> SEQUENCE: 75
gaggatccgc tggagtgaaa acttga                                        26

<210> SEQ ID NO 76
<211> LENGTH: 5616
<212> TYPE: DNA
<213> ORGANISM: Homo Sapiens

<400> SEQUENCE: 76
ccccggcgca gcgcggccgc agcagcctcc gcccccgca cggtgtgagc gcccgacgcg     60
gccgaggcgg ccggagtccc gagctagccc cggcggccgc cgccgcccag accgacgac    120 aggccacctc gtcggcgtcc gcccgagtcc ccgcctcgcc gccaacgcca caaccaccgc   180
gcacggcccc ctgactccgt ccagtattga tcgggagagc cggagcgagc tcttcgggga   240
gcagcgatgc gaccctccgg gacggccggg gcagcgctcc tggcgctgct ggctgcgctc   300
tgcccggcga gtcgggctct ggaggaaaag aaagtttgcc aaggcacgag taacaagctc   360
acgcagttgg gcacttttga agatcatttt ctcagcctcc agaggatgtt caataactgt   420
gaggtggtcc ttgggaattt ggaaattacc tatgtgcaga ggaattatga tctttccttc   480
ttaaagacca tccaggaggt ggctggttat gtcctcattg ccctcaacac agtggagcga   540
attcctttgg aaaacctgca gatcatcaga ggaaatatgt actacgaaaa ttcctatgcc   600
ttagcagtct tatctaacta tgatgcaaat aaaaccggac tgaaggagct gcccatgaga   660

```
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc aatgggagc     840 tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gccccgggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga aatttcagg aaacaaaaat ttgtgctatg caaatacaat aaactggaaa   1680
aaactgtttg gacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcaggaatg cgtggacaag   1860 tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg   2160 aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caagtgctg    2400 ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcc aaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
```

```
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga aagaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt ccctttgagc agaaatttat    4140
ctttcaaaga ggtatatttg aaaaaaaaaa aaagtatatg tgaggatttt tattgattgg    4200
ggatcttgga gtttttcatt gtcgctattg attttttactt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca ataataact cggattccag cccacattgg attcatcagc    4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920 acccccaaa attagtttgt gttacttatg gaagatagtt ttctccttt acttcacttc    4980 aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccacctttt tttcctaatc tgtgtgtgcc ctgtaacctg    5340
actggttaac agcagtcctt tgtaaacagt gtttaaact ctcctagtca atatccaccc    5400
```
catccaattt atcaaggaag aaatggttca gaaatatttt tcagcctaca gttatgttca     5460
gtcacacaca catacaaaat gttccttttg cttttaaagt aattttttgac tcccagatca    5520 gtcagagccc ctacagcatt gttaagaaag tatttgattt ttgtctcaat gaaaataaaa     5580
ctatattcat ttccactcta aaaaaaaaaa aaaaaa                               5616

<210> SEQ ID NO 77
<211> LENGTH: 12
<212> TYPE: PRT
<213> ORGANISM: Homo Sapiens

<400> SEQUENCE: 77

Gly Gly Ser Gly Ser Glu Asn Leu Tyr Phe Gln Leu
              5                  10

<210> SEQ ID NO 78
<211> LENGTH: 1291
<212> TYPE: PRT
<213> ORGANISM: Homo sapiens

<400> SEQUENCE: 78

Met Ala Gly Ala Ala Ser Pro Cys Ala Asn Gly Cys Gly Pro Gly Ala
                 5                  10                  15

Pro Ser Asp Ala Glu Val Leu His Leu Cys Arg Ser Leu Glu Val Gly
             20                  25                  30

Thr Val Met Thr Leu Phe Tyr Ser Lys Lys Ser Gln Arg Pro Glu Arg
         35                  40                  45

Lys Thr Phe Gln Val Lys Leu Glu Thr Arg Gln Ile Thr Trp Ser Arg
     50                  55                  60

Gly Ala Asp Lys Ile Glu Gly Ala Ile Asp Ile Arg Glu Ile Lys Glu
65                  70                  75                  80

Ile Arg Pro Gly Lys Thr Ser Arg Asp Phe Asp Arg Tyr Gln Glu Asp
                 85                  90                  95

Pro Ala Phe Arg Pro Asp Gln Ser His Cys Phe Val Ile Leu Tyr Gly
            100                 105                 110

Met Glu Phe Arg Leu Lys Thr Leu Ser Leu Gln Ala Thr Ser Glu Asp
        115                 120                 125

Glu Val Asn Met Trp Ile Lys Gly Leu Thr Trp Leu Met Glu Asp Thr
    130                 135                 140

Leu Gln Ala Pro Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Leu Glu Gln Arg Ser Gly Asp Ile
        195                 200                 205

Thr Tyr Gly Gln Phe Ala Gln Leu Tyr Arg Ser Leu Met Tyr Ser Ala
    210                 215                 220

Gln Lys Thr Met Asp Leu Pro Phe Leu Glu Ala Ser Thr Leu Arg Ala
225                 230                 235                 240

Gly Glu Arg Pro Glu Leu Cys Arg Val Ser Leu Pro Glu Phe Gln Gln
                245                 250                 255

Phe Leu Leu Asp Tyr Gln Gly Glu Leu Trp Ala Val Asp Arg Leu Gln
            260                 265                 270

Val Gln Glu Phe Met Leu Ser Phe Leu Arg Asp Pro Leu Arg Glu Ile

-continued

```
                275                 280                 285
Glu Glu Pro Tyr Phe Phe Leu Asp Glu Phe Val Thr Phe Leu Phe Ser
            290                 295                 300
Lys Glu Asn Ser Val Trp Asn Ser Gln Leu Asp Ala Val Cys Pro Asp
305                 310                 315                 320
Thr Met Asn Asn Pro Leu Ser His Tyr Trp Ile Ser Ser His Asn
                325                 330                 335
Thr Tyr Leu Thr Gly Asp Gln Phe Ser Ser Glu Ser Ser Leu Glu Ala
                340                 345                 350
Tyr Ala Arg Cys Leu Arg Met Gly Cys Arg Cys Ile Glu Leu Asp Cys
                355                 360                 365
Trp Asp Gly Pro Asp Gly Met Pro Val Ile Tyr His Gly His Thr Leu
370                 375                 380
Thr Thr Lys Ile Lys Phe Ser Asp Val Leu His Thr Ile Lys Glu His
385                 390                 395                 400
Ala Phe Val Ala Ser Glu Tyr Pro Val Ile Leu Ser Ile Glu Asp His
                405                 410                 415
Cys Ser Ile Ala Gln Gln Arg Asn Met Ala Gln Tyr Phe Lys Lys Val
                420                 425                 430
Leu Gly Asp Thr Leu Leu Thr Lys Pro Val Glu Ile Ser Ala Asp Gly
                435                 440                 445
Leu Pro Ser Pro Asn Gln Leu Lys Arg Lys Ile Leu Ile Lys His Lys
                450                 455                 460
Lys Leu Ala Glu Gly Ser Ala Tyr Glu Glu Val Pro Thr Ser Met Met
465                 470                 475                 480
Tyr Ser Glu Asn Asp Ile Ser Asn Ser Ile Lys Asn Gly Ile Leu Tyr
                485                 490                 495
Leu Glu Asp Pro Val Asn His Glu Trp Tyr Pro His Tyr Phe Val Leu
                500                 505                 510
Thr Ser Ser Lys Ile Tyr Tyr Ser Glu Glu Thr Ser Ser Asp Gln Gly
                515                 520                 525
Asn Glu Asp Glu Glu Glu Pro Lys Glu Val Ser Ser Ser Thr Glu Leu
530                 535                 540
His Ser Asn Glu Lys Trp Phe His Gly Lys Leu Gly Ala Gly Arg Asp
545                 550                 555                 560
Gly Arg His Ile Ala Glu Arg Leu Leu Thr Glu Tyr Cys Ile Glu Thr
                565                 570                 575
Gly Ala Pro Asp Gly Ser Phe Leu Val Arg Glu Ser Glu Thr Phe Val
                580                 585                 590
Gly Asp Tyr Thr Leu Ser Phe Trp Arg Asn Gly Lys Val Gln His Cys
                595                 600                 605
Arg Ile His Ser Arg Gln Asp Ala Gly Thr Pro Lys Phe Phe Leu Thr
610                 615                 620
Asp Asn Leu Val Phe Asp Ser Leu Tyr Asp Leu Ile Thr His Tyr Gln
625                 630                 635                 640
Gln Val Pro Leu Arg Cys Asn Glu Phe Glu Met Arg Leu Ser Glu Pro
                645                 650                 655
Val Pro Gln Thr Asn Ala His Glu Ser Lys Glu Trp Tyr His Ala Ser
                660                 665                 670
Leu Thr Arg Ala Gln Ala Glu His Met Leu Met Arg Val Pro Arg Asp
                675                 680                 685
Gly Ala Phe Leu Val Arg Lys Arg Asn Glu Pro Asn Ser Tyr Ala Ile
            690                 695                 700
```

```
Ser Phe Arg Ala Glu Gly Lys Ile Lys His Cys Arg Val Gln Gln Glu
705                 710                 715                 720

Gly Gln Thr Val Met Leu Gly Asn Ser Glu Phe Asp Ser Leu Val Asp
                725                 730                 735

Leu Ile Ser Tyr Tyr Glu Lys His Pro Leu Tyr Arg Lys Met Lys Leu
                740                 745                 750

Arg Tyr Pro Ile Asn Glu Glu Ala Leu Glu Lys Ile Gly Thr Ala Glu
                755                 760                 765

Pro Asp Tyr Gly Ala Leu Tyr Glu Gly Arg Asn Pro Gly Phe Tyr Val
        770                 775                 780

Glu Ala Asn Pro Met Pro Thr Phe Lys Cys Ala Val Lys Ala Leu Phe
785                 790                 795                 800

Asp Tyr Lys Ala Gln Arg Glu Asp Glu Leu Thr Phe Ile Lys Ser Ala
                805                 810                 815

Ile Ile Gln Asn Val Glu Lys Gln Glu Gly Gly Trp Trp Arg Gly Asp
                820                 825                 830

Tyr Gly Gly Lys Lys Gln Leu Trp Phe Pro Ser Asn Tyr Val Glu Glu
                835                 840                 845

Met Val Asn Pro Val Ala Leu Glu Pro Glu Arg Glu His Leu Asp Glu
850                 855                 860

Asn Ser Pro Leu Gly Asp Leu Leu Arg Gly Val Leu Asp Val Pro Ala
865                 870                 875                 880

Cys Gln Ile Ala Ile Arg Pro Glu Gly Lys Asn Asn Arg Leu Phe Val
                885                 890                 895

Phe Ser Ile Ser Met Ala Ser Val Ala His Trp Ser Leu Asp Val Ala
                900                 905                 910

Ala Asp Ser Gln Glu Glu Leu Gln Asp Trp Val Lys Lys Ile Arg Glu
                915                 920                 925

Val Ala Gln Thr Ala Asp Ala Arg Leu Thr Glu Gly Lys Ile Met Glu
930                 935                 940

Arg Arg Lys Lys Ile Ala Leu Glu Leu Ser Glu Leu Val Val Tyr Cys
945                 950                 955                 960

Arg Pro Val Pro Phe Asp Glu Glu Lys Ile Gly Thr Glu Arg Ala Cys
                965                 970                 975

Tyr Arg Asp Met Ser Ser Phe Pro Glu Thr Lys Ala Glu Lys Tyr Val
                980                 985                 990

Asn Lys Ala Lys Gly Lys Lys Phe Leu Gln Tyr Asn Arg Leu Gln Leu
                995                 1000                1005

Ser Arg Ile Tyr Pro Lys Gly Gln Arg Leu Asp Ser Ser Asn Tyr Asp
        1010                1015                1020

Pro Leu Pro Met Trp Ile Cys Gly Ser Gln Leu Val Ala Leu Asn Phe
1025                1030                1035                1040

Gln Thr Pro Asp Lys Pro Met Gln Met Asn Gln Ala Leu Phe Met Thr
                1045                1050                1055

Gly Arg His Cys Gly Tyr Val Leu Gln Pro Ser Thr Met Arg Asp Glu
                1060                1065                1070

Ala Phe Asp Pro Phe Asp Lys Ser Ser Leu Arg Gly Leu Glu Pro Cys
                1075                1080                1085

Ala Ile Ser Ile Glu Val Leu Gly Ala Arg His Leu Pro Lys Asn Gly
                1090                1095                1100

Arg Gly Ile Val Cys Pro Phe Val Glu Ile Glu Val Ala Gly Ala Glu
1105                1110                1115                1120
```

```
Tyr Asp Ser Thr Lys Gln Lys Thr Glu Phe Val Val Asp Asn Gly Leu
                1125                1130                1135

Asn Pro Val Trp Pro Ala Lys Pro Phe His Phe Gln Ile Ser Asn Pro
            1140                1145                1150

Glu Phe Ala Phe Leu Arg Phe Val Val Tyr Glu Glu Asp Met Phe Ser
        1155                1160                1165

Asp Gln Asn Phe Leu Ala Gln Ala Thr Phe Pro Val Lys Gly Leu Lys
    1170                1175                1180

Thr Gly Tyr Arg Ala Val Pro Leu Lys Asn Asn Tyr Ser Glu Asp Leu
1185                1190                1195                1200

Glu Leu Ala Ser Leu Leu Ile Lys Ile Asp Ile Phe Pro Ala Lys Gln
                1205                1210                1215

Glu Asn Gly Asp Leu Ser Pro Phe Ser Gly Thr Ser Leu Arg Glu Arg
            1220                1225                1230

Gly Ser Asp Ala Ser Gly Gln Leu Phe His Gly Arg Ala Arg Glu Gly
        1235                1240                1245

Ser Phe Glu Ser Arg Tyr Gln Gln Pro Phe Glu Asp Phe Arg Ile Ser
    1250                1255                1260

Gln Glu His Leu Ala Asp His Phe Asp Ser Arg Glu Arg Arg Ala Pro
1265                1270                1275                1280

Arg Arg Thr Arg Val Asn Gly Asp Asn Arg Leu
                1285                1290

<210> SEQ ID NO 79
<211> LENGTH: 3054
<212> TYPE: PRT
<213> ORGANISM: Homo sapiens

<400> SEQUENCE: 79

Met Ala Leu Ile Phe Gly Thr Val Asn Ala Asn Ile Leu Lys Glu Val
                5                  10                  15

Phe Gly Gly Ala Arg Met Ala Cys Val Thr Ser Ala His Met Ala Gly
            20                  25                  30

Ala Asn Gly Ser Ile Leu Lys Lys Ala Glu Glu Thr Ser Arg Ala Ile
        35                  40                  45

Met His Lys Pro Val Ile Phe Gly Glu Asp Tyr Ile Thr Glu Ala Asp
    50                  55                  60

Leu Pro Tyr Thr Pro Leu His Leu Glu Val Asp Ala Glu Met Glu Arg
65                  70                  75                  80

Met Tyr Tyr Leu Gly Arg Arg Ala Leu Thr His Gly Lys Arg Arg Lys
                85                  90                  95

Val Ser Val Asn Asn Lys Arg Asn Arg Arg Lys Val Ala Lys Thr
            100                 105                 110

Tyr Val Gly Arg Asp Ser Ile Val Glu Lys Ile Val Pro His Thr
        115                 120                 125

Glu Arg Lys Val Asp Thr Thr Ala Ala Val Glu Asp Ile Cys Asn Glu
    130                 135                 140

Ala Thr Thr Gln Leu Val His Asn Ser Met Pro Lys Arg Lys Lys Gln
145                 150                 155                 160

Lys Asn Phe Leu Pro Ala Thr Ser Leu Ser Asn Val Tyr Ala Gln Thr
                165                 170                 175

Trp Ser Ile Val Arg Lys Arg His Met Gln Val Glu Ile Ile Ser Lys
            180                 185                 190

Lys Ser Val Arg Ala Arg Val Lys Arg Phe Glu Gly Ser Val Gln Leu
        195                 200                 205
```

```
Phe Ala Ser Val Arg His Met Tyr Gly Glu Arg Lys Arg Val Asp Leu
210                 215                 220
Arg Ile Asp Asn Trp Gln Gln Glu Thr Leu Leu Asp Leu Ala Lys Arg
225                 230                 235                 240
Phe Lys Asn Glu Arg Val Asp Gln Ser Lys Leu Thr Phe Gly Ser Ser
            245                 250                 255
Gly Leu Val Leu Arg Gln Gly Ser Tyr Gly Pro Ala His Trp Tyr Arg
                260                 265                 270
His Gly Met Phe Ile Val Arg Gly Arg Ser Asp Gly Met Leu Val Asp
            275                 280                 285
Ala Arg Ala Lys Val Thr Phe Ala Val Cys His Ser Met Thr His Tyr
290                 295                 300
Ser Asp Lys Ser Ile Ser Glu Ala Phe Phe Ile Pro Tyr Ser Lys Lys
305                 310                 315                 320
Phe Leu Glu Leu Arg Pro Asp Gly Ile Ser His Glu Cys Thr Arg Gly
            325                 330                 335
Val Ser Val Glu Arg Cys Gly Glu Val Ala Ala Ile Leu Thr Gln Ala
                340                 345                 350
Leu Ser Pro Cys Gly Lys Ile Thr Cys Lys Arg Cys Met Val Glu Thr
            355                 360                 365
Pro Asp Ile Val Glu Gly Glu Ser Gly Glu Ser Val Thr Asn Gln Gly
370                 375                 380
Lys Leu Leu Ala Met Leu Lys Glu Gln Tyr Pro Asp Phe Pro Met Ala
385                 390                 395                 400
Glu Lys Leu Leu Thr Arg Phe Leu Gln Gln Lys Ser Leu Val Asn Thr
            405                 410                 415
Asn Leu Thr Ala Cys Val Ser Val Lys Gln Leu Ile Gly Asp Arg Lys
                420                 425                 430
Gln Ala Pro Phe Thr His Val Leu Ala Val Ser Glu Ile Leu Phe Lys
            435                 440                 445
Gly Asn Lys Leu Thr Gly Ala Asp Leu Glu Glu Ala Ser Thr His Met
450                 455                 460
Leu Glu Ile Ala Arg Phe Leu Asn Asn Arg Thr Glu Asn Met Arg Ile
465                 470                 475                 480
Gly His Leu Gly Ser Phe Arg Asn Lys Ile Ser Ser Lys Ala His Val
            485                 490                 495
Asn Asn Ala Leu Met Cys Asp Asn Gln Leu Asp Gln Asn Gly Asn Phe
                500                 505                 510
Ile Trp Gly Leu Arg Gly Ala His Ala Lys Arg Phe Leu Lys Gly Phe
            515                 520                 525
Phe Thr Glu Ile Asp Pro Asn Glu Gly Tyr Asp Lys Tyr Val Ile Arg
530                 535                 540
Lys His Ile Arg Gly Ser Arg Lys Leu Ala Ile Gly Asn Leu Ile Met
545                 550                 555                 560
Ser Thr Asp Phe Gln Thr Leu Arg Gln Gln Ile Gln Gly Glu Thr Ile
            565                 570                 575
Glu Arg Lys Glu Ile Gly Asn His Cys Ile Ser Met Arg Asn Gly Asn
                580                 585                 590
Tyr Val Tyr Pro Cys Cys Val Thr Leu Glu Asp Gly Lys Ala Gln
            595                 600                 605
Tyr Ser Asp Leu Lys His Pro Thr Lys Arg His Leu Val Ile Gly Asn
610                 615                 620
```

-continued

```
Ser Gly Asp Ser Lys Tyr Leu Asp Leu Pro Val Leu Asn Glu Glu Lys
625                 630                 635                 640

Met Tyr Ile Ala Asn Glu Gly Tyr Cys Tyr Met Asn Ile Phe Phe Ala
                645                 650                 655

Leu Leu Val Asn Val Lys Glu Glu Asp Ala Lys Asp Phe Thr Lys Phe
            660                 665                 670

Ile Arg Asp Thr Ile Val Pro Lys Leu Gly Ala Trp Pro Thr Met Gln
        675                 680                 685

Asp Val Ala Thr Ala Cys Tyr Leu Leu Ser Ile Leu Tyr Pro Asp Val
    690                 695                 700

Leu Arg Ala Glu Leu Pro Arg Ile Leu Val Asp His Asp Asn Lys Thr
705                 710                 715                 720

Met His Val Leu Asp Ser Tyr Gly Ser Arg Thr Thr Gly Tyr His Met
                725                 730                 735

Leu Lys Met Asn Thr Thr Ser Gln Leu Ile Glu Phe Val His Ser Gly
            740                 745                 750

Leu Glu Ser Glu Met Lys Thr Tyr Asn Val Gly Gly Met Asn Arg Asp
        755                 760                 765

Val Val Thr Gln Gly Ala Ile Glu Met Leu Ile Lys Ser Ile Tyr Lys
    770                 775                 780

Pro His Leu Met Lys Gln Leu Leu Glu Glu Pro Tyr Ile Ile Val
785                 790                 795                 800

Leu Ala Ile Val Ser Pro Ser Ile Leu Ile Ala Met Tyr Asn Ser Gly
                805                 810                 815

Thr Phe Glu Gln Ala Leu Gln Met Trp Leu Pro Asn Thr Met Arg Leu
            820                 825                 830

Ala Asn Leu Ala Ala Ile Leu Ser Ala Leu Ala Gln Lys Leu Thr Leu
        835                 840                 845

Ala Asp Leu Phe Val Gln Gln Arg Asn Leu Ile Asn Glu Tyr Ala Gln
    850                 855                 860

Val Ile Leu Asp Asn Leu Ile Asp Gly Val Arg Val Asn His Ser Leu
865                 870                 875                 880

Ser Leu Ala Met Glu Ile Val Thr Ile Lys Leu Ala Thr Gln Glu Met
                885                 890                 895

Asp Met Ala Leu Arg Glu Gly Gly Tyr Ala Val Thr Ser Glu Lys Val
            900                 905                 910

His Glu Met Leu Glu Lys Asn Tyr Val Lys Ala Leu Lys Asp Ala Trp
        915                 920                 925

Asp Glu Leu Thr Trp Leu Glu Lys Phe Ser Ala Ile Arg His Ser Arg
    930                 935                 940

Lys Leu Leu Lys Phe Gly Arg Lys Pro Leu Ile Met Lys Asn Thr Val
945                 950                 955                 960

Asp Cys Gly Gly His Ile Asp Leu Ser Val Lys Ser Leu Phe Lys Phe
                965                 970                 975

His Leu Glu Leu Leu Lys Gly Thr Ile Ser Arg Ala Val Asn Gly Gly
            980                 985                 990

Ala Arg Lys Val Arg Val Ala Lys  Asn Ala Met Thr Lys  Gly Val Phe
        995                 1000                 1005

Leu Lys Ile Tyr Ser Met Leu  Pro Asp Val Tyr Lys  Phe Ile Thr Val
        1010                 1015                 1020

Ser  Ser Val Leu Ser Leu  Leu Leu Thr Phe Leu  Phe Gln Ile Asp Cys
1025                 1030                 1035                 1040

Met Ile Arg Ala His  Arg Glu Ala Lys Val  Ala Ala Gln Leu Gln  Lys
```

-continued

```
                1045                1050                1055
Glu Ser Glu Trp Asp Asn Ile Ile Asn Arg Thr Phe Gln Tyr Ser Lys
                1060                1065                1070
Leu Glu Asn Pro Ile Gly Tyr Arg Ser Thr Ala Glu Glu Arg Leu Gln
                1075                1080                1085
Ser Glu His Pro Glu Ala Phe Glu Tyr Tyr Lys Phe Cys Ile Gly Lys
                1090                1095                1100
Glu Asp Leu Val Glu Gln Ala Lys Gln Pro Glu Ile Ala Tyr Phe Glu
1105                1110                1115                1120
Lys Ile Ile Ala Phe Ile Thr Leu Val Leu Met Ala Phe Asp Ala Glu
                1125                1130                1135
Arg Ser Asp Gly Val Phe Lys Ile Leu Asn Lys Phe Lys Gly Ile Leu
                1140                1145                1150
Ser Ser Thr Glu Arg Glu Ile Ile Tyr Thr Gln Ser Leu Asp Asp Tyr
                1155                1160                1165
Val Thr Thr Phe Asp Asp Asn Met Thr Ile Asn Leu Glu Leu Asn Met
                1170                1175                1180
Asp Glu Leu His Lys Thr Ser Leu Pro Gly Val Thr Phe Lys Gln Trp
1185                1190                1195                1200
Trp Asn Asn Gln Ile Ser Arg Gly Asn Val Lys Pro His Tyr Arg Thr
                1205                1210                1215
Glu Gly His Phe Met Glu Phe Thr Arg Asp Thr Ala Ala Ser Val Ala
                1220                1225                1230
Ser Glu Ile Ser His Ser Pro Ala Arg Asp Phe Leu Val Arg Gly Ala
                1235                1240                1245
Val Gly Ser Gly Lys Ser Thr Gly Leu Pro Tyr His Leu Ser Lys Arg
                1250                1255                1260
Gly Arg Val Leu Met Leu Glu Pro Thr Arg Pro Leu Thr Asp Asn Met
1265                1270                1275                1280
His Lys Gln Leu Arg Ser Glu Pro Phe Asn Cys Phe Pro Thr Leu Arg
                1285                1290                1295
Met Arg Gly Lys Ser Thr Phe Gly Ser Ser Pro Ile Thr Val Met Thr
                1300                1305                1310
Ser Gly Phe Ala Leu His His Phe Ala Arg Asn Ile Ala Glu Val Lys
                1315                1320                1325
Thr Tyr Asp Phe Val Ile Ile Asp Glu Cys His Val Asn Asp Ala Ser
                1330                1335                1340
Ala Ile Ala Phe Arg Asn Leu Leu Phe Glu His Glu Phe Glu Gly Lys
1345                1350                1355                1360
Val Leu Lys Val Ser Ala Thr Pro Pro Gly Arg Glu Val Glu Phe Thr
                1365                1370                1375
Thr Gln Phe Pro Val Lys Leu Lys Ile Glu Glu Ala Leu Ser Phe Gln
                1380                1385                1390
Glu Phe Val Ser Leu Gln Gly Thr Gly Ala Asn Ala Asp Val Ile Ser
                1395                1400                1405
Cys Gly Asp Asn Ile Leu Val Tyr Val Ala Ser Tyr Asn Asp Val Asp
                1410                1415                1420
Ser Leu Gly Lys Leu Leu Val Gln Lys Gly Tyr Lys Val Ser Lys Ile
1425                1430                1435                1440
Asp Gly Arg Thr Met Lys Ser Gly Gly Thr Glu Ile Ile Thr Glu Gly
                1445                1450                1455
Thr Ser Val Lys Lys His Phe Ile Val Ala Thr Asn Ile Ile Glu Asn
                1460                1465                1470
```

-continued

```
Gly Val Thr  Ile Asp Ile Asp  Val Val Asp Phe Gly  Thr Lys Val
        1475             1480                 1485

Val Pro Val Leu Asp Val Asp  Asn Arg Ala Val Gln  Tyr Asn Lys Thr
1490             1495                 1500

Val Val Ser Tyr Gly Glu Arg  Ile Gln Lys Leu Gly  Arg Val Gly Arg
1505             1510                 1515                 1520

His Lys Glu Gly Val  Ala Leu Arg Ile Gly  Gln Thr Asn Lys Thr  Leu
            1525                 1530                 1535

Val Glu Ile Pro  Glu Met Val Ala Thr  Glu Ala Ala Phe Leu  Cys Phe
            1540                 1545                 1550

Met Tyr Asn  Leu Pro Val Thr Thr  Gln Ser Val Ser Thr  Thr Leu Leu
        1555                 1560                 1565

Glu Asn  Ala Thr Leu Leu Gln  Ala Arg Thr Met Ala  Gln Phe Glu Leu
        1570                 1575                 1580

Ser  Tyr Phe Tyr Thr Ile  Asn Phe Val Arg Phe  Asp Gly Ser Met His
1585                 1590                 1595                 1600

Pro Val Ile His Asp  Lys Leu Lys Arg Phe  Lys Leu His Thr Cys  Glu
            1605                 1610                 1615

Thr Phe Leu Asn  Lys Leu Ala Ile Pro  Asn Lys Gly Leu Ser  Ser Trp
            1620                 1625                 1630

Leu Thr Ser  Gly Glu Tyr Lys Arg  Leu Gly Tyr Ile Ala  Glu Asp Ala
        1635                 1640                 1645

Gly Ile  Arg Ile Pro Phe Val  Cys Lys Glu Ile Pro  Asp Ser Leu His
        1650                 1655                 1660

Glu  Glu Ile Trp His Ile  Val Val Ala His Lys  Gly Asp Ser Gly Ile
1665                 1670                 1675                 1680

Gly Arg Leu Thr Ser  Val Gln Ala Ala Lys  Val Val Tyr Thr Leu  Gln
            1685                 1690                 1695

Thr Asp Val His  Ser Ile Ala Arg Thr  Leu Ala Cys Ile Asn  Arg Arg
            1700                 1705                 1710

Ile Ala Asp  Glu Gln Met Lys Gln  Ser His Phe Glu Ala  Ala Thr Gly
        1715                 1720                 1725

Arg Ala  Phe Ser Phe Thr Asn  Tyr Ser Ile Gln Ser  Ile Phe Asp Thr
        1730                 1735                 1740

Leu  Lys Ala Asn Tyr Ala  Thr Lys His Thr Lys  Glu Asn Ile Ala Val
1745                 1750                 1755                 1760

Leu Gln Gln Ala Lys  Asp Gln Leu Leu Glu  Phe Ser Asn Leu Ala  Lys
            1765                 1770                 1775

Asp Gln Asp Val  Thr Gly Ile Ile Gln  Asp Phe Asn His Leu  Glu Thr
            1780                 1785                 1790

Ile Tyr Leu  Gln Ser Asp Ser Glu  Val Ala Lys His Leu  Lys Leu Lys
        1795                 1800                 1805

Ser His  Trp Asn Lys Ser Gln  Ile Thr Arg Asp Ile  Ile Ala Leu
        1810                 1815                 1820

Ser  Val Leu Ile Gly Gly  Gly Trp Met Leu Ala  Thr Tyr Phe Lys Asp
1825                 1830                 1835                 1840

Lys Phe Asn Glu Pro  Val Tyr Phe Gln Gly  Lys Lys Asn Gln Lys  His
            1845                 1850                 1855

Lys Leu Lys Met  Arg Glu Ala Arg Gly  Ala Arg Gly Gln Tyr  Glu Val
            1860                 1865                 1870

Ala Ala Glu  Pro Glu Ala Leu Glu  His Tyr Phe Gly Ser  Ala Tyr Asn
        1875                 1880                 1885
```

-continued

```
Asn Lys Gly Lys Arg Lys Gly Thr Thr Arg Gly Met Gly Ala Lys Ser
    1890            1895                1900
Arg Lys Phe Ile Asn Met Tyr Gly Phe Asp Pro Thr Asp Phe Ser Tyr
1905            1910                1915                1920
Ile Arg Phe Val Asp Pro Leu Thr Gly His Thr Ile Asp Glu Ser Thr
            1925                1930                1935
Asn Ala Pro Ile Asp Leu Val Gln His Glu Phe Gly Lys Val Arg Thr
            1940                1945                1950
Arg Met Leu Ile Asp Asp Glu Ile Glu Pro Gln Ser Leu Ser Thr His
        1955                1960                1965
Thr Thr Ile His Ala Tyr Leu Val Asn Ser Gly Thr Lys Lys Val Leu
    1970                1975                1980
Lys Val Asp Leu Thr Pro His Ser Ser Leu Arg Ala Ser Glu Lys Ser
1985                1990                1995                2000
Thr Ala Ile Met Gly Phe Pro Glu Arg Glu Asn Glu Leu Arg Gln Thr
            2005                2010                2015
Gly Met Ala Val Pro Val Ala Tyr Asp Gln Leu Pro Pro Lys Asn Glu
            2020                2025                2030
Asp Leu Thr Phe Glu Gly Glu Ser Leu Phe Lys Gly Pro Arg Asp Tyr
        2035                2040                2045
Asn Pro Ile Ser Ser Thr Ile Cys His Leu Thr Asn Glu Ser Asp Gly
2050                2055                2060
His Thr Thr Ser Leu Tyr Gly Ile Gly Phe Gly Pro Phe Ile Ile Thr
2065                2070                2075                2080
Asn Lys His Leu Phe Arg Arg Asn Asn Gly Thr Leu Leu Val Gln Ser
            2085                2090                2095
Leu His Gly Val Phe Lys Val Lys Asn Thr Thr Thr Leu Gln Gln His
            2100                2105                2110
Leu Ile Asp Gly Arg Asp Met Ile Ile Ile Arg Met Pro Lys Asp Phe
        2115                2120                2125
Pro Pro Phe Pro Gln Lys Leu Lys Phe Arg Glu Pro Gln Arg Glu Glu
        2130                2135                2140
Arg Ile Cys Leu Val Thr Thr Asn Phe Gln Thr Lys Ser Met Ser Ser
2145                2150                2155                2160
Met Val Ser Asp Thr Ser Cys Thr Phe Pro Ser Ser Asp Gly Ile Phe
            2165                2170                2175
Trp Lys His Trp Ile Gln Thr Lys Asp Gly Gln Cys Gly Ser Pro Leu
            2180                2185                2190
Val Ser Thr Arg Asp Gly Phe Ile Val Gly Ile His Ser Ala Ser Asn
        2195                2200                2205
Phe Thr Asn Thr Asn Asn Tyr Phe Thr Ser Val Pro Lys Asn Phe Met
    2210                2215                2220
Glu Leu Leu Thr Asn Gln Glu Ala Gln Gln Trp Val Ser Gly Trp Arg
2225                2230                2235                2240
Leu Asn Ala Asp Ser Val Leu Trp Gly Gly His Lys Val Phe Met Ser
            2245                2250                2255
Lys Pro Glu Glu Pro Phe Gln Pro Val Lys Glu Ala Thr Gln Leu Met
            2260                2265                2270
Asn Glu Leu Val Tyr Ser Gln Gly Glu Lys Arg Lys Trp Val Val Glu
        2275                2280                2285
Ala Leu Ser Gly Asn Leu Arg Pro Val Ala Glu Cys Pro Ser Gln Leu
    2290                2295                2300
Val Thr Lys His Val Val Lys Gly Lys Cys Pro Leu Phe Glu Leu Tyr
```

-continued

```
            2305                2310                2315                2320
Leu Gln Leu Asn Pro  Glu Lys Glu Ala Tyr  Phe Lys Pro Met Met  Gly
                2325                2330                2335
Ala Tyr Lys Pro  Ser Arg Leu Asn Arg  Glu Ala Phe Leu Lys  Asp Ile
            2340                2345                2350
Leu Lys Tyr  Ala Ser Glu Ile Glu  Ile Gly Asn Val Asp  Cys Asp Leu
        2355                2360                2365
Leu Glu  Leu Ala Ile Ser Met  Leu Val Thr Lys Leu  Lys Ala Leu Gly
    2370                2375                2380
Phe Pro Thr Val Asn  Tyr Ile Thr Asp Pro  Glu Glu Ile Phe Ser  Ala
2385                2390                2395                2400
Leu Asn Met Lys Ala  Ala Met Gly Ala Leu  Tyr Lys Gly Lys Lys  Lys
                2405                2410                2415
Glu Ala Leu Ser  Glu Leu Thr Leu Asp  Glu Gln Glu Ala Met  Leu Lys
            2420                2425                2430
Ala Ser Cys  Leu Arg Leu Tyr Thr  Gly Lys Leu Gly Ile  Trp Asn Gly
        2435                2440                2445
Ser Leu  Lys Ala Glu Leu Arg  Pro Ile Glu Lys Val  Glu Asn Asn Lys
    2450                2455                2460
Thr Arg Thr Phe Thr  Ala Ala Pro Ile Asp  Thr Leu Leu Ala Gly  Lys
2465                2470                2475                2480
Val Cys Val Asp Asp  Phe Asn Asn Gln Phe  Tyr Asp Leu Asn Ile  Lys
                2485                2490                2495
Ala Pro Trp Thr  Val Gly Met Thr Lys  Phe Tyr Gln Gly Trp  Asn Glu
            2500                2505                2510
Leu Met Glu  Ala Leu Pro Ser Gly  Trp Val Tyr Cys Asp  Ala Asp Gly
        2515                2520                2525
Ser Gln  Phe Asp Ser Ser Leu  Thr Pro Phe Leu Ile  Asn Ala Val Leu
    2530                2535                2540
Lys  Val Arg Leu Ala Phe  Met Glu Glu Trp Asp  Ile Gly Glu Gln  Met
2545                2550                2555                2560
Leu Arg Asn Leu Tyr  Thr Glu Ile Val Tyr  Thr Pro Ile Leu Thr  Pro
                2565                2570                2575
Asp Gly Thr Ile  Ile Lys Lys His Lys  Gly Asn Asn Ser Gly  Gln Pro
            2580                2585                2590
Ser Thr Val  Val Asp Asn Thr Leu  Met Val Ile Ile Ala  Met Leu Tyr
        2595                2600                2605
Thr Cys  Glu Lys Cys Gly Ile  Asn Lys Glu Glu Ile  Val Tyr Tyr Val
    2610                2615                2620
Asn  Gly Asp Asp Leu Leu  Ile Ala Ile His Pro  Asp Lys Ala Glu  Arg
2625                2630                2635                2640
Leu Ser Arg Phe Lys  Glu Ser Phe Gly Glu  Leu Gly Leu Lys Tyr  Glu
                2645                2650                2655
Phe Asp Cys Thr  Thr Arg Asp Lys Thr  Gln Leu Trp Phe Met  Ser His
            2660                2665                2670
Arg Ala Leu  Glu Arg Asp Gly Met  Tyr Ile Pro Lys Leu  Glu Glu Glu
        2675                2680                2685
Arg Ile  Val Ser Ile Leu Glu  Trp Asp Arg Ser Lys  Glu Pro Ser His
    2690                2695                2700
Arg  Leu Glu Ala Ile Cys  Ala Ser Met Ile Glu  Ala Trp Gly Tyr  Asp
2705                2710                2715                2720
Lys Leu Val Glu Glu  Ile Arg Asn Phe Tyr  Ala Trp Val Leu Glu  Gln
                2725                2730                2735
```

```
Ala Pro Tyr Ser  Gln Leu Ala Glu Glu  Gly Lys Ala Pro Tyr  Leu Ala
            2740                 2745                 2750

Glu Thr Ala  Leu Lys Phe Leu Tyr  Thr Ser Gln His Gly  Thr Asn Ser
        2755                 2760                 2765

Glu Ile Glu Glu Tyr  Leu Lys Val Leu Tyr  Asp Tyr Asp Ile Pro  Thr
        2770                 2775                 2780

Thr  Glu Asn Leu Tyr  Phe Gln Ser Gly Thr  Val Asp Ala Gly Ala  Asp
2785                 2790                 2795                 2800

Ala Gly Lys Lys Lys  Asp Gln Lys Asp Asp  Lys Val Ala Glu Gln  Ala
            2805                 2810                 2815

Ser Lys Asp Arg  Asp Val Asn Ala Gly  Thr Ser Gly Thr Phe  Ser Val
            2820                 2825                 2830

Pro Arg Ile  Asn Ala Met Ala Thr  Lys Leu Gln Tyr Pro  Arg Met Arg
        2835                 2840                 2845

Gly Glu  Val Val Val Asn Leu  Asn His Leu Leu Gly  Tyr Lys Pro Gln
        2850                 2855                 2860

Gln  Ile Asp Leu Ser Asn  Ala Arg Ala Thr His  Glu Gln Phe Ala Ala
2865                 2870                 2875                 2880

Trp His Gln Ala Val  Met Thr Ala Tyr Gly  Val Asn Glu Glu Gln  Met
            2885                 2890                 2895

Lys Ile Leu Leu  Asn Gly Phe Met Val  Trp Cys Ile Glu Asn  Gly Thr
            2900                 2905                 2910

Ser Pro Asn  Leu Asn Gly Thr Trp  Val Met Met Asp Gly  Glu Asp Gln
        2915                 2920                 2925

Val Ser  Tyr Pro Leu Lys Pro  Met Val Glu Asn Ala  Gln Pro Thr Leu
        2930                 2935                 2940

Arg  Gln Ile Met Thr His  Phe Ser Asp Leu Ala  Glu Ala Tyr Ile Glu
2945                 2950                 2955                 2960

Met Arg Asn Arg Glu  Arg Pro Tyr Met Pro  Arg Tyr Gly Leu Gln  Arg
            2965                 2970                 2975

Asn Ile Thr Asp  Met Ser Leu Ser Arg  Tyr Ala Phe Asp Phe  Tyr Glu
            2980                 2985                 2990

Leu Thr Ser  Lys Thr Pro Val Arg  Ala Arg Glu Ala His  Met Gln Met
        2995                 3000                 3005

Lys Ala  Ala Val Arg Asn  Ser Gly Thr Arg Leu  Phe Gly Leu Asp
        3010                 3015                 3020

Gly  Asn Val Gly Thr Ala  Glu Glu Asp Thr  Glu Arg His Thr Ala  His
3025                 3030                 3035                 3040

Asp Val Asn Arg Asn  Met His Thr Leu Leu  Gly Val Arg Gln
                3045                 3050

<210> SEQ ID NO 80
<211> LENGTH: 9
<212> TYPE: PRT
<213> ORGANISM: Homo Sapiens

<400> SEQUENCE: 80

Asn Ser Ser Gly Gly Asn Ser Gly Ser
                5

<210> SEQ ID NO 81
<211> LENGTH: 2755
<212> TYPE: DNA
<213> ORGANISM: Homo sapiens

<400> SEQUENCE: 81
```

-continued

```
ttaggacggg gcgatggcgg ctgagaggag ctgcgcgtgc gcgaacatgt aactggtggg       60
atctgcggcg gctcccagat gatggtcgtc ctcctgggcg cgacgaccct agtgctcgtc      120
gccgtgggcc catgggtgtt gtccgcagcc gcaggtggaa aaaatctaaa atctcctcaa      180
aaagtagagg tcgacatcat agatgacaac tttatcctga ggtggaacag gagcgatgag      240
tctgtcggga atgtgacttt ttcattcgat tatcaaaaaa ctgggatgga taattggata      300
aaattgtctg ggtgtcagaa tattactagt accaaatgca acttttcttc actcaagctg      360
aatgtttatg aagaaattaa attgcgtata agagcagaaa agaaaacac ttcttcatgg       420
tatgaggttg actcatttac accatttcgc aaagctcaga ttggtcctcc agaagtacat      480
ttagaagctg aagataaggc aatagtgata cacatctctc ctggaacaaa agatagtgtt      540
atgtgggctt tggatggttt aagctttaca tatagcttac ttatctggaa aaactcttca      600
ggtgtagaag aaaggattga aaatatttat tccagacata aaatttataa actctcacca      660
gagactactt attgtctaaa agttaaagca gcactactta cgtcatggaa aattggtgtc      720
tatagtccag tacattgtat aaagaccaca gttgaaaatg aactacctcc accagaaaat      780
atagaagtca gtgtccaaaa tcagaactat gttcttaaat gggattatac atatgcaaac      840
atgaccttc aagttcagtg gctccacgcc ttttttaaaaa ggaatcctgg aaaccatttg      900
tataaatgga acaaatacc tgactgtgaa aatgtcaaaa ctacccagtg tgtctttcct      960
caaaacgttt tccaaaaagg aatttaccttc ctccgcgtac aagcatctga tggaaataac     1020
acatcttttt ggtctgaaga gataaagttt gatactgaaa tacaagcttt cctacttcct     1080
ccagtcttta acattagatc ccttagtgat tcattccata tctatatcgg tgctccaaaa     1140
cagtctggaa acacgcctgt gatccaggat tatccactga tttatgaaat tatttttggg     1200
gaaaacactt caaatgctga gagaaaaatt atcgagaaaa aaactgatgt tacagttcct     1260
aatttgaaac cactgactgt atattgtgtg aagcccagag cacacaccat ggatgaaaag     1320
ctgaataaaa gcagtgtttt tagtgacgct gtatgtgaga aaacaaaacc aggaaatacc     1380
tctaaaattt ggcttatagt tggaatttgt attgcattat ttgctctccc gtttgtcatt     1440
tatgctgcga aagtcttctt gagatgcatc aattatgtct tctttccatc acttaaacct     1500
tcttccagta tagatgagta tttctctgaa cagccattga agaatcttct gctttcaact     1560
tctgaggaac aaatcgaaaa atgtttcata attgaaaata agcacaat tgctacagta       1620
gaagaaacta atcaaactga tgaagatcat aaaaaataca gttcccaaac tagccaagat     1680
tcaggaaatt attctaatga agatgaaagc gaaagtaaaa caagtgaaga actacagcag     1740
gactttgtat gaccagaaat gaactgtgtc aagtataagg ttttttcagca ggagttacac     1800
tgggagcctg aggtcctcac cttcctctca gtaactacag agaggacgtt tcctgtttag     1860
ggaaagaaaa aacatcttca gatcataggt cctaaaaata cggcaagct cttaactatt       1920
taaaaatgaa attacaggcc cgggcacggt ggctcacacc tgtaatccca gcactttggg     1980
aggctgaggc aggcagatca tgaggtcaag agatcgagac cagcctggcc aacgtggtga     2040
acccccatct ctactaaaaa tacaaaaatt agccgggtag taggtaggcg cgcgcctgtt     2100
gtcttagcta ctcaggaggc tgaggcagga gaatcgcttg aaaacaggag gtggaggttg     2160
cagtgagccg agatcacgcc actgcactcc agcctggtga cagcgtgaga ctctttaaaa     2220
aagaaatta aaagagttga gacaaacgtt tcctacattc ttttccatgt gtaaaatcat      2280
gaaaaagcct gtcaccggac ttgcattgga tgagatgagt cagaccaaaa cagtggccac     2340
```

```
ccgtcttcct cctgtgagcc taagtgcagc cgtgctagct gcgcaccgtg gctaaggatg    2400
acgtctgtgt tcctgtccat cactgatgct gctggctact gcatgtgcca cacctgtctg    2460
ttcgccattc ctaacattct gtttcattct tcctcgggag atatttcaaa catttggtct    2520
tttcttttaa cactgagggt aggcccttag gaaatttatt taggaaagtc tgaacacgtt    2580
atcacttggt tttctggaaa gtagcttacc ctagaaaaca gctgcaaatg ccagaaagat    2640
gatccctaaa aatgttgagg gacttctgtt cattcatccc gagaacattg gcttccacat    2700
cacagtatct accttacat ggtttaggat taaagccagg caatctttta ctatg          2755
```

<210> SEQ ID NO 82
<211> LENGTH: 9
<212> TYPE: PRT
<213> ORGANISM: Homo Sapiens

<400> SEQUENCE: 82

Gly Ser Glu Asn Leu Tyr Phe Gln Leu
              5

<210> SEQ ID NO 83
<211> LENGTH: 2897
<212> TYPE: DNA
<213> ORGANISM: Homo sapiens

<400> SEQUENCE: 83

```
cccgcactaa agacgcttct tcccggcggg taggaatccc gccggcgagc cgaacagttc      60
cccgagcgca gccgcggac caccacccgg ccgcacgggc cgcttttgtc ccccgcccgc      120
cgcttctgtc cgagaggccg cccgcgaggc gcatcctgac cgcgagcgtc gggtcccaga     180
gccgggcgcg gctggggccc gaggctagca tctctcggga gccgcaaggc gagagctgca     240
aagtttaatt agacacttca gaattttgat cacctaatgt tgatttcaga tgtaaaagtc     300
aagagaagac tctaaaaata gcaaagatgc ttttgagcca gaatgccttc atcttcagat     360
cacttaattt ggttctcatg gtgtatatca gcctcgtgtt tggtatttca tatgattcgc     420
ctgattacac agatgaatct tgcactttca agatatcatt gcgaaatttc cggtccatct     480
tatcatggga attaaaaaac cactccattg taccaactca ctatacattg ctgtatacaa     540
tcatgagtaa accagaagat ttgaaggtgg ttaagaactg tgcaaatacc acaagatcat     600
tttgtgacct cacagatgag tggagaagca cacacgaggc ctatgtcacc gtcctagaag     660
gattcagcgg gaacacaacg ttgttcagtt gctcacacaa tttctggctg gccatagaca     720
tgtcttttga ccaccagag tttgagattg ttggttttac caaccacatt aatgtgatgg     780
tgaaatttcc atctattgtt gaggaagaat tacagtttga tttatctctc gtcattgaag     840
aacagtcaga gggaattgtt aagaagcata aacccgaaat aaaggaaac atgagtggaa      900 atttcaccta tcatcattgac aagttaattc caaacacgaa ctactgtgta tctgtttatt    960
tagagcacag tgatgagcaa gcagtaataa agtctccctt aaaatgcacc ctccttccac    1020
ctggccagga atcagaatca gcagaatctg ccaaaatagg aggaataatt actgtgtttt    1080
tgatagcatt ggtcttgaca agcaccatag tgacactgaa atggattggt tatatatgct    1140
taagaaatag cctcccccaaa gtcttgaatt ttcataactt tttagcctgg ccatttccta    1200
acctgccacc gttggaagcc atggatatgg tggaggtcat ttacatcaac agaaagaaga    1260
aagtgtggga ttataattat gatgatgaaa gtgatagcga tactgaggca gcgcccagga    1320
caagtggcgg tggctatacc atgcatggac tgactgtcag gcctctgggt caggcctctg    1380
```

```
ccacctctac agaatcccag ttgatagacc cggagtccga ggaggagcct gacctgcctg   1440
aggttgatgt ggagctcccc acgatgccaa aggacagccc tcagcagttg aactcttga   1500 gtgggccctg tgagaggaga aagagtccac tccaggaccc ttttcccgaa gaggactaca   1560
gctccacgga ggggtctggg ggcagaatta ccttcaatgt ggacttaaac tctgtgtttt   1620
tgagagttct tgatgacgag gacagtgacg acttagaagc ccctctgatg ctatcgtctc   1680
atctggaaga gatggttgac ccagaggatc ctgataatgt gcaatcaaac catttgctgg   1740
ccagcgggga aggacacag ccaacctttc cagcccctc ttcagagggc ctgtggtccg    1800
aagatgctcc atctgatcaa agtgacactt ctgagtcaga tgttgacctt ggggatggtt   1860
atataatgag atgactccaa aactattgaa tgaacttgga cagacaagca cctacagggt   1920
tctttgtctc tgcatcctaa cttgctgcct tatcgtctgc aagtgttctc caagggaagg   1980
aggaggaaac tgtggtgttc ctttcttcca ggtgacatca cctatgcaca ttcccagtat   2040
ggggaccata gtatcattca gtgcattgtt tacatattca aagtggtgca ctttgaagga   2100
agcacatgtg cacctttcct ttacactaat gcacttagga tgtttctgca tcatgtctac   2160
cagggagcag ggttccccac agtttcagag gtggtccagg accctatgat atttctcttc   2220
tttcgttctt ttttttttt ttttgagaca gagtctcgtt ctgtcgccca agctggagcg   2280
caatggtgtg atcttggctc actgcaacat ccgcctcccg ggttcaggtg attctcctgc   2340
ctcagcctcc ctcgcaagta gctgggatta caggcgcctg ccaccatgcc tagcaaattt   2400 ttgtatttt agtggagaca ggatttacc atgttggcca ggctggtctc gaactcctga   2460
cctcaagtga tctgccctcc tcagcctcgt aaagtgctgg gattacaggg gtgagccgct   2520
gtgcctggct ggccctgtga tatttctgtg aaataaattg gccagggtg ggagcaggga   2580 aagaaaagga aaatagtagc aagagctgca aagcaggcag gaaggaggaa ggagagccag   2640
gtgagcagtg gagagaaggg gggccctgca caaggaaaca gggaagagcc atcgaagttt   2700
cagtcggtga gccttgggca cctcacccat gtcacatcct gtctcctgca attggaattc   2760 cacccttgtcc agccctcccc agttaaagtg gggaagacag actttaggat cacgtgtgtg   2820
actaatacag aaaggaaaca tggcgtcggg gagagggata aaacctgaat gccatatttt   2880
aagttaaaaa aaaaaaa                                                 2897
```

<210> SEQ ID NO 84
<211> LENGTH: 3054
<212> TYPE: PRT
<213> ORGANISM: Homo sapiens
<400> SEQUENCE: 84

```
Met Ala Leu Ile Phe Gly Thr Val Asn Ala Asn Ile Leu Lys Glu Val
1               5                   10                  15

Phe Gly Gly Ala Arg Met Ala Cys Val Thr Ser Ala His Met Ala Gly
            20                  25                  30

Ala Asn Gly Ser Ile Leu Lys Lys Ala Glu Glu Thr Ser Arg Ala Ile
        35                  40                  45

Met His Lys Pro Val Ile Phe Gly Glu Asp Tyr Ile Thr Glu Ala Asp
    50                  55                  60

Leu Pro Tyr Thr Pro Leu His Leu Glu Val Asp Ala Glu Met Glu Arg
65                  70                  75                  80

Met Tyr Tyr Leu Gly Arg Arg Ala Leu Thr His Gly Lys Arg Arg Lys
                85                  90                  95

Val Ser Val Asn Asn Lys Arg Asn Arg Arg Arg Lys Val Ala Lys Thr
```

```
                100                 105                 110
Tyr Val Gly Arg Asp Ser Ile Val Glu Lys Ile Val Pro His Thr
            115                 120                 125
Glu Arg Lys Val Asp Thr Thr Ala Ala Val Glu Asp Ile Cys Asn Glu
130                 135                 140
Ala Thr Thr Gln Leu Val His Asn Ser Met Pro Lys Arg Lys Gln
145                 150                 155                 160
Lys Asn Phe Leu Pro Ala Thr Ser Leu Ser Asn Val Tyr Ala Gln Thr
                165                 170                 175
Trp Ser Ile Val Arg Lys Arg His Met Gln Val Glu Ile Ile Ser Lys
            180                 185                 190
Lys Ser Val Arg Ala Arg Val Lys Arg Phe Glu Gly Ser Val Gln Leu
            195                 200                 205
Phe Ala Ser Val Arg His Met Tyr Gly Glu Arg Lys Arg Val Asp Leu
            210                 215                 220
Arg Ile Asp Asn Trp Gln Gln Glu Thr Leu Leu Asp Leu Ala Lys Arg
225                 230                 235                 240
Phe Lys Asn Glu Arg Val Asp Gln Ser Lys Leu Thr Phe Gly Ser Ser
                245                 250                 255
Gly Leu Val Leu Arg Gln Gly Ser Tyr Gly Pro Ala His Trp Tyr Arg
            260                 265                 270
His Gly Met Phe Ile Val Arg Gly Arg Ser Asp Gly Met Leu Val Asp
            275                 280                 285
Ala Arg Ala Lys Val Thr Phe Ala Val Cys His Ser Met Thr His Tyr
            290                 295                 300
Ser Asp Lys Ser Ile Ser Glu Ala Phe Phe Ile Pro Tyr Ser Lys Lys
305                 310                 315                 320
Phe Leu Glu Leu Arg Pro Asp Gly Ile Ser His Glu Cys Thr Arg Gly
                325                 330                 335
Val Ser Val Glu Arg Cys Gly Glu Val Ala Ala Ile Leu Thr Gln Ala
            340                 345                 350
Leu Ser Pro Cys Gly Lys Ile Thr Cys Lys Arg Cys Met Val Glu Thr
            355                 360                 365
Pro Asp Ile Val Glu Gly Glu Ser Gly Glu Ser Val Thr Asn Gln Gly
            370                 375                 380
Lys Leu Leu Ala Met Leu Lys Glu Gln Tyr Pro Asp Phe Pro Met Ala
385                 390                 395                 400
Glu Lys Leu Leu Thr Arg Phe Leu Gln Gln Lys Ser Leu Val Asn Thr
                405                 410                 415
Asn Leu Thr Ala Cys Val Ser Val Lys Gln Leu Ile Gly Asp Arg Lys
            420                 425                 430
Gln Ala Pro Phe Thr His Val Leu Ala Val Ser Glu Ile Leu Phe Lys
            435                 440                 445
Gly Asn Lys Leu Thr Gly Ala Asp Leu Glu Glu Ala Ser Thr His Met
            450                 455                 460
Leu Glu Ile Ala Arg Phe Leu Asn Asn Arg Thr Glu Asn Met Arg Ile
465                 470                 475                 480
Gly His Leu Gly Ser Phe Arg Asn Lys Ile Ser Ser Lys Ala His Val
                485                 490                 495
Asn Asn Ala Leu Met Cys Asp Asn Gln Leu Asp Gln Asn Gly Asn Phe
            500                 505                 510
Ile Trp Gly Leu Arg Gly Ala His Ala Lys Arg Phe Leu Lys Gly Phe
            515                 520                 525
```

```
Phe Thr Glu Ile Asp Pro Asn Glu Gly Tyr Asp Lys Tyr Val Ile Arg
    530                 535                 540
Lys His Ile Arg Gly Ser Arg Lys Leu Ala Ile Gly Asn Leu Ile Met
545                 550                 555                 560
Ser Thr Asp Phe Gln Thr Leu Arg Gln Gln Ile Gln Gly Glu Thr Ile
                565                 570                 575
Glu Arg Lys Glu Ile Gly Asn His Cys Ile Ser Met Arg Asn Gly Asn
            580                 585                 590
Tyr Val Tyr Pro Cys Cys Cys Val Thr Leu Glu Asp Gly Lys Ala Gln
        595                 600                 605
Tyr Ser Asp Leu Lys His Pro Thr Lys Arg His Leu Val Ile Gly Asn
    610                 615                 620
Ser Gly Asp Ser Lys Tyr Leu Asp Leu Pro Val Leu Asn Glu Glu Lys
625                 630                 635                 640
Met Tyr Ile Ala Asn Glu Gly Tyr Cys Tyr Met Asn Ile Phe Phe Ala
                645                 650                 655
Leu Leu Val Asn Val Lys Glu Glu Asp Ala Lys Asp Phe Thr Lys Phe
            660                 665                 670
Ile Arg Asp Thr Ile Val Pro Lys Leu Gly Ala Trp Pro Thr Met Gln
        675                 680                 685
Asp Val Ala Thr Ala Cys Tyr Leu Leu Ser Ile Leu Tyr Pro Asp Val
    690                 695                 700
Leu Arg Ala Glu Leu Pro Arg Ile Leu Val Asp His Asp Asn Lys Thr
705                 710                 715                 720
Met His Val Leu Asp Ser Tyr Gly Ser Arg Thr Thr Gly Tyr His Met
                725                 730                 735
Leu Lys Met Asn Thr Thr Ser Gln Leu Ile Glu Phe Val His Ser Gly
            740                 745                 750
Leu Glu Ser Glu Met Lys Thr Tyr Asn Val Gly Gly Met Asn Arg Asp
        755                 760                 765
Val Val Thr Gln Gly Ala Ile Glu Met Leu Ile Lys Ser Ile Tyr Lys
    770                 775                 780
Pro His Leu Met Lys Gln Leu Leu Glu Glu Pro Tyr Ile Ile Val
785                 790                 795                 800
Leu Ala Ile Val Ser Pro Ser Ile Leu Ile Ala Met Tyr Asn Ser Gly
                805                 810                 815
Thr Phe Glu Gln Ala Leu Gln Met Trp Leu Pro Asn Thr Met Arg Leu
            820                 825                 830
Ala Asn Leu Ala Ala Ile Leu Ser Ala Leu Ala Gln Lys Leu Thr Leu
        835                 840                 845
Ala Asp Leu Phe Val Gln Gln Arg Asn Leu Ile Asn Glu Tyr Ala Gln
    850                 855                 860
Val Ile Leu Asp Asn Leu Ile Asp Gly Val Arg Val Asn His Ser Leu
865                 870                 875                 880
Ser Leu Ala Met Glu Ile Val Thr Ile Lys Leu Ala Thr Gln Glu Met
                885                 890                 895
Asp Met Ala Leu Arg Glu Gly Gly Tyr Ala Val Thr Ser Glu Lys Val
            900                 905                 910
His Glu Met Leu Glu Lys Asn Tyr Val Lys Ala Leu Lys Asp Ala Trp
        915                 920                 925
Asp Glu Leu Thr Trp Leu Glu Lys Phe Ser Ala Ile Arg His Ser Arg
    930                 935                 940
```

```
Lys Leu Leu Lys Phe Gly Arg Lys Pro Leu Ile Met Lys Asn Thr Val
945                 950                 955                 960

Asp Cys Gly Gly His Ile Asp Leu Ser Val Lys Ser Leu Phe Lys Phe
                965                 970                 975

His Leu Glu Leu Leu Lys Gly Thr Ile Ser Arg Ala Val Asn Gly Gly
            980                 985                 990

Ala Arg Lys Val Arg Val Ala Lys Asn Ala Met Thr Lys Gly Val Phe
        995                 1000                1005

Leu Lys Ile Tyr Ser Met Leu Pro Asp Val Tyr Lys Phe Ile Thr
    1010                1015                1020

Val Ser Ser Val Leu Ser Leu Leu Leu Thr Phe Leu Phe Gln Ile
    1025                1030                1035

Asp Cys Met Ile Arg Ala His Arg Glu Ala Lys Val Ala Ala Gln
    1040                1045                1050

Leu Gln Lys Glu Ser Glu Trp Asp Asn Ile Ile Asn Arg Thr Phe
    1055                1060                1065

Gln Tyr Ser Lys Leu Glu Asn Pro Ile Gly Tyr Arg Ser Thr Ala
    1070                1075                1080

Glu Glu Arg Leu Gln Ser Glu His Pro Glu Ala Phe Glu Tyr Tyr
    1085                1090                1095

Lys Phe Cys Ile Gly Lys Glu Asp Leu Val Glu Gln Ala Lys Gln
    1100                1105                1110

Pro Glu Ile Ala Tyr Phe Glu Lys Ile Ile Ala Phe Ile Thr Leu
    1115                1120                1125

Val Leu Met Ala Phe Asp Ala Glu Arg Ser Asp Gly Val Phe Lys
    1130                1135                1140

Ile Leu Asn Lys Phe Lys Gly Ile Leu Ser Ser Thr Glu Arg Glu
    1145                1150                1155

Ile Ile Tyr Thr Gln Ser Leu Asp Asp Tyr Val Thr Thr Phe Asp
    1160                1165                1170

Asp Asn Met Thr Ile Asn Leu Glu Leu Asn Met Asp Glu Leu His
    1175                1180                1185

Lys Thr Ser Leu Pro Gly Val Thr Phe Lys Gln Trp Trp Asn Asn
    1190                1195                1200

Gln Ile Ser Arg Gly Asn Val Lys Pro His Tyr Arg Thr Glu Gly
    1205                1210                1215

His Phe Met Glu Phe Thr Arg Asp Thr Ala Ala Ser Val Ala Ser
    1220                1225                1230

Glu Ile Ser His Ser Pro Ala Arg Asp Phe Leu Val Arg Gly Ala
    1235                1240                1245

Val Gly Ser Gly Lys Ser Thr Gly Leu Pro Tyr His Leu Ser Lys
    1250                1255                1260

Arg Gly Arg Val Leu Met Leu Glu Pro Thr Arg Pro Leu Thr Asp
    1265                1270                1275

Asn Met His Lys Gln Leu Arg Ser Glu Pro Phe Asn Cys Phe Pro
    1280                1285                1290

Thr Leu Arg Met Arg Gly Lys Ser Thr Phe Gly Ser Ser Pro Ile
    1295                1300                1305

Thr Val Met Thr Ser Gly Phe Ala Leu His His Phe Ala Arg Asn
    1310                1315                1320

Ile Ala Glu Val Lys Thr Tyr Asp Phe Val Ile Ile Asp Glu Cys
    1325                1330                1335

His Val Asn Asp Ala Ser Ala Ile Ala Phe Arg Asn Leu Leu Phe
```

-continued

```
              1340                1345                1350
Glu  His  Glu  Phe  Glu  Gly  Lys  Val  Leu  Lys  Val  Ser  Ala  Thr  Pro
     1355                1360                1365
Pro  Gly  Arg  Glu  Val  Glu  Phe  Thr  Thr  Gln  Phe  Pro  Val  Lys  Leu
     1370                1375                1380
Lys  Ile  Glu  Glu  Ala  Leu  Ser  Phe  Gln  Glu  Phe  Val  Ser  Leu  Gln
     1385                1390                1395
Gly  Thr  Gly  Ala  Asn  Ala  Asp  Val  Ile  Ser  Cys  Gly  Asp  Asn  Ile
     1400                1405                1410
Leu  Val  Tyr  Val  Ala  Ser  Tyr  Asn  Asp  Val  Asp  Ser  Leu  Gly  Lys
     1415                1420                1425
Leu  Leu  Val  Gln  Lys  Gly  Tyr  Lys  Val  Ser  Lys  Ile  Asp  Gly  Arg
     1430                1435                1440
Thr  Met  Lys  Ser  Gly  Gly  Thr  Glu  Ile  Ile  Thr  Glu  Gly  Thr  Ser
     1445                1450                1455
Val  Lys  Lys  His  Phe  Ile  Val  Ala  Thr  Asn  Ile  Ile  Glu  Asn  Gly
     1460                1465                1470
Val  Thr  Ile  Asp  Ile  Asp  Val  Val  Asp  Phe  Gly  Thr  Lys  Val
     1475                1480                1485
Val  Pro  Val  Leu  Asp  Val  Asp  Asn  Arg  Ala  Val  Gln  Tyr  Asn  Lys
     1490                1495                1500
Thr  Val  Val  Ser  Tyr  Gly  Glu  Arg  Ile  Gln  Lys  Leu  Gly  Arg  Val
     1505                1510                1515
Gly  Arg  His  Lys  Glu  Gly  Val  Ala  Leu  Arg  Ile  Gly  Gln  Thr  Asn
     1520                1525                1530
Lys  Thr  Leu  Val  Glu  Ile  Pro  Glu  Met  Val  Ala  Thr  Glu  Ala  Ala
     1535                1540                1545
Phe  Leu  Cys  Phe  Met  Tyr  Asn  Leu  Pro  Val  Thr  Thr  Gln  Ser  Val
     1550                1555                1560
Ser  Thr  Thr  Leu  Leu  Glu  Asn  Ala  Thr  Leu  Leu  Gln  Ala  Arg  Thr
     1565                1570                1575
Met  Ala  Gln  Phe  Glu  Leu  Ser  Tyr  Phe  Tyr  Thr  Ile  Asn  Phe  Val
     1580                1585                1590
Arg  Phe  Asp  Gly  Ser  Met  His  Pro  Val  Ile  His  Asp  Lys  Leu  Lys
     1595                1600                1605
Arg  Phe  Lys  Leu  His  Thr  Cys  Glu  Thr  Phe  Leu  Asn  Lys  Leu  Ala
     1610                1615                1620
Ile  Pro  Asn  Lys  Gly  Leu  Ser  Ser  Trp  Leu  Thr  Ser  Gly  Glu  Tyr
     1625                1630                1635
Lys  Arg  Leu  Gly  Tyr  Ile  Ala  Glu  Asp  Ala  Gly  Ile  Arg  Ile  Pro
     1640                1645                1650
Phe  Val  Cys  Lys  Glu  Ile  Pro  Asp  Ser  Leu  His  Glu  Glu  Ile  Trp
     1655                1660                1665
His  Ile  Val  Val  Ala  His  Lys  Gly  Asp  Ser  Gly  Ile  Gly  Arg  Leu
     1670                1675                1680
Thr  Ser  Val  Gln  Ala  Ala  Lys  Val  Val  Tyr  Thr  Leu  Gln  Thr  Asp
     1685                1690                1695
Val  His  Ser  Ile  Ala  Arg  Thr  Leu  Ala  Cys  Ile  Asn  Arg  Arg  Ile
     1700                1705                1710
Ala  Asp  Glu  Gln  Met  Lys  Gln  Ser  His  Phe  Glu  Ala  Ala  Thr  Gly
     1715                1720                1725
Arg  Ala  Phe  Ser  Phe  Thr  Asn  Tyr  Ser  Ile  Gln  Ser  Ile  Phe  Asp
     1730                1735                1740
```

-continued

```
Thr Leu Lys Ala Asn Tyr Ala Thr Lys His Thr Lys Glu Asn Ile
1745                1750                1755

Ala Val Leu Gln Gln Ala Lys Asp Gln Leu Leu Glu Phe Ser Asn
1760                1765                1770

Leu Ala Lys Asp Gln Asp Val Thr Gly Ile Ile Gln Asp Phe Asn
1775                1780                1785

His Leu Glu Thr Ile Tyr Leu Gln Ser Asp Ser Glu Val Ala Lys
1790                1795                1800

His Leu Lys Leu Lys Ser His Trp Asn Lys Ser Gln Ile Thr Arg
1805                1810                1815

Asp Ile Ile Ile Ala Leu Ser Val Leu Ile Gly Gly Gly Trp Met
1820                1825                1830

Leu Ala Thr Tyr Phe Lys Asp Lys Phe Asn Glu Pro Val Tyr Phe
1835                1840                1845

Gln Gly Lys Lys Asn Gln Lys His Lys Leu Lys Met Arg Glu Ala
1850                1855                1860

Arg Gly Ala Arg Gly Gln Tyr Glu Val Ala Ala Glu Pro Glu Ala
1865                1870                1875

Leu Glu His Tyr Phe Gly Ser Ala Tyr Asn Asn Lys Gly Lys Arg
1880                1885                1890

Lys Gly Thr Thr Arg Gly Met Gly Ala Lys Ser Arg Lys Phe Ile
1895                1900                1905

Asn Met Tyr Gly Phe Asp Pro Thr Asp Phe Ser Tyr Ile Arg Phe
1910                1915                1920

Val Asp Pro Leu Thr Gly His Thr Ile Asp Glu Ser Thr Asn Ala
1925                1930                1935

Pro Ile Asp Leu Val Gln His Glu Phe Gly Lys Val Arg Thr Arg
1940                1945                1950

Met Leu Ile Asp Asp Glu Ile Glu Pro Gln Ser Leu Ser Thr His
1955                1960                1965

Thr Thr Ile His Ala Tyr Leu Val Asn Ser Gly Thr Lys Lys Val
1970                1975                1980

Leu Lys Val Asp Leu Thr Pro His Ser Ser Leu Arg Ala Ser Glu
1985                1990                1995

Lys Ser Thr Ala Ile Met Gly Phe Pro Glu Arg Glu Asn Glu Leu
2000                2005                2010

Arg Gln Thr Gly Met Ala Val Pro Val Ala Tyr Asp Gln Leu Pro
2015                2020                2025

Pro Lys Asn Glu Asp Leu Thr Phe Glu Gly Glu Ser Leu Phe Lys
2030                2035                2040

Gly Pro Arg Asp Tyr Asn Pro Ile Ser Ser Thr Ile Cys His Leu
2045                2050                2055

Thr Asn Glu Ser Asp Gly His Thr Thr Ser Leu Tyr Gly Ile Gly
2060                2065                2070

Phe Gly Pro Phe Ile Ile Thr Asn Lys His Leu Phe Arg Arg Asn
2075                2080                2085

Asn Gly Thr Leu Leu Val Gln Ser Leu His Gly Val Phe Lys Val
2090                2095                2100

Lys Asn Thr Thr Thr Leu Gln Gln His Leu Ile Asp Gly Arg Asp
2105                2110                2115

Met Ile Ile Ile Arg Met Pro Lys Asp Phe Pro Pro Phe Pro Gln
2120                2125                2130
```

-continued

```
Lys Leu Lys Phe Arg Glu Pro Gln Arg Glu Arg Ile Cys Leu
2135                2140                2145

Val Thr Thr Asn Phe Gln Thr Lys Ser Met Ser Met Val Ser
    2150                2155                2160

Asp Thr Ser Cys Thr Phe Pro Ser Ser Asp Gly Ile Phe Trp Lys
    2165                2170                2175

His Trp Ile Gln Thr Lys Asp Gly Gln Cys Gly Ser Pro Leu Val
    2180                2185                2190

Ser Thr Arg Asp Gly Phe Ile Val Gly Ile His Ser Ala Ser Asn
    2195                2200                2205

Phe Thr Asn Thr Asn Tyr Phe Thr Ser Val Pro Lys Asn Phe
    2210                2215                2220

Met Glu Leu Leu Thr Asn Gln Glu Ala Gln Gln Trp Val Ser Gly
    2225                2230                2235

Trp Arg Leu Asn Ala Asp Ser Val Leu Trp Gly Gly His Lys Val
    2240                2245                2250

Phe Met Ser Lys Pro Glu Glu Pro Phe Gln Pro Val Lys Glu Ala
    2255                2260                2265

Thr Gln Leu Met Asn Glu Leu Val Tyr Ser Gln Gly Glu Lys Arg
    2270                2275                2280

Lys Trp Val Val Glu Ala Leu Ser Gly Asn Leu Arg Pro Val Ala
    2285                2290                2295

Glu Cys Pro Ser Gln Leu Val Thr Lys His Val Lys Gly Lys
    2300                2305                2310

Cys Pro Leu Phe Glu Leu Tyr Leu Gln Leu Asn Pro Glu Lys Glu
    2315                2320                2325

Ala Tyr Phe Lys Pro Met Met Gly Ala Tyr Lys Pro Ser Arg Leu
    2330                2335                2340

Asn Arg Glu Ala Phe Leu Lys Asp Ile Leu Lys Tyr Ala Ser Glu
    2345                2350                2355

Ile Glu Ile Gly Asn Val Asp Cys Asp Leu Leu Glu Leu Ala Ile
    2360                2365                2370

Ser Met Leu Val Thr Lys Leu Lys Ala Leu Gly Phe Pro Thr Val
    2375                2380                2385

Asn Tyr Ile Thr Asp Pro Glu Glu Ile Phe Ser Ala Leu Asn Met
    2390                2395                2400

Lys Ala Ala Met Gly Ala Leu Tyr Lys Gly Lys Lys Lys Glu Ala
    2405                2410                2415

Leu Ser Glu Leu Thr Leu Asp Glu Gln Glu Ala Met Leu Lys Ala
    2420                2425                2430

Ser Cys Leu Arg Leu Tyr Thr Gly Lys Leu Gly Ile Trp Asn Gly
    2435                2440                2445

Ser Leu Lys Ala Glu Leu Arg Pro Ile Glu Lys Val Glu Asn Asn
    2450                2455                2460

Lys Thr Arg Thr Phe Thr Ala Ala Pro Ile Asp Thr Leu Leu Ala
    2465                2470                2475

Gly Lys Val Cys Val Asp Asp Phe Asn Asn Gln Phe Tyr Asp Leu
    2480                2485                2490

Asn Ile Lys Ala Pro Trp Thr Val Gly Met Thr Lys Phe Tyr Gln
    2495                2500                2505

Gly Trp Asn Glu Leu Met Glu Ala Leu Pro Ser Gly Trp Val Tyr
    2510                2515                2520

Cys Asp Ala Asp Gly Ser Gln Phe Asp Ser Ser Leu Thr Pro Phe
```

-continued

```
            2525                2530                2535

Leu Ile Asn Ala Val Leu Lys Val Arg Leu Ala Phe Met Glu Glu
        2540                2545                2550

Trp Asp Ile Gly Glu Gln Met Leu Arg Asn Leu Tyr Thr Glu Ile
    2555                2560                2565

Val Tyr Thr Pro Ile Leu Thr Pro Asp Gly Thr Ile Ile Lys Lys
    2570                2575                2580

His Lys Gly Asn Asn Ser Gly Gln Pro Ser Thr Val Val Asp Asn
    2585                2590                2595

Thr Leu Met Val Ile Ile Ala Met Leu Tyr Thr Cys Glu Lys Cys
    2600                2605                2610

Gly Ile Asn Lys Glu Glu Ile Val Tyr Tyr Val Asn Gly Asp Asp
    2615                2620                2625

Leu Leu Ile Ala Ile His Pro Asp Lys Ala Glu Arg Leu Ser Arg
    2630                2635                2640

Phe Lys Glu Ser Phe Gly Glu Leu Gly Leu Lys Tyr Glu Phe Asp
    2645                2650                2655

Cys Thr Thr Arg Asp Lys Thr Gln Leu Trp Phe Met Ser His Arg
    2660                2665                2670

Ala Leu Glu Arg Asp Gly Met Tyr Ile Pro Lys Leu Glu Glu Glu
    2675                2680                2685

Arg Ile Val Ser Ile Leu Glu Trp Asp Arg Ser Lys Glu Pro Ser
    2690                2695                2700

His Arg Leu Glu Ala Ile Cys Ala Ser Met Ile Glu Ala Trp Gly
    2705                2710                2715

Tyr Asp Lys Leu Val Glu Glu Ile Arg Asn Phe Tyr Ala Trp Val
    2720                2725                2730

Leu Glu Gln Ala Pro Tyr Ser Gln Leu Ala Glu Glu Gly Lys Ala
    2735                2740                2745

Pro Tyr Leu Ala Glu Thr Ala Leu Lys Phe Leu Tyr Thr Ser Gln
    2750                2755                2760

His Gly Thr Asn Ser Glu Ile Glu Glu Tyr Leu Lys Val Leu Tyr
    2765                2770                2775

Asp Tyr Asp Ile Pro Thr Thr Glu Asn Leu Tyr Phe Gln Ser Gly
    2780                2785                2790

Thr Val Asp Ala Gly Ala Asp Ala Gly Lys Lys Lys Asp Gln Lys
    2795                2800                2805

Asp Asp Lys Val Ala Glu Gln Ala Ser Lys Asp Arg Asp Val Asn
    2810                2815                2820

Ala Gly Thr Ser Gly Thr Phe Ser Val Pro Arg Ile Asn Ala Met
    2825                2830                2835

Ala Thr Lys Leu Gln Tyr Pro Arg Met Arg Gly Glu Val Val Val
    2840                2845                2850

Asn Leu Asn His Leu Leu Gly Tyr Lys Pro Gln Gln Ile Asp Leu
    2855                2860                2865

Ser Asn Ala Arg Ala Thr His Glu Gln Phe Ala Ala Trp His Gln
    2870                2875                2880

Ala Val Met Thr Ala Tyr Gly Val Asn Glu Glu Gln Met Lys Ile
    2885                2890                2895

Leu Leu Asn Gly Phe Met Val Trp Cys Ile Glu Asn Gly Thr Ser
    2900                2905                2910

Pro Asn Leu Asn Gly Thr Trp Val Met Met Asp Gly Glu Asp Gln
    2915                2920                2925
```

-continued

| Val | Ser | Tyr | Pro | Leu | Lys | Pro | Met | Val | Glu | Asn | Ala | Gln | Pro | Thr |
| | 2930 | | | | 2935 | | | | 2940 | | | | | |

| Leu | Arg | Gln | Ile | Met | Thr | His | Phe | Ser | Asp | Leu | Ala | Glu | Ala | Tyr |
| | 2945 | | | | 2950 | | | | 2955 | | | | | |

| Ile | Glu | Met | Arg | Asn | Arg | Glu | Arg | Pro | Tyr | Met | Pro | Arg | Tyr | Gly |
| | 2960 | | | | 2965 | | | | 2970 | | | | | |

| Leu | Gln | Arg | Asn | Ile | Thr | Asp | Met | Ser | Leu | Ser | Arg | Tyr | Ala | Phe |
| | 2975 | | | | 2980 | | | | 2985 | | | | | |

| Asp | Phe | Tyr | Glu | Leu | Thr | Ser | Lys | Thr | Pro | Val | Arg | Ala | Arg | Glu |
| | 2990 | | | | 2995 | | | | 3000 | | | | | |

| Ala | His | Met | Gln | Met | Lys | Ala | Ala | Ala | Val | Arg | Asn | Ser | Gly | Thr |
| | 3005 | | | | 3010 | | | | 3015 | | | | | |

| Arg | Leu | Phe | Gly | Leu | Asp | Gly | Asn | Val | Gly | Thr | Ala | Glu | Glu | Asp |
| | 3020 | | | | 3025 | | | | 3030 | | | | | |

| Thr | Glu | Arg | His | Thr | Ala | His | Asp | Val | Asn | Arg | Asn | Met | His | Thr |
| | 3035 | | | | 3040 | | | | 3045 | | | | | |

Leu Leu Gly Val Arg Gln
    3050

<210> SEQ ID NO 85
<211> LENGTH: 4157
<212> TYPE: DNA
<213> ORGANISM: Homo sapiens

<400> SEQUENCE: 85

```
agcggggcgg ggcgccagcg ctgccttttc tcctgccggg tagtttcgct ttcctgcgca      60
gagtctgcgg aggggctcgg ctgcaccggg gggatcgcgc ctggcagacc ccagaccgag     120
cagaggcgac ccagcgcgct cgggagaggc tgcaccgccg cgccccgcc tagcccttcc      180
ggatcctgcg cgcagaaaag tttcatttgc tgtatgccat cctcgagagc tgtctaggtt     240
aacgttcgca ctctgtgtat ataacctcga cagtcttggc acctaacgtg ctgtgcgtag     300
ctgctccttt ggttgaatcc ccaggcccct gttggggcac aaggtggcag gatgtctcag     360
tggtacgaac ttcagcagct tgactcaaaa ttcctggagc aggttcacca gctttatgat     420
gacagtttc cctatggaaat cagacagtac ctggcacagt ggttagaaaa gcaagactgg     480
gagcacgctg ccaatgatgt tcatttgcc accatccgtt tcatgaccct cctgtcacag     540
ctggatgatc aatatagtcg ctttctcttg gagaataact tcttgctaca gcataacata     600
aggaaaagca agcgtaatct tcaggataat tttcaggaag acccaatcca gatgtctatg     660
atcatttaca gctgtctgaa ggaagaaagg aaaattctgg aaaacgccca gagatttaat     720
caggctcagt cggggaatat tcagagcaca gtgatgttaca caaacagaa agagcttgac     780
agtaaagtca gaaatgtgaa ggacaaggtt atgtgtatag agcatgaaat caagagcctg     840
gaagatttac aagatgaata tgacttcaaa tgcaaaacct gcagaacag agaacacgag     900
accaatggtg tggcaaagag tgatcagaaa caagaacagc tgttactcaa gaagatgtat     960
ttaatgcttg acaataagag aaaggaagta gttcacaaaa taatagagtt gctgaatgtc    1020
actgaactta cccagaatgc cctgattaat gatgaactag tggagtggaa gcggagacag    1080
cagagcgcct gtattggggg gccgcccaat gcttgcttgg atcagctgca gaactggttc    1140
actatagttg cggagagtct gcagcaagtt cggcagcagc ttaaaagtt ggaggaattg    1200
gaacagaaat acacctacga acatgaccct atcacaaaaa acaaacaagt gttatgggac    1260
cgcaccttca gtcttttcca gcagctcatt cagagctcgt ttgtggtgga aagacagccc    1320
```

```
tgcatgccaa cgcaccctca gaggccgctg gtcttgaaga caggggtcca gttcactgtg    1380
aagttgagac tgttggtgaa attgcaagag ctgaattata atttgaaagt caaagtctta    1440
tttgataaag atgtgaatga gagaaataca gtaaaaggat ttaggaagtt caacattttg    1500
ggcacgcaca caaaagtgat gaacatggag gagtccacca atggcagtct ggcggctgaa    1560
tttcggcacc tgcaattgaa agaacagaaa atgctggca ccagaacgaa tgagggtcct     1620
ctcatcgtta ctgaagagct tcactccctt agttttgaaa cccaattgtg ccagcctggt    1680
ttggtaattg acctcgagac gacctctctg cccgttgtgg tgatctccaa cgtcagccag    1740
ctcccgagcg gttgggcctc catcctttgg tacaacatgc tggtggcgga acccaggaat    1800
ctgtccttct tcctgactcc accatgtgca cgatgggctc agctttcaga agtgctgagt    1860
tggcagtttt cttctgtcac caaaagaggt ctcaatgtgg accagctgaa catgttggga    1920
gagaagcttc ttggtcctaa cgccagcccc gatggtctca ttccgtggac gaggttttgt    1980
aaggaaaata taaatgataa aaattttccc ttctggcttt ggattgaaag catcctagaa    2040
ctcattaaaa aacacctgct ccctctctgg aatgatgggt gcatcatggg cttcatcagc    2100
aaggagcgag agcgtgccct gttgaaggac cagcagccgg ggaccttcct gctgcggttc    2160
agtgagagct cccgggaagg ggccatcaca ttcacatggg tggagcggtc ccagaacgga    2220
ggcgaacctg acttccatgc ggttgaaccc tacacgaaga aagaactttc tgctgttact    2280
ttccctgaca tcattcgcaa ttacaaagtc atggctgctg agaatattcc tgagaatccc    2340
ctgaagtatc tgtatccaaa tattgacaaa gaccatgcct tggaaagta ttactccagg      2400 ccaaaggaag caccagagcc aatgaacttt gatggcccta aggaactgg atatatcaag       2460 actgagttga tttctgtgtc tgaagttcac ccttctagac ttcagaccac agacaacctg    2520
ctccccatgt ctcctgagga gtttgacgag gtgtctcgga gtgtgggctc tgtagaattc    2580
gacagtatga tgaacacagt atagagcatg aattttttc atcttctctg gcgacagttt     2640
tccttctcat ctgtgattcc ctcctgctac tctgttcctt cacatcctgt gtttctaggg    2700 aaaatgaaaga aaggccagca aattcgctgc aacctgttga tagcaagtga atttttctct    2760
aactcagaaa catcagttac tctgaagggc atcatgcatc ttactgaagg taaaattgaa    2820
aggcattctc tgaagagtgg gtttcacaag tgaaaaacat ccagatacac ccaaagtatc    2880
aggacgagaa tgagggtcct ttgggaaagg agaagttaag caacatctag caaatgttat    2940
gcataaagtc agtgcccaac tgttataggt tgttggataa atcagtggtt atttagggaa    3000
ctgcttgacg taggaacggt aaatttctgt gggagaattc ttacatgttt tctttgcttt    3060
aagtgtaact ggcagttttc cattggttta cctgtgaaat agttcaaagc caagtttata    3120
tacaattata tcagtcctct ttcaaaggta gccatcatgg atctggtagg gggaaaatgt    3180
gtattttatt acatctttca cattggctat ttaaagacaa agacaaattc tgtttcttga    3240
gaagagaata ttagctttac tgtttgttat ggcttaatga cactagctaa tatcaataga    3300
aggatgtaca tttccaaatt cacaagttgt gtttgatatc caaagctgaa tacattctgc    3360
tttcatcttg gtcacataca attattttta cagttctccc aagggagtta ggctattcac    3420
aaccactcat tcaaaagttg aaattaacca tagatgtaga taaactcaga aatttaattc    3480
atgtttctta aatgggctac tttgtccttt ttgttattag ggtggtattt agtctattag    3540
ccacaaaatt gggaaggag tagaaaaagc agtaactgac aacttgaata atacaccaga    3600
gataatatga gaatcagatc atttcaaaac tcatttccta tgtaactgca ttgagaactg    3660
```

-continued

| | |
|---|---|
| catatgtttc gctgatatat gtgtttttca catttgcgaa tggttccatt ctctctcctg | 3720 |
| tactttttcc agacactttt ttgagtggat gatgtttcgt gaagtatact gtattttac | 3780 |
| cttttttcctt ccttatcact gacacaaaaa gtagattaag agatgggttt gacaaggttc | 3840 |
| ttcccttttta catactgctg tctatgtggc tgtatcttgt ttttccacta ctgctaccac | 3900 |
| aactatatta tcatgcaaat gctgtattct tctttggtgg agataaagat ttcttgagtt | 3960 |
| ttgttttaaa attaaagcta agtatctgt attgcattaa atataatatg cacacagtgc | 4020 |
| tttccgtggc actgcataca atctgaggcc tcctctctca gttttttatat agatggcgag | 4080 |
| aacctaagtt tcagttgatt ttacaattga atgactaaa aaacaaagaa gacaacatta | 4140 |
| aaacaatatt gtttcta | 4157 |

<210> SEQ ID NO 86
<211> LENGTH: 4451
<212> TYPE: DNA
<213> ORGANISM: Homo sapiens

<400> SEQUENCE: 86

| | |
|---|---|
| gctcatacta gggacgggaa gtcgcgacca gagccattgg agggcgcggg gactgcaacc | 60 |
| ctaatcagca gagcccaaat ggcgcagtgg gaaatgctgc agaatcttga cagccccttt | 120 |
| caggatcagc tgcaccagct ttactcgcac agcctcctgc ctgtggacat tcgacagtac | 180 |
| ttggctgtct ggattgaaga ccagaactgg caggaagctg cacttgggag tgatgattcc | 240 |
| aaggctacca tgctattctt ccacttcttg gatcagctga actatgagtg tggccgttgc | 300 |
| agccaggacc cagagtcctt gttgctgcag cacaatttgc ggaaattctg ccgggacatt | 360 |
| cagccctttt cccaggatcc tacccagttg gctgagatga tctttaacct ccttctggaa | 420 |
| gaaaaaagaa ttttgatcca ggctcagagg gcccaattgg aacaaggaga gccagttctc | 480 |
| gaaacacctg tggagagcca gcaacatgag attgaatccc ggatcctgga tttaagggct | 540 |
| atgatggaga agctggtaaa atccatcagc caactgaaag accagcagga tgtcttctgc | 600 |
| ttccgatata agatccaggc caaagggaag acaccctctc tggaccccca tcagaccaaa | 660 |
| gagcagaaga ttctgcagga aactctcaat gaactggaca aaaggagaaa ggaggtgctg | 720 |
| gatgcctcca agcactgct aggccgatta actaccctaa tcgagctact gctgccaaag | 780 |
| ttggaggagt ggaaggccca gcagcaaaaa gcctgcatca gagctcccat tgaccacggg | 840 |
| ttggaacagc tggagacatg gttcacagct ggagcaaagc tgttgtttca cctgaggcag | 900 |
| ctgctgaagg agctgaaggg actgagttgc ctggttagct atcaggatga ccctctgacc | 960 |
| aaagggtgg acctacgcaa cgcccaggtc acagagttgc tacagcgtct gctccacaga | 1020 |
| gcctttgtgg tagaaaccca gccctgcatg ccccaaactc cccatcgacc cctcatcctc | 1080 |
| aagactggca gcaagttcac cgtccgaaca aggctgctgg tgagactcca ggaaggcaat | 1140 |
| gagtcactga ctgtggaagt ctccattgac aggaatcctc ctcaattaca aggcttccgg | 1200 |
| aagttcaaca ttctgactc aaaccagaaa actttgaccc ccgagaaggg gcagagtcag | 1260 |
| ggtttgattt gggactttgg ttacctgact ctggtggagc aacgttcagg tggttcagga | 1320 |
| aagggcagca ataagggggcc actaggtgtg acagaggaac tgcacatcat cagcttcacg | 1380 |
| gtcaaatata cctaccaggg tctgaagcag gagctgaaaa cggacaccct ccctgtggtg | 1440 |
| attatttcca acatgaacca gctctcaatt gcctgggctt cagttctctg gttcaatttg | 1500 |
| ctcagcccaa accttcagaa ccagcagttc ttctccaacc cccccaaggc ccctggagc | 1560 |
| ttgctgggcc ctgctctcag ttggcagttc tcctcctatg ttggccgagg cctcaactca | 1620 |

-continued

```
gaccagctga gcatgctgag aaacaagctg ttcgggcaga actgtaggac tgaggatcca   1680
ttattgtcct gggctgactt cactaagcga gagagccctc ctggcaagtt accattctgg   1740
acatggctgg acaaaattct ggagttggta catgaccacc tgaaggatct ctggaatgat   1800
ggacgcatca tgggctttgt gagtcggagc caggagcgcc ggctgctgaa gaagaccatg   1860
tctggcacct ttctactgcg cttcagtgaa tcgtcagaag ggggcattac ctgctcctgg   1920
gtggagcacc aggatgatga caaggtgctc atctactctg tgcaaccgta cacgaaggag   1980
gtgctgcagt cactcccgct gactgaaatc atccgccatt accagttgct cactgaggag   2040
aatatacctg aaaacccact gcgcttcctc tatccccgaa tcccccggga tgaagctttt   2100
gggtgctact accaggagaa agttaatctc caggaacgga ggaaatacct gaaacacagg   2160
ctcattgtgg tctctaatag acaggtggat gaactgcaac aaccgctgga gcttaagcca   2220
gagccagagc tggagtcatt agagctgaaa ctagggctgg tgccagagcc agagctcagc   2280
ctggacttag agccactgct gaaggcaggg ctggatctgg ggccagagct agagtctgtg   2340
ctggagtcca ctctggagcc tgtgatagag cccacactat gcatggtatc acaaacagtg   2400
ccagagccag accaaggacc tgtatcacag ccagtgccag agccagattt gccctgtgat   2460
ctgagacatt tgaacactga gccaatggaa atcttcagaa actgtgtaaa gattgaagaa   2520
atcatgccga atggtgaccc actgttggct ggccagaaca ccgtggatga ggtttacgtc   2580
tcccgcccca gccacttcta cactgatgga cccttgatgc cttctgactt ctaggaacca   2640
catttcctct gttcttttca tatctcttgc ccttcctact cctcatagca tgatattgtt   2700
ctccaaggat gggaatcagg catgtgtccc ttccaagctg tgttaactgt tcaaactcag   2760
gcctgtgtga ctccattggg gtgagaggtg aaagcataac atgggtacag aggggacaac   2820
aatgaatcag aacagatgct gagccatagg tctaaatagg atcctggagg ctgcctgctg   2880
tgctgggagg tataggggtc ctgggggcag gccagggcag ttgacaggta cttggagggc   2940
tcagggcagt ggcttctttc cagtatggaa ggatttcaac attttaatag ttggttaggc   3000
taaactggtg catactggca ttggcccttg gtggggagca cagacacagg ataggactcc   3060
atttctttct tccattcctt catgtctagg ataacttgct ttcttctttc ctttactcct   3120
ggctcaagcc ctgaatttct tcttttcctg caggggttga gagctttctg ccttagccta   3180
ccatgtgaaa ctctaccctg aagaaaggga tggataggaa gtagacctct ttttcttacc   3240
agtctcctcc cctactctgc ccctaagctg gctgtacctg ttcctccccc ataaaatgat   3300
cctgccaatc taatgtgagt gtgaagcttt gcacactagt ttatgctacc tagtctccac   3360
tttctcaatg cttaggagac agatcactcc tggaggctgg ggatggtagg attgctgggg   3420
attttttttt ttttaaacag ggtctcactc tgttgcccag gctagagtgc aatggtgcaa   3480
tcacagctca ctgcagcctc aacctcctgg gttcaagcaa tcctcctacc tcagcctcct   3540
gggtagctag caccatggca tgcgccacca tgccctattt tttttttta aagacagggt   3600 cttgctatat tgcccaggct ggtcttgaac tgggctcaag tgatcctcac gccttggcct   3660
cccaaagtgc tgggattata ggcatgagcc actgtgcttg gccaggattt tttttttttt   3720 tttttgaga tggagtttct ctcttgttgt ccaggctgga gtgcaatggt gtgatctcgg   3780
ctcactgcaa cctccgcctt ccgggttcaa gtgactctcc tgcctcagcc tccccagtag   3840
ctgggattac agatctgcac caccatgccc agctaatttt gtattttag tagagacggg   3900 gtttctccat gttggtcagg ctggtctcga actcctgacc tcaagtgatc tgtccacctc   3960
```

```
ggcctcccag agtgctggga ttacaggcgt gagccactgt tcccagcagg aatttctttt    4020
ttatagtatt ggataaagtt tggtgttttt acagaggaga agcaatgggt cttagctctt    4080
tctctattat gttatcatcc tccctttttt gtacaatatg ttgtttacct gaaaggaagg    4140
tttctattcg ttggttgtgg acctggacaa agtccaagtc tgtggaactt aaaaccttga    4200
aggtctgtca taggactctg gacaatctca caccttagct attcccaggg aaccccaggg    4260
ggcaactgac attgctccaa gatgttctcc tgatgtagct tgagatataa aggaaaggcc    4320
ctgcacaggt ggctgtttct tgtctgttat gtcagaggaa cagtcctgtt cagaaagggg    4380
ctcttctgag cagaaatggc taataaactt tgtgctgatc tggaaaaaaa aaaaaaaaaa    4440 aaaaaaaaa a                                                         4451

<210> SEQ ID NO 87
<211> LENGTH: 9
<212> TYPE: PRT
<213> ORGANISM: Homo sapiens

<400> SEQUENCE: 87

Gly Ser Glu Asn Leu Tyr Phe Gln Leu
              5

<210> SEQ ID NO 88
<211> LENGTH: 27
<212> TYPE: DNA
<213> ORGANISM: homo sapiens

<400> SEQUENCE: 88
tctagaggcc tgatcatccg gtctcac                                         27

<210> SEQ ID NO 89
<211> LENGTH: 29
<212> TYPE: DNA
<213> ORGANISM: homo sapiens

<400> SEQUENCE: 89
tctagatgga aaacagaagt cccggaaac                                       29

<210> SEQ ID NO 90
<211> LENGTH: 2290
<212> TYPE: DNA
<213> ORGANISM: Homo sapiens

<400> SEQUENCE: 90
gaattccgaa tcatgtgcag aatgctgaat cttcccccag ccaggacgaa taagacagcg      60
cggaaaagca gattctcgta attctggaat tgcatgttgc aaggagtctc ctggatcttc     120
gcacccagct tcgggtaggg agggagtccg ggtcccgggc taggccagcc cggcaggtgg     180
agagggtccc cggcagcccc gcgcgcccct ggccatgtct ttaatgccct gccccttcat     240
gtggccttct gagggttccc agggctggcc agggttgttt cccacccgcg cgcgcgctct     300
cacccccagc caaacccacc tggcagggct ccctccagcc gagaccttt gattcccggc     360 tcccgcgctc ccgcctccgc gccagcccgg gaggtggccc tggacagccg gacctcgccc     420
ggccccggct gggaccatgg tgtttctctc gggaaatgct tccgacagct ccaactgcac     480
ccaaccgccg gcaccggtga acatttccaa ggccattctg tcgggtgtga tcttgggggg     540
cctcattctt ttcggggtgc tgggtaacat cctagtgatc ctctcgtag cctgtcaccg     600 acaccttcac tcagtcacgc actactacat cgtcaacctg gcggtggccg acctcctgct     660
```

-continued

```
cacctccacg gtgctgccct tctccgccat cttcgaggtc ctaggctact gggccttcgg      720 caggqtcttc tgcaacatct gggcggcagt ggatgtgctg tgctgcaccg cgtccatcat      780
gggcctctgc atcatctcca tcgaccgcta catcggcgtg agctaccgc tgcgctaccc       840 aaccatcgtc acccagagga ggggtctcat ggctctgctc tgcgtctggg cactctccct     900
ggtcatatcc attggacccc tgttcggctg gaggcagccg gccccgagg acgagaccat      960 ctgccagatc aacgaggagc cggctacgt gctcttctca gcgctgggct ccttctacct     1020
gcctctggcc atcatcctgg tcatgtactg ccgcgtctac gtggtggcca agagggagag     1080
ccggggcctc aagtctggcc tcaagaccga caagtcggac tcggagcaag tgacgctccg    1140
catccatcgg aaaaacgccc cggcaggagg cagcgggatg ccagcgcca agaccaagac     1200 gcacttctca gtgaggctcc tcaagttctc ccgggagaag aaagcggcca aaacgctggg    1260
catcgtggtc ggctgcttcg tcctctgctg gctgcctttt tcttagtca tgcccattgg     1320 gtctttcttc cctgatttca agccctctga acagttttt aaaatagtat tttggctcgg     1380
atatctaaac agctgcatca accccatcat atacccatgc tccagccaag agttcaaaaa    1440
ggcctttcag aatgtcttga gaatccagtg tctccgcaga aagcagtctt ccaaacatgc    1500
cctgggctac accctgcacc cgcccagcca ggccgtggaa gggcaacaca aggacatggt    1560
gcgcatcccc gtgggatcaa gagagacctt ctacaggatc tccaagacgg atggcgtttg    1620
tgaatggaaa ttttctctt ccatgccccg tggatctgcc aggattacag tgtccaaaga    1680
ccaatcctcc tgtaccacag cccgggtgag aagtaaaagc ttttggagg tctgctgctg    1740 tgtagggccc tcaacccca gccttgacaa gaaccatcaa gttccaacca ttaaggtcca    1800
caccatctcc ctcagtgaga acggggagga agtctaggac aggaaagatg cagaggaaag   1860
gggaataatc ttaggtaccc accccacttc cttctcggaa ggccagctct tcttggagga    1920
caagacagga ccaatcaaag aggggacctg ctgggaatgg ggtgggtggt agacccaact    1980
catcaggcag cgggtagggc acagggaaga gggagggtgt ctcacaacca accagttcag    2040
aatgatacgg aacagcattt ccctgcagct aatgctttct tggtcactct gtgcccactt    2100
caacgaaaac caccatggga aacagaattt catgcacaat ccaaaagact ataaatatag    2160
gattatgatt tcatcatgaa tattttgagc acacactcta agtttggagc tatttcttga    2220
tggaagtgag gggattttat tttcaggctc aacctactga cagccacatt tgacatttat    2280
gccggaattc                                                           2290
```

<210> SEQ ID NO 91
<211> LENGTH: 26
<212> TYPE: DNA
<213> ORGANISM: homo sapiens

<400> SEQUENCE: 91

```
ctcggatatc taaacagctg catcaa                                          26
```

<210> SEQ ID NO 92
<211> LENGTH: 29
<212> TYPE: DNA
<213> ORGANISM: homo sapiens

<400> SEQUENCE: 92

```
tctagacttt ctgcagagac actggattc                                       29
```

<210> SEQ ID NO 93
<211> LENGTH: 31

```
<212> TYPE: DNA
<213> ORGANISM: homo sapiens

<400> SEQUENCE: 93
tctagatcga aggcagtgga ggatcttcag g                                  31

<210> SEQ ID NO 94
<211> LENGTH: 27
<212> TYPE: DNA
<213> ORGANISM: homo sapiens

<400> SEQUENCE: 94
tctagaggcc tgatcatccg gtctcac                                       27

<210> SEQ ID NO 95
<211> LENGTH: 23
<212> TYPE: DNA
<213> ORGANISM: homo sapiens

<400> SEQUENCE: 95
cggatccgtt ggtactcttg agg                                           23

<210> SEQ ID NO 96
<211> LENGTH: 4989
<212> TYPE: DNA
<213> ORGANISM: homo sapiens

<400> SEQUENCE: 96
tttttttttt ttttgagaaa gggaatttca tcccaaataa aaggaatgaa gtctggctcc    60
ggaggagggt ccccgacctc gctgtggggg ctcctgtttc tctccgccgc gctctcgctc   120
tggccgacga gtggagaaat ctgcgggcca ggcatcgaca tccgcaacga ctatcagcag   180
ctgaagcgcc tggagaactg cacggtgatc gagggctacc tccacatcct gctcatctcc   240
aaggccgagg actaccgcag ctaccgcttc cccaagctca cggtcattac cgagtacttg   300
ctgctgttcc gagtggctgg cctcgagagc tcggagacct cttccccaa cctcacggtc   360 atccgcggct ggaaactctt ctacaactac gccctggtca tcttcgagat gaccaatctc   420
aaggatattg gctttacaa cctgaggaac attactcggg gggccatcag gattgagaaa   480
aatgctgacc tctgttacct ctccactgtg gactggtccc tgatcctgga tgcggtgtcc   540
aataactaca ttgtggggaa taagccccca aaggaatgtg gggacctgtg tccagggacc   600
atggaggaga agccgatgtg tgagaagacc accatcaaca tgagtacaa ctaccgctgc   660 tggaccacaa accgctgcca gaaaatgtgc ccaagcacgt gtgggaagcg ggcgtgcacc   720
gagaacaatg agtgctgcca ccccgagtgc ctgggcagct gcagcgcgcc tgacaacgac   780
acggcctgtg tagcttgccg ccactactac tatgccggtg tctgtgtgcc tgcctgcccg   840
cccaacacct acaggtttga gggctggcgc tgtgtggacc gtgacttctg cgccaacatc   900
ctcagcgccg agagcagcga ctccgagggg tttgtgatcc acgacggcga gtgcatgcag   960
gagtgcccct cgggcttcat ccgcaacggc agccagagca tgtactgcat cccttgtgaa  1020
ggtccttgcc cgaaggtctg tgaggaagaa agaaaacaa agaccattga ttctgttact  1080
tctgctcaga tgctccaagg atgcaccatc ttcaagggca tttgctcat taacatccga  1140 cgggggaata acattgcttc agagctggag aacttcatgg ggctcatcga ggtggtgacg  1200
ggctacgtga agatccgcca ttctcatgcc ttggtctcct tgtccttcct aaaaaacctt  1260
cgcctcatcc taggagagga gcagctagaa gggaattact ccttctacgt cctcgacaac  1320
```

```
cagaacttgc agcaactgtg ggactgggac caccgcaacc tgaccatcaa agcagggaaa    1380
atgtactttg ctttcaatcc caaattatgt gtttccgaaa tttaccgcat ggaggaagtg    1440
acggggacta aagggcgcca aagcaaaggg gacataaaca ccaggaacaa cggggagaga    1500
gcctcctgtg aaagtgacgt cctgcatttc acctccacca ccacgtcgaa gaatcgcatc    1560
atcataacct ggcaccggta ccggccccct gactacaggg atctcatcag cttcaccgtt    1620
tactacaagg aagcacccct taagaatgtc acagagtatg atgggcagga tgcctgcggc    1680
tccaacagct ggaacatggt ggacgtggac ctcccgccca acaaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctccctct ctgcccaacg gcaacctgag ttactacatt    1980
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga aaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga gacagagtac ccttcttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct tttaaagtg gccggaacct gagaatccca atggattgat tctaatgtat    2640
gaaataaaat acggatcaca agttgaggat cagcgagaat gtgtgtccag acaggaatac    2700
aggaagtatg gagggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
gtgtacgttc ctgatgagtg ggaggtggct cgggagaaga tcaccatgag ccggaacctt    3060
gggcaggggt cgtttgggat ggtctatgaa ggagttgcca agggtgtggt gaaagatgaa    3120
cctgaaacca gagtggccat taaaacagtg aacgaggccg caagcatgcg tgagaggatt    3180
gagtttctca acgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga cagagactat    3540
taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccagggc ttgtccaacg agcaagtcct tcgcttcgtc    3720
```

-continued

| | | | |
|---|---|---|---|
| atggagggcg | gccttctgga | caagccagac | aactgtcctg acatgctgtt tgaactgatg | 3780 |
| cgcatgtgct | ggcagtataa | ccccaagatg | aggccttcct tcctggagat catcagcagc | 3840 |
| atcaaagagg | agatggagcc | tggcttccgg | gaggtctcct tctactacag cgaggagaac | 3900 |
| aagctgcccg | agccggagga | gctggacctg | agccagaga acatggagag cgtccccctg | 3960 |
| gaccctcgg | cctcctcgtc | ctccctgcca | ctgcccgaca cactcagg acacaaggcc | 4020 |
| gagaacggcc | ccggccctgg | ggtgctggtc | ctccgcgcca gcttcgacga gagacagcct | 4080 |
| tacgcccaca | tgaacggggg | ccgcaagaac | gagcgggcct gccgctgcc ccagtcttcg | 4140 |
| acctgctgat | ccttggatcc | tgaatctgtg | caaacagtaa cgtgtgcgca cgcgcagcgg | 4200 |
| ggtgggggg | gagagagagt | tttaacaatc | cattcacaag cctcctgtac ctcagtggat | 4260 |
| cttcagttct | gcccttgctg | cccgcgggag | acagcttctc tgcagtaaaa cacatttggg | 4320 |
| atgttccttt | tttcaatatg | caagcagctt | tttattccct gcccaaaccc ttaactgaca | 4380 |
| tgggccttta | agaaccttaa | tgacaacact | taatagcaac agagcacttg agaaccagtc | 4440 |
| tcctcactct | gtccctgtcc | ttccctgttc | tccctttctc tctcctctct gcttcataac | 4500 |
| ggaaaaataa | ttgccacaag | tccagctggg | aagcccttt tatcagtttg aggaagtggc | 4560 |
| tgtccctgtg | gccccatcca | accactgtac | acacccgcct gacaccgtgg gtcattacaa | 4620 |
| aaaaacacgt | ggagatggaa | attttttacct | ttatctttca cctttctagg gacatgaaat | 4680 |
| ttacaaaggg | ccatcgttca | tccaaggctg | ttaccatttt aacgctgcct aattttgcca | 4740 |
| aaatcctgaa | ctttctccct | catcggcccg | gcgctgattc tcgtgtccg gaggcatggg | 4800 |
| tgagcatggc | agctggttgc | tccatttgag | agacacgctg gcgacacact ccgtccatcc | 4860 |
| gactgcccct | gctgtgctgc | tcaaggccac | aggcacacag gtctcattgc ttctgactag | 4920 |
| attattattt | gggggaactg | gacacaatag | gtctttctct cagtgaaggt ggggagaagc | 4980 |
| tgaaccggc | | | | 4989 |

<210> SEQ ID NO 97
<211> LENGTH: 3076
<212> TYPE: DNA
<213> ORGANISM: homo sapiens

<400> SEQUENCE: 97

| | | | |
|---|---|---|---|
| gtttctccag | ggaggcaggg | cccggggaga | aagttggagc ggtaacctaa gctggcagtg | 60 |
| gcgtgatccg | gcaccaaatc | ggcccgcggt | gcggtgcgga gactccatga ggccctggac | 120 |
| atgaacaagc | tgagtggagg | cggcgggcgc | aggactcggg tggaagggg ccagcttggg | 180 |
| ggcgaggagt | ggacccgcca | cgggagcttt | gtcaataagc ccacgcgggg ctggctgcat | 240 |
| cccaacgaca | aagtcatggg | acccggggtt | tcctacttgg ttcggtacat gggttgtgtg | 300 |
| gaggtcctcc | agtcaatgcg | tgccctggac | ttcaacaccc ggactcaggt caccagggag | 360 |
| gccatcagtc | tggtgtgtga | ggctgtgccg | ggtgctaagg gggcgacaag gaggagaaag | 420 |
| ccctgtagcc | gcccgctcag | ctctatcctg | ggaggagta acctgaaatt tgctggaatg | 480 |
| ccaatcactc | tcaccgtctc | caccagcagc | ctcaacctca tggccgcaga ctgcaaacag | 540 |
| atcatcgcca | accaccacat | gcaatctatc | tcatttgcat ccggcgggga tccggacaca | 600 |
| gccgagtatg | tcgcctatgt | tgccaaagac | cctgtgaatc agagagcctg ccacattctg | 660 |
| gagtgtcccg | aagggcttgc | ccaggatgtc | atcagcacca ttggccaggc cttcgagttg | 720 |
| cgcttcaaac | aatacctcag | gaacccaccc | aaactggtca cccctcatga caggatggct | 780 |

-continued

```
ggctttgatg gctcagcatg ggatgaggag gaggaagagc cacctgacca tcagtactat    840
aatgacttcc cggggaagga accccccttg ggggggtgg tagacatgag gcttcgggaa    900
ggagccgctc caggggctgc tcgacccact gcacccaatg cccagacccc cagccacttg    960
ggagctacat tgcctgtagg acagcctgtt ggggagatc cagaagtccg caaacagatg   1020
ccacctccac caccctgtcc agcaggcaga gagctttttg atgatccctc ctatgtcaac   1080
gtccagaacc tagacaaggc ccggcaagca gtgggtggtg ctgggccccc caatcctgct   1140
atcaatggca gtgcaccccg ggacctgttt gacatgaagc ccttcgaaga tgctcttcgc   1200
gtgcctccac ctccccagtc ggtgtccatg gctgagcagc tccaggggga gccctggttc   1260
catgggaagc tgagccggcg ggaggctgag gcactgctgc agctcaatgg ggacttcctg   1320
gtacgggaga gcacgaccac acctggccag tatgtgctca ctggcttgca gagtgggcag   1380
cctaagcatt tgctactggt ggaccctgag ggtgtggttc ggactaagga tcaccgcttt   1440
gaaagtgtca gtcaccttat cagctaccac atggacaatc acttgcccat catctctgcg   1500
ggcagcgaac tgtgtctaca gcaacctgtg gagcggaaac tgtgatctgc cctagcgctc   1560
tcttccagaa gatgccctcc aatcctttcc accctattcc ctaactctcg ggacctcgtt   1620
tgggagtgtt ctgtgggctt ggccttgtgt cagagctggg agtagcatgg actctgggtt   1680
tcatatccag ctgagtgaga gggtttgagt caaaagcctg ggtgagaatc ctgcctctcc   1740
ccaaacatta atcaccaaag tattaatgta cagagtggcc cctcacctgg gcctttcctg   1800
tgccaacctg atgccccttc cccaagaagg tgagtgcttg tcatgaaaa tgtcctgtgg   1860
tgacaggccc agtggaacag tcaccttct gggcaagggg gaacaaatca cacctctggg   1920
cttcagggta tcccagaccc ctctcaacac ccgccccccc catgtttaaa ctttgtgcct   1980
ttgaccatct cttaggtcta atgatatttt atgcaaacag ttcttggacc cctgaattca   2040
atgacaggga tgccaacacc ttcttggctt ctgggacctg tgttcttgct gagcaccctc   2100
tccggtttgg gttgggataa cagaggcagg agtggcagct gtccctctc cctggggata   2160
tgcaacccttt agagattgcc ccagagcccc actcccggcc aggcgggaga tggacccctc   2220
ccttgctcag tgcctcctgg ccggggcccc tcaccccaag gggtctgtat atacatttca   2280
taaggcctgc cctcccatgt tgcatgccta tgtactctac gccaaagtgc agcccttcct   2340
cctgaagcct ctgccctgcc tcccttctg ggagggcggg gtgggggtga ctgaatttgg   2400
gcctcttgta cagttaactc tcccaggtgg atttttgtgga ggtgagaaaa ggggcattga   2460
gactataaag cagtagacaa tccccacata ccatctgtag agttggaact gcattctttt   2520
aaagttttat atgcatatat tttagggctg tagacttact ttcctatttt cttttccatt   2580
gcttattctt gagcacaaaa tgataatcaa ttattacatt tatacatcac cttttttgact   2640
tttccaagcc cttttacagc tcttggcatt ttcctcgcct aggcctgtga ggtaactggg   2700
atcgcacctt ttataccaga gacctgaggc agatgaaatt tatttccatc taggactaga   2760
aaaacttggg tctcttaccg cgagactgag aggcagaagt cagcccgaat gcctgtcagt   2820
ttcatggagg ggaaacgcaa aacctgcagt tcctgagtac cttctacagg cccggcccag   2880
cctaggcccg gggtggccac accacagcaa gccggccccc cctcttttgg ccttgtggat   2940
aagggagagt tgaccgtttt catcctggcc tccttttgct gtttggatgt ttccacgggt   3000
ctcacttata ccaaagggaa aactcttcat taaagtccgt atttcttcta aaaaaaaaa   3060
aaaaaaaaaa aaaaaa                                                     3076
```

<210> SEQ ID NO 98
<211> LENGTH: 4
<212> TYPE: PRT
<213> ORGANISM: homo sapiens

<400> SEQUENCE: 98

Asn Ser Gly Ser
1

<210> SEQ ID NO 99
<211> LENGTH: 2261
<212> TYPE: DNA
<213> ORGANISM: homo sapiens

<400> SEQUENCE: 99

| | | | | | |
|---|---|---|---|---|---|
| gaaatcaggc | tccgggccgg | ccgaagggcg | caactttccc | ccctcggcgc | cccaccggct | 60 |
| cccgcgcgcc | tccccthcgcg | cccgagcttc | gagccaagca | gcgtcctggg | gagcgcgtca | 120 |
| tggccttacc | agtgaccgcc | ttgctcctgc | cgctggcctt | gctgctccac | gccgccaggc | 180 |
| cgagccagtt | ccgggtgtcg | ccgctggatc | ggacctggaa | cctgggcgag | acagtggagc | 240 |
| tgaagtgcca | ggtgctgctg | tccaacccga | cgtcgggctg | ctcgtggctc | ttccagccgc | 300 |
| gcggcgccgc | cgccagtccc | accttcctcc | tatacctctc | ccaaaacaag | cccaaggcgg | 360 |
| ccgaggggct | ggacacccag | cggttctcgg | gcaagaggtt | gggggacacc | ttcgtcctca | 420 |
| ccctgagcga | cttccgccga | gagaacgagg | gctactattt | ctgctcggcc | ctgagcaact | 480 |
| ccatcatgta | cttcagccac | ttcgtgccgg | tcttcctgcc | agcgaagccc | accacgacgc | 540 |
| cagcgccgcg | accaccaaca | ccggcgccca | ccatcgcgtc | gcagcccctg | tccctgcgcc | 600 |
| cagaggcgtg | ccggccagcg | gcggggggcg | cagtgcacac | gaggggggctg | gacttcgcct | 660 |
| gtgatatcta | catctgggcg | cccttggccg | ggacttgtgg | ggtccttctc | ctgtcactgg | 720 |
| ttatcacccta | ttactgcaac | cacaggaacc | gaagacgtgt | ttgcaaatgt | ccccggcctg | 780 |
| tggtcaaatc | gggagacaag | cccagccttt | cggcgagata | cgtctaaccc | tgtgcaacag | 840 |
| ccactacatt | acttcaaact | gagatccttc | cttttgaggg | agcaagtcct | tcccttcat | 900 |
| tttttccagt | cttcctccct | gtgtattcat | tctcatgatt | attattttag | tggggcggg | 960 |
| gtgggaaaga | ttacttttc | tttatgtgtt | tgacggaaa | caaaactagg | taaaatctac | 1020 |
| agtacaccac | aagggtcaca | atactgttgt | gcgcacatcg | cggtagggcg | tggaaagggg | 1080 |
| caggccagag | ctacccgcag | agttctcaga | atcatgctga | gagagctgga | ggcacccatg | 1140 |
| ccatctcaac | ctcttccccg | cccgttttac | aaaggggggag | gctaaagccc | agagacagct | 1200 |
| tgatcaaagg | cacacagcaa | gtcagggttg | gagcagtagc | tggagggacc | ttgtctccca | 1260 |
| gctcagggct | ctttcctcca | caccattcag | gtctttcttt | ccgaggcccc | tgtctcaggg | 1320 |
| tgaggtgctt | gagtctccaa | cggcaaggga | acaagtactt | cttgatacct | gggatactgt | 1380 |
| gcccagagcc | tcgaggaggt | aatgaattaa | agaagagaac | tgcctttggc | agagttctat | 1440 |
| aatgtaaaca | atatcagact | ttttttttt | ataatcaagc | ctaaaattgt | atagacctaa | 1500 |
| aataaaatga | agtggtgagc | ttaaccctgg | aaaatgaatc | cctctatctc | taagaaaat | 1560 |
| ctctgtgaaa | ccctatgtg | gagcggaat | tgctctccca | gcccttgcat | gcagagggg | 1620 |
| cccatgaaaa | aggacaggct | acccctttac | aaatagaatt | tgagcatcag | tgaggttaaa | 1680 |
| ctaaggccct | cttgaatctc | tgaatttgag | atacaaacat | gttcctggga | tcactgatga | 1740 |
| cttttttatac | tttgtaaaga | caattgttgg | agagcccctc | acacagccct | ggcctctgct | 1800 |
| caactagcag | atacagggat | gaggcagacc | tgactctctt | aaggaggctg | agagcccaaa | 1860 |

-continued

```
ctgctgtccc aaacatgcac ttccttgctt aaggtatggt acaagcaatg cctgcccatt      1920
ggagagaaaa aacttaagta gataaggaaa taagaaccac tcataattct tcaccttagg      1980
aataatctcc tgttaatatg gtgtacattc ttcctgatta ttttctacac atacatgtaa      2040
aatatgtctt tctttttaa atagggttgt actatgctgt tatgagtggc tttaatgaat       2100
aaacatttgt agcatcctct ttaatgggta acagcaaaa aaaaaaaaa aaaaaaaaa         2160 aaaaaaaaaa aaaaaaaaaa aaaaaaaaaa aaaaaaaaaa aaaaaaaaaa aaaaaaaaaa      2220
aaaaaaaaaa aaaaaaaaaa aaaaaaaaaa aaaaaaaaaa a                          2261

<210> SEQ ID NO 100
<211> LENGTH: 6450
<212> TYPE: DNA
<213> ORGANISM: homo sapiens

<400> SEQUENCE: 100
gagttgtgcc tggagtgatg tttaagccaa tgtcagggca aggcaacagt ccctggccgt        60
cctccagcac ctttgtaatg catatgagct cgggagacca gtacttaaag ttggaggccc       120
gggagcccag gagctggcgg agggcgttcg tcctgggagc tgcacttgct ccgtcgggtc       180
gccggcttca ccggaccgca ggctcccggg gcagggccgg ggccagagct cgcgtgtcgg       240
cgggacatgc gctgcgtcgc ctctaacctc gggctgtgct ctttttccag gtggcccgcc       300
ggtttctgag ccttctgccc tgcggggaca cggtctgcac cctgcccgcg gccacggacc       360
atgaccatga ccctccacac caaagcatct gggatgcccc tactgcatca gatccaaggg       420
aacgagctgg agccccctgaa ccgtccgcag ctcaagatcc ccctggagcg gccccctgggc      480 gaggtgtacc tggacagcag caagcccgcc gtgtacaact accccgaggg cgccgcctac       540
gagttcaacg ccgcggccgc cgccaacgcg caggtctacg gtcagaccgg cctcccctac       600
ggcccccggt ctgaggctgc ggcgttcggc tccaacggcc tgggggtttt ccccccactc       660
aacagcgtgt ctccgagccc gctgatgcta ctgcacccgc cgccgcagct gtcgcctttc       720
ctgcagcccc acgccagca ggtgccctac tacctggaga cgagcccag cggctacacg         780 gtgcgcgagg ccggcccgcc ggcattctac aggccaaatt cagataatcg acgccagggt      840
ggcagagaaa gattggccag taccaatgac aaggaagta tggctatgga atctgccaag       900
gagactcgct actgtgcagt gtgcaatgac tatgcttcag gctaccatta tggagtctgg      960
tcctgtgagg gctgcaaggc cttcttcaag agaagtattc aaggacataa cgactatatg     1020
tgtccagcca ccaaccagtg caccattgat aaaaacagga ggaagagctg ccaggcctgc     1080
cggctccgca aatgctacga agtgggaatg atgaaaggtg ggatacgaaa agaccgaaga     1140
ggagggagaa tgttgaaaca caagcgccag agagatgatg gggagggcag gggtgaagtg    1200
gggtctgctg gagacatgag agctgccaac ctttggccaa gcccgctcat gatcaaacgc     1260
tctaagaaga acagcctggc cttgtccctg acggccgacc agatggtcag tgccttgttg     1320
gatgctgagc cccccatact ctattccgag tatgatccta ccagacccct cagtgaagct     1380
tcgatgatgg gcttactgac caacctggca gacagggagc tggttcacat gatcaactgg     1440
gcgaagaggg tgccaggctt tgtggatttg accctccatg atcaggtcca ccttctagaa     1500
tgtgcctggc tagagatcct gatgattggt ctcgtctggc gctccatgga gcacccagtg    1560
aagctactgt tgctcctaa cttgctcttg gacaggaacc aggaaaatg tgtagagggc       1620 atggtggaga tcttcgacat gctgctggct acatcatctc ggttccgcat gatgaatctg     1680
```

```
cagggagagg agtttgtgtg cctcaaatct attattttgc ttaattctgg agtgtacaca    1740
tttctgtcca gcaccctgaa gtctctggaa gagaaggacc atatccaccg agtcctggac    1800
aagatcacag acactttgat ccacctgatg gccaaggcag gcctgaccct gcagcagcag    1860
caccagcggc tggcccagct cctcctcatc ctctcccaca tcaggcacat gagtaacaaa    1920
ggcatggagc atctgtacag catgaagtgc aagaacgtgg tgcccctcta tgacctgctg    1980
ctggagatgc tggacgccca ccgcctacat gcgcccacta gccgtggagg ggcatccgtg    2040
gaggagacgg accaaagcca cttggccact gcgggctcta cttcatcgca ttccttgcaa    2100
aagtattaca tcacggggga ggcagagggt ttccctgcca cagtctgaga gctccctggc    2160
tcccacacgg ttcagataat ccctgctgca ttttaccctc atcatgcacc actttagcca    2220
aattctgtct cctgcataca ctccggcatg catccaacac caatggcttt ctagatgagt    2280
ggccattcat ttgcttgctc agttcttagt ggcacatctt ctgtcttctg ttgggaacag    2340
ccaaagggat tccaaggcta aatctttgta acagctctct ttccccttg ctatgttact    2400 aagcgtgagg attcccgtag ctcttcacag ctgaactcag tctatgggtt ggggctcaga    2460
taactctgtg catttaagct acttgtagag acccaggcct ggagagtaga cattttgcct    2520
ctgataagca cttttaaat ggctctaaga ataagccaca gcaaagaatt taaagtggct    2580
cctttaattg gtgacttgga gaaagctagg tcaagggttt attatagcac cctcttgtat    2640
tcctatggca atgcatcctt ttatgaaagt ggtacacctt aaagctttta tatgactgta    2700
gcagagtatc tggtgattgt caattcactt cccctatag aatacaagg ggccacacag    2760 ggaaggcaga tcccctagtt ggccaagact tattttaact tgatacactg cagattcaga    2820
gtgtcctgaa gctctgcctc tggctttccg gtcatgggtt ccagttaatt catgcctccc    2880
atggacctat ggagagcaac aagttgatct tagttaagtc tccctatatg agggataagt    2940
tcctgatttt tgtttttatt tttgtgttac aaaagaaagc cctccctccc tgaacttgca    3000
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg gggtagtcca    3360
gctcttattc atttcccagc gtggccctgg ttggaagaag cagctgtcaa gttgtagaca    3420
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct ccccttcct ccccgccc    3600 gttccctacc gcctccactc ctgccagctc atttccttca atttcctttg acctataggc    3660 taaaaagaa aggctcattc cagccacagg gcagccttcc ctgggccttt gcttctctag    3720
cacaattatg ggttacttcc ttttcttaa caaaaagaa tgtttgattt cctctgggtg    3780
accttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960 aaaaagtttt tatgtgcact taaatttggg gacaatttta tgtatctgtg ttaaggatat    4020
gcttaagaac ataattcttt tgttgctgtt tgtttaagaa gcaccttagt ttgtttaaga    4080
```

-continued

```
agcacttat  atagtataat  atatatttt   ttgaaattac  attgcttgtt  tatcagacaa   4140
ttgaatgtag  taattctgtt  ctggatttaa  tttgactggg  ttaacatgca  aaaaccaagg   4200
aaaaatattt  agttttttt   tttttttttg  tatactttc   aagctacctt  gtcatgtata   4260
cagtcattta  tgcctaaagc  ctggtgatta  ttcatttaaa  tgaagatcac  atttcatatc   4320
aacttttgta  tccacagtag  acaaaatagc  actaatccag  atgcctattg  ttggatattg   4380
aatgacagac  aatcttatgt  agcaaagatt  atgcctgaaa  aggaaaatta  ttcagggcag   4440
ctaattttgc  ttttaccaaa  atatcagtag  taatatttt   ggacagtagc  taatgggtca   4500
gtgggttctt  tttaatgttt  atacttagat  tttcttttaa  aaaaattaaa  ataaaacaaa   4560
aaaaatttct  aggactagac  gatgtaatac  cagctaaagc  caaacaatta  tacagtggaa   4620
ggttttacat  tattcatcca  atgtgtttct  attcatgtta  agatactact  acatttgaag   4680
tgggcagaga  acatcagatg  attgaaatgt  tcgcccaggg  gtctccagca  actttggaaa   4740
tctctttgta  ttttacttg   aagtgccact  aatggacagc  agatatttc   tggctgatgt   4800
tggtattggg  tgtaggaaca  tgatttaaaa  aaaaaactct  tgcctctgct  ttccccccact  4860
ctgaggcaag  ttaaaatgta  aaagatgtga  tttatctggg  gggctcaggt  atggtgggga   4920
agtggattca  ggaatctggg  gaatggcaaa  tatattaaga  agagtattga  aagtatttgg   4980
aggaaaatgg  ttaattctgg  gtgtgcacca  aggttcagta  gagtccactt  ctgccctgga   5040
gaccacaaat  caactagctc  catttacagc  catttctaaa  atggcagctt  cagttctaga   5100
gaagaaagaa  caacatcagc  agtaaagtcc  atggaatagc  tagtggtctg  tgtttcttt   5160
cgccattgcc  tagcttgccg  taatgattct  ataatgccat  catgcagcaa  ttatgagagg   5220
ctaggtcatc  caaagagaag  acctatcaa   tgtaggttgc  aaaatctaac  ccctaaggaa   5280
gtgcagtctt  tgatttgatt  tccctagtaa  ccttgcagat  atgtttaacc  aagccatagc   5340
ccatgccttt  tgagggctga  acaaataagg  gacttactga  taatttactt  ttgatcacat   5400
taaggtgttc  tcaccttgaa  atcttataca  ctgaaatggc  cattgattta  ggccactggc   5460
ttagagtact  ccttcccctg  catgacactg  attacaaata  cttcctatt   catactttcc   5520
aattatgaga  tggactgtgg  gtactgggag  tgatcactaa  caccatagta  atgtctaata   5580
ttcacaggca  gatctgcttg  gggaagctag  ttatgtgaaa  ggcaaataaa  gtcatacagt   5640
agctcaaaag  gcaaccataa  ttctctttgg  tgcaagtctt  gggagcgtga  tctagattac   5700
actgcaccat  tcccaagtta  atccctgaa   aacttactct  caactggagc  aaatgaactt   5760
tggtcccaaa  tatccatctt  ttcagtagcg  ttaattatgc  tctgtttcca  actgcatttc   5820
ctttccaatt  gaattaaagt  gtggcctcgt  ttttagtcat  ttaaaattgt  tttctaagta   5880
attgctgcct  ctattatggc  acttcaattt  tgcactgtct  tttgagattc  aagaaaaatt   5940
tctattcatt  ttttttgcatc  caattgtgcc  tgaacttta   aaatatgtaa  atgctgccat   6000
gttccaaacc  catcgtcagt  gtgtgtgttt  agagctgtgc  accctagaaa  caacatactt   6060
gtcccatgag  caggtgcctg  agacacagac  ccctttgcat  tcacagagag  gtcattggtt   6120
atagagactt  gaattaataa  gtgacattat  gccagtttct  gttctctcac  aggtgataaa   6180
caatgctttt  tgtgcactac  atactcttca  gtgtagagct  cttgttttat  gggaaaaggc   6240
tcaaatgcca  aattgtgttt  gatggattaa  tatgcccttt  tgccgatgca  tactattact   6300
gatgtgactc  ggttttgtcg  cagctttgct  ttgtttaatg  aaacacactt  gtaaacctct   6360
tttgcacttt  gaaaaagaat  ccagcgggat  gctcgagcac  ctgtaaacaa  ttttctcaac   6420
```

-continued

| ctatttgatg ttcaaataaa gaattaaact | 6450 |

<210> SEQ ID NO 101
<211> LENGTH: 2011
<212> TYPE: DNA
<213> ORGANISM: homo sapiens

<400> SEQUENCE: 101

| tttcagtttc tccagctgct ggcttttgg acacccactc ccccgccagg aggcagttgc | 60 |
| aagcgcggag gctgcgagaa ataactgcct cttgaaactt gcagggcgaa gagcaggcgg | 120 |
| cgagcgctgg gccggggagg gaccacccga gctgcgacgg gctctggggc tgcggggcag | 180 |
| ggctggcgcc cggagcctga gctgcaggag gtgcgctcgc tttcctcaac aggtggcggc | 240 |
| ggggcgcgcg ccgggagacc cccctaatg cgggaaaagc acgtgtccgc attttagaga | 300 |
| aggcaaggcc ggtgtgttta tctgcaagcc attatacttg cccacgaatc tttgagaaca | 360 |
| ttataatgac ctttgtgcct cttcttgcaa ggtgttttct cagctgttat ctcaagacat | 420 |
| ggatataaaa aactcaccat ctagccttaa ttctccttcc tcctacaact gcagtcaatc | 480 |
| catcttaccc ctggagcacg gctccatata cataccttcc tcctatgtag acagccacca | 540 |
| tgaatatcca gccatgacat tctatagccc tgctgtgatg aattacagca ttcccagcaa | 600 |
| tgtcactaac ttggaaggtg ggcctggtcg gcagaccaca agcccaaatg tgttgtggcc | 660 |
| aacacctggg caccttcctc ctttagtggt ccatcgccag ttatcacatc tgtatgcgga | 720 |
| acctcaaaag agtccctggt gtgaagcaag atcgctagaa cacaccttac ctgtaaacag | 780 |
| agagacactg aaaaggaagg ttagtgggaa ccgttgcgcc agccctgtta ctggtccagg | 840 |
| ttcaaagagg gatgctcact tctgcgctgt ctgcagcgat tacgcatcgg gatatcacta | 900 |
| tggagtctgg tcgtgtgaag gatgtaaggc ctttttttaa agaagcattc aaggacataa | 960 |
| tgattatatt tgtccagcta caaatcagtg tacaatcgat aaaaaccggc gcaagagctg | 1020 |
| ccaggcctgc cgacttcgga agtgttacga agtgggaatg gtgaagtgtg gctcccggag | 1080 |
| agagagatgt gggtaccgcc ttgtgcggag acagagaagt gccgacgagc agctgcactg | 1140 |
| tgccggcaag gccaagagaa gtggcggcca cgcgccccga gtgcgggagc tgctgctgga | 1200 |
| cgccctgagc cccgagcagc tagtgctcac cctcctggag gctgagccgc cccatgtgct | 1260 |
| gatcagccgc cccagtgcgc ccttcaccga ggcctccatg atgatgtccc tgaccaagtt | 1320 |
| ggccgacaag gagttggtac acatgatcag ctgggccaag aagattcccg gctttgtgga | 1380 |
| gctcagcctg ttcgaccaag tgcggctctt ggagagctgt tggatggagg tgttaatgat | 1440 |
| ggggctgatg tggcgctcaa ttgaccaccc cggcaagctc atctttgctc cagatcttgt | 1500 |
| tctggacagg gatgagggga aatgcgtaga aggaattctg gaaatctttg acatgctcct | 1560 |
| ggcaactact tcaaggtttc gagagttaaa actccaacac aaagaatatc tctgtgtcaa | 1620 |
| ggccatgatc ctgctcaatt ccagtatgta ccctctggtc acagcgaccc aggatgctga | 1680 |
| cagcagccgg aagctggctc acttgctgaa cgccgtgacc gatgctttgg tttgggtgat | 1740 |
| tgccaagagc ggcatctcct cccagcagca atccatgcgc ctggctaacc tcctgatgct | 1800 |
| cctgtcccac gtcaggcatg cgagtaacaa gggcatggaa catctgctca acatgaagtg | 1860 |
| caaaaatgtg gtcccagtgt atgacctgct gctggagatg ctgaatgccc acgtgcttcg | 1920 |
| cgggtgcaag tcctccatca cggggtccga gtgcagcccg gcagaggaca gtaaaagcaa | 1980 |
| agagggctcc cagaacccac agtctcagtg a | 2011 |